US006180084B1

(12) United States Patent
Ruoslahti et al.

(10) Patent No.: US 6,180,084 B1
(45) Date of Patent: Jan. 30, 2001

(54) NGR RECEPTOR AND METHODS OF IDENTIFYING TUMOR HOMING MOLECULES THAT HOME TO ANGIOGENIC VASCULATURE USING SAME

(75) Inventors: Erkki Ruoslahti, Rancho Santa Fe; Renata Pasqualini, Solana Beach, both of CA (US)

(73) Assignee: The Burnham Institute, La Jolla, CA (US)

( * ) Notice: Under 35 U.S.C. 154(b), the term of this patent shall be extended for 0 days.

(21) Appl. No.: 09/139,802

(22) Filed: Aug. 25, 1998

(51) Int. Cl.$^7$ .......................... A61K 49/00; G01N 33/53; G01N 33/566

(52) U.S. Cl. ............................ 424/9.1; 424/9.2; 435/7.8; 436/501

(58) Field of Search ...................................... 424/9.1, 93.2, 424/9.2; 435/7.23, 7.8; 514/2; 530/300; 436/501

(56) References Cited

U.S. PATENT DOCUMENTS

| 5,536,814 | 7/1996 | Ruoslahti et al. . |
| 5,622,699 | 4/1997 | Ruoslahti et al. . |

FOREIGN PATENT DOCUMENTS

| WO95/14714 | 6/1995 | (WO) . |
| 97 10507 | 3/1997 | (WO) . |
| WO97/19954 | 5/1997 | (WO) . |
| WO97/39021 | 10/1997 | (WO) . |
| 98 10795 | 3/1998 | (WO) . |

OTHER PUBLICATIONS

Koivunen et al., Phage Libraries Displaying Cyclic Peptides with Different Ring Sizes: Ligand Specificities of the RGD–Directed Integrins, *BioTechnology*, 13:265–270 (1995).
Amoscato et al., "Surface aminopeptidase activity of human lymphocytes. I. Biochemical and biologic properties of intact cells," *J. Immunol.* 142:1245–1252 (1989).
Amoscato et al., "Neutral surface aminopeptidase activity of human tumor cell lines," *Biochim. Biophys. Acta.* 1041:317–319 (1990).
Arap et al., "Cancer treatment by targeted drug delivery to tumor vasculature," *Science* 279:377–380 (1998).
Baillie et al., "Tumor Vasculature—A Potential Therapeutic Target" *British J. Cancer* 72:257–267 (1995).
Bicknell, "Vascular targeting and the inhibition of angiogenesis," *Annuals of Oncology*, 5(Supp. 4): S45–S50 (1994).
Brooks et al., "Integrin $\alpha v\beta_3$ Antagonists Promote Tumor Regression by Inducing Apoptosis of Angiogenic Blood Vessels," *Cell*, 79:1157–1164.
Bruley–Rosset et al., "Restoration of impaired immune functions of aged animals by chronic bestatin treatment," *Immunology* 38:75–83 (1979).

Burrows and Thorpe, "Vascular Targeting—A New Approach to the Therapy of Solid Tumors" *Pharmac. Ther.* 64:155–174 (1994).
Chen et al., p161, a murine membrane protein expressed on mast cells and some macrophages, is mouse CD13/Aminopeptidase N. *J. Immunol.* 157:2593–2600 (1996).
Dvorak et al., "Structure of Solid Tumors and Their Vasculature: Implications for Therapy with Monoclonal Antibodies" *Cancer Cells* 3:77–85 (1991).
Favaloro et al., "Further characterization of human myeloid antigens (gp160,95; gp150; gp67): investigation of epitopic heterogeneity and non–haemopoietic distribution using panels of monoclonal antibodies belonging to CD–11b, CD–13 and CD–33," *Br. J. Haematol.* 69:163–171 (1988).
Folkman, "Addressing tumor blood vessels," *Nature Biotechnology*, 15:510 (1997).
Friedlander et al., "Definition of Two Angiogenic Pathways by Distinct $\alpha_v$ integrins," *Science*, 270:1500–1502 (1995).
Fujii et al., "Human melanoma invasion and metastasis enhancement by high expression of aminopeptidase N/CD13," *Clin. Exp. Metastasis* 13:337–344 (1995).
Hammes et al., "Subcutaneous injection of a cyclic peptide antagonist of vitronectin receptor–type integrins inhibits retinal neovascularization," *Nature Medicine*, 2(5): 529–533 (1996).
Hanahan, "Signaling Vascular Morphogenesis and Maintenance," *Science*, 277:48–50 (1997).
Healy et al., "Peptide Ligands for Integrin $\alpha_v\beta_3$ Selected from Random Phage Display Libraries," *Biochem.*, 34:3948–3955 (1995).
Huang et al., "Tumor Infarction in Mice by Antibody–Directed Targeting of Tissue Factor to Tumor Vasculature" *Science* 275:547–550 (1997).
Kerbel, "Inhibition of Tumor Angiogenesis as a Strategy to Circumvent Acquired Resistance to Anti–Cancer Therapeutic Agents," *BioEssays*, 13 (1) :31–36 (1991).

(List continued on next page.)

*Primary Examiner*—Christina Y. Chan
*Assistant Examiner*—Gerald R. Ewoldt
(74) *Attorney, Agent, or Firm*—Campbell & Flores LLP

(57) ABSTRACT

The present invention provides a method of identifying a tumor homing molecule that homes to angiogenic vasculature by contacting a substantially purified NGR receptor with one or more molecules and determining specific binding of a molecule to the NGR receptor, where the presence of specific binding identifies the molecule as a tumor homing molecule that homes to angiogenic vasculature. The invention also provides a method of directing a moiety to angiogenic vasculature in a subject by administering to the subject a conjugate including a moiety linked to a tumor homing molecule that exhibits specific binding to an NGR receptor, whereby the moiety is directed to angiogenic vasculature. In addition, the invention provides a method of imaging the angiogenic vasculature of a tumor in a subject by administering to the subject a conjugate having a detectable moiety linked to a tumor homing molecule that exhibits specific binding to an NGR receptor and detecting the conjugate.

3 Claims, 16 Drawing Sheets-

OTHER PUBLICATIONS

Koch et al., "Monoclonal antibodies detect monocyte/macrophage activation and differentiation antigens and identify functionally distinct subpopulations of human rheumatoid synovial tissue macrophages," *Am. J. Pathol.* 138:165–173 (1991).

Koivunen et al., "Selection of peptides binding to the α5β1 integrin from phage display library," *J. Biol. Chem.* 268:20205–20210 (1993).

Lappi, "Tumor Targeting Through Fibroblast Growth Factor Receptors" *Cancer Biology* 6:279–288 (1995).

Look et al., "Human myeloid plasma membrane glycoprotein CD13 (gp150) is identical to aminopeptidase N," *J. Clin. Invest.* 83:1299–1307 (1989).

Makrynikola et al., "Functional and phenotypic upregulation of CD13/aminopeptidase–N on precursor–B acute lymphoblastic leukemia after in vitro stimulation," *Exp. Hematol.* 23:1173–1179 (1995).

Martiny–Baron and Marmé, "VEGF–mediated Tumor Angiogenesis: A New Target for Cancer Therapy" *Current Opinion Biotechnol* 6:675–680 (1995).

Mechtersheimer and Möller, "Expression of aminopeptidase N (CD13) in mesenchymal tumors," *Am. J. Pathol.* 137:1215–1222 (1990).

Menrad et al., "Biochemical and functional characterization of aminopeptidase N expressed by human melanoma cells," *Cancer Res.* 53:1450–1455 (1993).

Nagy et al., "Synthesis and biological evalution of cytotoxic analogs of somatostatin containing doxorubicin or its intensely potent derivative, 2–pyrrolinodoxorubicin," *Proc. Natl. Acad. Sci. USA* 95:1794–1799 (1998).

Nagy et al., "Cytotoxic analogs of luteinizing hormone–releasing hormone containing doxorubicin or 2–pyrrolinodoxorubicin, a derivative 500–1000 times more potent," *Proc. Natl. Acad. Sci. USA*, 93:7269–7273 (1996).

Pasqualini et al., "αv Integrins as receptors for tumor targeting by circulating ligands," *Nature Biotechnology*, 15:542–546 (1997).

Pasqualini and Ruoslahti, "Organ Targeting in vivo Using Phage Display Peptide Libraries" *Nature* 380:364–366 (1996).

Pasqualini et al., "A peptide isolated from phage display libraries is a structural and functional mimic of an RGD–binding site on integrins," *J. Cell Biol.* 130:1189–1196 (1995).

Rak et al., "Consequences of angiogenesis for tumor progression, metastasis and cancer therapy," *Anti–Cancer Drugs*, 6:3–18 (1995).

Rawlings and Barret, "Evolutionary families of peptidases," *Biochem J.* 290:205–218 (1993).

Riemann et al., "Induction of aminopeptidase N/CD13 on human lymphocytes after adhesion to fibroblast–like synoviocytes, endothelial cells, epithelial cells, and monocytes/macrophages," *J. Immunol.* 158:3425–3432 (1997).

Ruoslahti, "RGD and other recognition sequences for integrins," *Annu. Rev. Cell Dev. Biol.*, 12:697–715 (1996).

Saiki et al., "Role of aminopeptidase N (CD13) in tumor–cell invasion and extracellular matrix degradation," *Int. J. Cancer* 54:137–143 (1993).

Schlingemann et al., "Aminopeptidase A is a constituent of activated pericytes in angiogenesis," *J. Pathol.* 179:436–442 (1996).

Sin et al., "The anti–angiogenic agent fumagillin covalently binds and inhibits the methionine aminopeptidase, MetAP–2," *Proc. Natl. Acad. Sci USA* 94:6099–6103 (1997).

Taylor, "Aminopeptidases: structure and function," *FASEB J.* 7:290–298 (1993).

Trail et al., "Cure of Xenografted Human Carcinomas by BR96–Doxorubicin Immunoconjugates," *Science*, 261:212–215 (1993).

van Hal et al., Potential indirect anti–inflammatory effects of IL–4. Stimulation of human monocytes, macrophages, and endothelial cells by IL–4 increases aminopeptidase–N activity (CD13; EC 3.4.11.2) *J. Immunol.* 153:2718–2728 (1994).

Xu et al., "Cryptic and regulatory epitopes in CD13/aminopeptidase N," *Exp. Hematol.* 25:521–529 (1997).

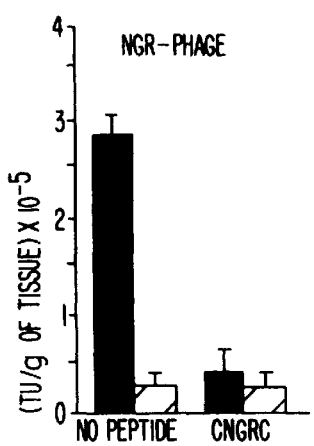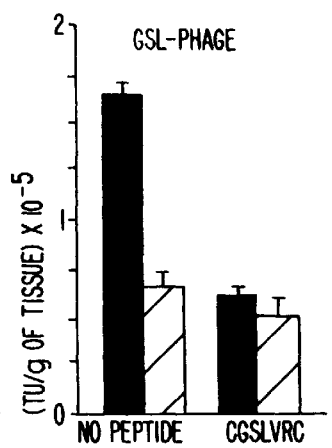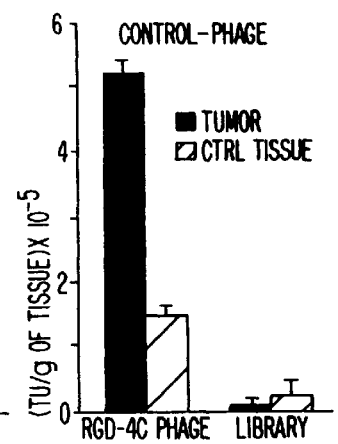
FIG. 1A-1  FIG. 1A-2  FIG. 1A-3
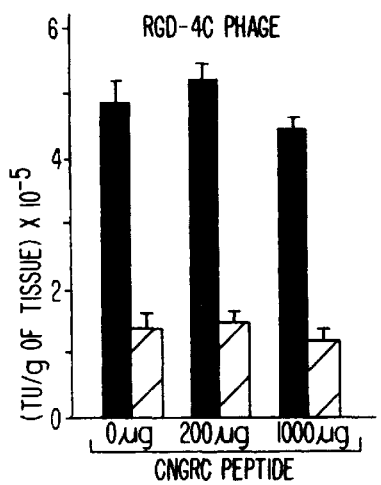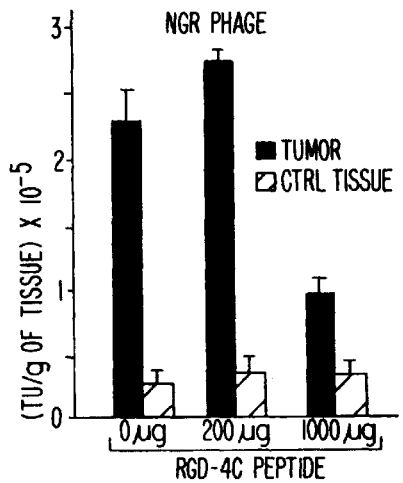
FIG. 1B-1  FIG. 1B-2
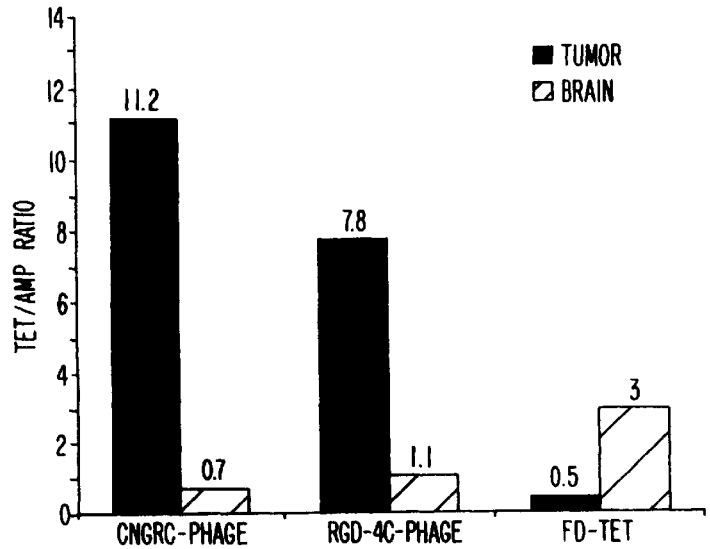
FIG. 2

```
    TAATTTTGC CCAGTCTGCC TGTTGTGGGG CTCCTCCCT TTGGGGATAT AAGCCCGGCC TGGGGCTGCT CC
    GTTCTCTG GCTGGCCCTGA GGCTCCCTGA GCCGCCTCCC CACCATCACC
```

```
1
    ATG GCC AAG GGC TTC TAT ATT TCC AAG TCC CTG GGG ATC CTC CTG GGC GTG
121 MET Ala Lys Gly Phe Tyr Ile Ser Lys Ser Leu Gly Ile Leu Leu Gly Val
1

GCA GCC GTG TGC ACA ATC ATC GCA CTG TCA GTG GTG TAC TCA GAG AAG AAC AAG AAC
    Ala Ala Val Cys Thr Ile Ile Ala Leu Ser Val Val Tyr Ser Gln Glu Lys Asn Lys Asn

241 GCC AAC AGC TCC CCC GTG GCC TCC ACC CCG TCA GCC TCC ACC GCC AAC CCC GCC
41  Ala Asn Ser Ser Pro Val Ala Ser Thr Thr Pro Ser Ala Ser Thr Ala Asn Pro Ala

TCG GCC ACC ACC TTG GAC CAA AGT GCG TGG AAT CGT TAC CTC CCC AAC ACG CTG
    Ser Ala Thr Thr Leu Asp Gln Ser Ala Trp Asn Arg Tyr Leu Pro Asn Thr Leu

361 AAA CCC GAT TCC TAC CAG GTG ACG CTG AGA CCG TAC CTC ACC AAT GAC AGG GGC CTG
81  Lys Pro Asp Ser Tyr Gln Val Thr Leu Arg Pro Tyr Leu Thr Asn Asp Arg Gly Leu

TAC GTT TTT AAG GGA AAG TCC CGT GTC CGT TTC CGT GAG GCC ACT GAC GTC ATC
    Tyr Val Phe Lys Gly Lys Ser Arg Val Arg Phe Arg Glu Ala Thr Asp Val Ile

481 ATC CAC AGC AAG CTC AAG TAC ACC CTC AGC AAG CAG ACT GAG AAG GTG GTC CTG CGT
121 Ile His Ser Lys Leu Asn Tyr Thr Leu Ser Gln Thr Glu Lys Val Val Leu Arg

GGT GTG GGA CAC CAG TCC CAG CCC GAT CCC AAG GAG GTG GAG CCC ATG GAG
    Gly Val Gly His Ser Gln Pro Asp Pro Lys Glu Val Glu Pro Met Glu

601 TAC CTG GTG GTG CAC CTC AAG TCC GGT CAA AAG GAG CAG AGC AGC GAC ATG AGC
161 Tyr Leu Val Val His Leu Ser Gly Gln Lys Glu Gln Ser Ser Asp Met Ser

GAG TTC GAG GGG GAG TTG GCA GAT GAC CTG GCG GGC GGC TTC TAC AGC GAG TAC ATG GAG
    Glu Phe Glu Gly Glu Leu Ala Asp Asp Leu Ala Gly Gly Phe Tyr Ser Glu Tyr Met Glu
```

FIG. 12A

```
721   GGC AAT GTC AGA AAG GTG GCC ACT ACA CAG ATG CAG GCT GCA GAT GCC CGG AAG TCC
201   Gly Asn Val Arg Lys Val Ala Thr Thr Gln Met Gln Ala Ala Asp Ala Arg Lys Ser

TTC CCA TGC TTC GAT GAG GTG GCC GCC CCG ATG GAG GCC AAG ATC ACG GCA CTT CAC CCC
      Phe Pro Cys Phe Asp Glu Val Ala Ala Pro Met Glu Ala Lys Ile Thr Ala Leu His Pro

841   AAG GAC CTG ACA GCC CTG TCC AAC ATG ATG CTT CCC AGC ACC ACC CCA GAA
241   Lys Asp Leu Thr Ala Leu Ser Asn Met Met Leu Pro Ser Thr Thr Pro Glu

GAC CCC AAC TGG AAT GTC ACT GTC AAC TTC CAC AAG ATG TCC AAT GCC ACG TAC CTG
      Asp Pro Asn Trp Asn Val Thr Val Asn Phe His Lys Met Ser Asn Ala Thr Tyr Leu

961   GCC TTC ATT GTC AGT GAG GAG TTC TAC GTG GAG CAG AAT GGT GTC TTG ATC
281   Ala Phe Ile Val Ser Glu Glu Phe Tyr Val Glu Gln Asn Gly Val Leu Ile

CGG ATC TGG GCC CGG CCC AGT GCT ATT GCC CAT TAT GAC GCC CTG AAC GTG
      Arg Ile Trp Ala Arg Pro Ser Ala Ile Ala His Tyr Asp Ala Leu Asn Val

1081  ACG GGC CCC ATC ATT TTT GCT GAC TAT GGC GCC AAC CCC TAC CCA AAA
321   Thr Gly Pro Ile Ile Phe Ala Asp Tyr Gly Ala Asn Pro Tyr Pro Lys

TCA GAC CAG ATT GGC GAG CTG CCA GAC TTC CAG GCC ATG TCC AGC GGA CTG GTG
      Ser Asp Gln Ile Gly Glu Leu Pro Asp Phe Gln Ala Met Ser Ser Gly Leu Val

1201  ACC TAC CGG GTC AAC GAG CAG CTG TCC CAT CAT CTG ATG TGG GGG AAC CTG AAG GAG
361   Thr Tyr Arg Val Asn Glu Gln Leu Ser His His Leu Met Trp Gly Asn Leu Lys Glu

CGG GTG GTC ACT GAG GAG CAT CTG CTG CAT GGC TTC TTC TAC ATG GTG CTG ACC
      Arg Val Val Thr Glu Glu His Leu Leu His Gly Phe Phe Tyr Met Val Leu Thr

1321  ATA GAG TGG TGG AAT GAC GAG CTG CTG AAC AAC TAC TCC TAC TAC GAG CTG
401   Ile Glu Trp Trp Asn Asp Glu Leu Leu Asn Asn Tyr Ser Tyr Tyr Glu Leu

GGT GCT TAT GCG GAG CCC CCC AAC TGG AAC TTG AAA GAC CTC ATG GTG CTG GAT GTG
      Gly Ala Tyr Ala Glu Pro Pro Asn Trp Asn Leu Lys Asp Leu Met Val Leu Asp Val
```

FIG. 12B

```
1441  TAC CGC GTG ATG GCA GTG GAT GCA CTG GCC TCC CAC CCG CTG TCC ACA CCC GCC TCG
441   Tyr Arg Val Met Ala Val Asp Ala Leu Ala Ser His Pro Leu Ser Thr Pro Ala Ser

1561  GAG ATC AAC ACG CCG GCC ATG CAG CAG ATC GAG TTT GAC GCC CTG TCC TAC AGC GGC
481   Glu Ile Asn Thr Pro Ala Met Gln Gln Ile Glu Phe Asp Ala Leu Ser Tyr Ser Gly

1561  GCC TCA GTC CTC AGG ATG TCC TCC AGC AGC TTC CTG TCC TTC TTC AAG CAG GGC CTG
481   Ala Ser Val Leu Arg Met Ser Ser Ser Ser Phe Leu Ser Phe Phe Lys Gln Gly Leu

1681  GCG TCC CTC CAC ACC TTT GCC TAC CAG TAC CTG TTC AAC AAC CTG TGG GAC GAC CAC
521   Ala Ser Leu His Thr Phe Ala Tyr Gln Tyr Leu Phe Asn Asn Leu Trp Asp Asp His

1681  CTG CAG GAG GCT GTG AAC CGG GAT GCA CTG AGC TCC ACC GTG ACC CGG AGC ATC ATG
521   Leu Gln Glu Ala Val Asn Arg Asp Ala Leu Ser Ser Thr Val Thr Arg Ser Ile Met

1801  AAC CGC TGG ACC CTG CAG ATG GGC GGC TTC TTC ATC CCC CCC GAT GTG ACC GGG ACC
561   Asn Arg Trp Thr Leu Gln Met Gly Gly Phe Phe Ile Pro Pro Asp Val Thr Gly Thr

1801  CTT TCC CAG GAG CAC ATT CTC TTC CTT CCC ATC GAT GAT GTT ACC CGC CAG CCC TCA
561   Leu Ser Gln Glu His Ile Leu Phe Leu Pro Ile Asp Asp Val Thr Arg Gln Pro Ser

1921  AAC TAC GTG TGG ATT GTG AGA AGA GCC ATC ACA AAC TCC AGC TTC TTC AGA TCA GAG
601   Asn Tyr Val Trp Ile Val Arg Arg Ala Ile Thr Asn Ser Ser Phe Phe Arg Ser Glu

1921  TGG CTG ATA GAT GTA CAG CTG ACG GGC TAT TAC GGC GTG GTG AAC AAT GAG CAG AAC
601   Trp Leu Ile Asp Val Gln Leu Thr Gly Tyr Tyr Gly Val Val Asn Asn Glu Gln Asn

2041  CTG CTG AAC ACT CAG CTG CAG AGA GAC GAC CAC TAC TAT TAC CCT GTC ATC AAT AAT
641   Leu Leu Asn Thr Gln Leu Gln Arg Asp Asp His Tyr Tyr Tyr Pro Val Ile Asn Asn

2041  AAG ATT GAC CAG ACT TTC AAC CTG GCC AGT GCC CAT AAG GTC CCT GCA TGG GCA CAG
641   Lys Ile Asp Gln Thr Phe Asn Leu Ala Ser Ala His Lys Val Pro Ala Trp Ala Gln

ATC ATT AAT GAC GCC TTC AAC CTG AAC GTC ACT GTC CCT GCG CTG
     Ile Ile Asn Asp Ala Phe Asn Leu Asn Val Thr Val Pro Ala Leu
```

FIG. 12C

| | | | | | | | | | | | | | | | | |
|---|---|---|---|---|---|---|---|---|---|---|---|---|---|---|---|---|
| 2161<br>681 | AAC<br>Asn | ACC<br>Thr | CTC<br>Leu | TTC<br>Phe | CTG<br>Leu | ATT<br>Ile | GAA<br>Glu | GAG<br>Glu | CAG<br>Gln | AGA<br>Arg | TAC<br>Tyr | ATG<br>Met | CCC<br>Pro | TGG<br>Trp | GAG<br>Glu | GCC<br>Ala | GCC<br>Ala | CTG<br>Leu | AGC<br>Ser |
| 2281<br>721 | AGC<br>Ser | CTG<br>Leu | TAC<br>Tyr | TTC<br>Phe | AAG<br>Lys | CTC<br>Leu | ATG<br>Met | TTT<br>Phe | GAC<br>Asp | CGC<br>Arg | TCC<br>Ser | GAG<br>Glu | GTC<br>Val | TAT<br>Tyr | GGC<br>Gly | CCC<br>Pro | ATG<br>Met | AAG<br>Lys |
| 2401<br>761 | TAC<br>Tyr | CTG<br>Leu | AAG<br>Lys | TTC<br>Phe | CAG<br>Gln | GTC<br>Val | ACA<br>Thr | CCC<br>Pro | CTC<br>Leu | TTC<br>Phe | CAC<br>His | ATT<br>Ile | TTC<br>Phe | AGA<br>Arg | AAT<br>Asn | AAT<br>Asn | ACC<br>Thr | AAC<br>Asn | TGG<br>Trp |
| 2521<br>801 | AGG<br>Arg | GAG<br>Glu | ATC<br>Ile | CCA<br>Pro | GAA<br>Glu | AAC<br>Asn | CTG<br>Leu | ATG<br>Met | GAC<br>Asp | CAG<br>Gln | TAC<br>Tyr | GAG<br>Glu | GTT<br>Val | GAG<br>Glu | AAT<br>Asn | AAT<br>Asn | AGC<br>Ser | ATC<br>Ile | GCC<br>Ala |
| | ACC<br>Thr | GCC<br>Ala |
| 2641<br>841 | TCC<br>Ser | AAC<br>Asn | GGA<br>Gly | GTT<br>Val | CCA<br>Pro | TGT<br>Cys | GAG<br>Glu | ATG<br>Met | GTC<br>Val | TCT<br>Ser | CGG<br>Arg | CTG<br>Leu | CTT<br>Leu | TTC<br>Phe | AAG<br>Lys | CAG<br>Gln | TGG<br>Trp | ATG<br>Met |
| 2761<br>881 | GAG<br>Glu | AAC<br>Asn | CCC<br>Pro | AAC<br>Asn | AAT<br>Asn | CAC<br>His | ATC<br>Ile | CCG<br>Pro | GAG<br>Glu | GAG<br>Glu | TTC<br>Phe | GAC<br>Asp | TGG<br>Trp | CGG<br>Arg | GCA<br>Ala | GCC<br>Ala | CTG<br>Leu | TTA<br>Leu | GAC<br>Asp | CAA<br>Gln | GGG<br>Gly | ATT<br>Ile | GTC<br>Val | AAC<br>Asn | GTG<br>Val | AAG<br>Lys |

FIG. 12D

```
2881  TTC AAG AAG GAC AAC GAG GAA ACA GGC TTC GGC TCA GGC ACC CGG GCC CTG GAG CAA GCC
921   Phe Lys Lys Asp Asn Glu Glu Thr Gly Phe Gly Ser Gly Thr Arg Ala Leu Glu Gln Ala

CTG GAG AAG ACG AAA GCC AAC ATC AAG TGG GTG AAG GAG AAC AAG GAG GTG GTG CTC CAG
      Leu Glu Lys Thr Lys Ala Asn Ile Lys Trp Val Lys Glu Asn Lys Glu Val Val Leu Gln
                                                                            **

3001  TGG TTC ACA GAA AAC AGC AAA TAGTCCCCA GCCCTTGAAG TCACCCGGCC CCGATGCAAG GTGCCCAC
961   Trp Phe Thr Glu Asn Ser Lys
                    **

AT GTGTCCATCC CAGCGGGCTGG TGCAGGGCCT CCATTCCTGG AGCCCGAGGC

3121  ACCAGTGTCC TCCCCTCAAG GACAAAGTCT CCAGCCCACG TTCTCTCTGC CTGTGAGCCA GTCTAGTTCC TG

ATGACCCA GGCTGCCTGA GCACCTCCCA GCCCCTGCCC CTCATGCCAA
                                                    *

3241  CCCCGCCCTA GGCCTGGGCAT GGCACCTGTC GCCCAGTGCC CTGGGGCTGA TCTCAGGGAA GCCCAGCTCC AG

GGCCAGAT GAGCAGAAGC TCTCGATGGA CAATGAACGG CCTTGCTGGG

3361  GGCCGCCCTG TACCCTCTTT CACCTTTCCC TAAAGACCCT AAATCTGAGG AATCAACAGG GCAGCAGATC TG

TATATTTT TTTCTAAGAG AAAATGTAAA TAAAGGATTT CTAGATGAAA
                                    _____
                            *
3481  AAAAAAAAAA AAAA
```

FIG. 12E

NGR RECEPTOR AND METHODS OF IDENTIFYING TUMOR HOMING MOLECULES THAT HOME TO ANGIOGENIC VASCULATURE USING SAME

This invention was made with government support under CA 42507, CA 62042, CA74238-01 and Cancer Center Support Grant CA 30199 awarded by the National Institutes of Health. The government has certain rights in this invention.

BACKGROUND OF THE INVENTION

1. Field of the Invention

The present invention relates generally to the fields of cancer biology and drug delivery and, more specifically, to peptides that selectively home to a tumor, particularly a malignant tumor, to compositions comprising an agent such as a therapeutic agent conjugated to such tumor homing molecules, and to methods of using such molecules to target an agent to a tumor.

2. Background Information

Continuous developments over the past quarter century have resulted in substantial improvements in the ability of a physician to diagnose a cancer in a patient. For example, antibody based assays such as that for prostate specific antigen now allow early diagnosis of cancers such as prostate cancer. More recently, methods of genetic screening are becoming available to identify persons that may be particularly susceptible to developing a cancer. Genetic screening methods are based on the identification of one or more mutations in a gene that correlates with the development of a cancer. For example, the identification of genes such as BRCA1 and BRCA2 allowed the further identification of mutations in these genes that, in some cases, can correlate with susceptibility to developing breast cancer.

Unfortunately, methods for treating cancer have not kept pace with those for diagnosing the disease. Thus, while the death rate from various cancers has decreased due to the ability of a physician to detect the disease at an earlier stage, the ability to treat patients presenting with more advanced disease has advanced only minimally.

A major hurdle to advances in treating cancer is the relative lack of agents that can selectively target the cancer, while sparing normal tissue. For example, radiation therapy and surgery, which generally are localized treatments, can cause substantial damage to normal tissue in the treatment field, resulting in scarring and, in severe cases, loss of function of the normal tissue. Chemotherapy, in comparison, which generally is administered systemically, can cause substantial damage to organs such as bone marrow, mucosae, skin and the small intestine, which undergo rapid cell turnover and continuous cell division. As a result, undesirable side effects such as nausea, loss of hair and drop in blood cell count occur as a result of systemically treating a cancer patient with chemotherapeutic agents. Such undesirable side effects often limit the amount of a treatment that can be administered. Thus, cancer remains a leading cause of patient morbidity and death.

Efforts have been made to increase the target specificity of various drugs. For example, where a unique cell surface marker is expressed by a population of cells making up a tumor, an antibody can be raised against the unique marker and a drug can be linked to the antibody. Upon administration of the drug/antibody complex to the patient, the binding of the antibody to the marker results in the delivery of a relatively high concentration of the drug to the tumor. Similar methods can be used where a particular cancer cell or the supporting cell or matrix expresses a unique cell surface receptor or a ligand for a particular receptor. In these cases, the drug can be linked to the specific ligand or to the receptor, respectively, thus providing a means to deliver a relatively high concentration of the drug to the tumor.

Tumors are characterized, in part, by a relatively high level of active angiogenesis, resulting in the continual formation of new blood vessels to support the growing tumor. Such angiogenic blood vessels are distinguishable from mature vasculature. One of the distinguishing features of angiogenic vasculature is that unique endothelial cell surface markers are expressed. Thus, the blood vessels in a tumor provide a potential target for directing a chemotherapeutic agent to the tumor, thereby reducing the likelihood that the agent will kill sensitive normal tissues. Furthermore, if agents that target the angiogenic blood vessels in a tumor can be identified, there is as likelihood that the agents can be useful against a variety of different types of tumors, since it is the target molecules in the angiogenic vessels that are recognized by such agents and not receptors specific for the tumor cells. However, the use of molecules that can bind specifically to tumor vasculature and target a chemotherapeutic agent to the tumor has not been demonstrated.

While linking a drug to a molecule that homes to a tumor can provide significant advantages for treatment over the use of a drug, alone, use of this method is severely limited by the scarcity of useful cell surface markers expressed in a tumor. Thus, a need exists to identify molecules that can selectively home to a tumor, particularly to the vasculature supporting the tumor. The present invention satisfies this need and provides related advantages as well.

SUMMARY OF THE INVENTION

The present invention provides a method of identifying a tumor homing molecule that homes to angiogenic vasculature of a tumor. The method includes the steps of contacting a substantially purified NGR receptor with one or more molecules and determining specific binding of a molecule to the NGR receptor, where the presence of specific binding identifies the molecule as a tumor homing molecule that homes to angiogenic vasculature of a tumor. In a method of the invention, the substantially purified NCR receptor can be, for example, CD13/aminopeptidase N. If desired, the substantially purified NGR receptor can be immobilized on a support such as a plate or a bead.

The invention also provides a method of identifying a homing molecule that homes to angiogenic vasculature using substantially purified NGR receptor. The method includes the steps of contacting a substantially purified NGR receptor with one or more molecules and determining specific binding of a molecule to the NGR receptor, where presence of specific binding identifies the molecule as a homing molecule that homes to angiogenic vasculature. The invention provides homing molecules that home to non-tumor angiogenic vasculature.

The present invention also provides a method of directing a moiety to angiogenic vasculature of a tumor in a subject by administering to the subject a conjugate including a moiety linked to a tumor homing molecule that exhibits specific binding to an NGR receptor, whereby the moiety is directed to angiogenic vasculature of a tumor. In a method of the invention, the tumor homing molecule can be, for example, a peptide containing the sequence NGR, and, if desired, can be part of a conjugate in which the moiety is a cytotoxic agent, drug or cancer therapeutic agent, for example, doxorubicin. A tumor homing peptide containing the sequence NGR can have, for example, the sequence CNGRCVSG-CAGRC (SEQ ID NO:3), NGRAHA (SEQ ID NO:6), CVLNGRMEC (SEQ ID NO:7) or CNGRC (SEQ ID NO:8). In a method of the invention for directing a moiety to angiogenic vasculature of a tumor in a subject, the tumor homing molecule also can be, for example, an aminopeptidase inhibitor such as bestatin, o-phenanthroline, actinonin, amastatin, 2,2'-dipyridyl or fumagillin and can be linked, if desired, to a drug moiety.

Further provided herein is a method of imaging the angiogenic vasculature of a tumor in a subject by administering to the subject a conjugate having a detectable moiety linked to a tumor homing molecule that exhibits specific binding to an NGR receptor, whereby the conjugate selectively binds the angiogenic vasculature, and detecting the conjugate. A detectable moiety for imaging angiogenic vasculature can be, for example, a radionuclide. A useful tumor homing molecule for imaging angiogenic vasculature can be, for example, a peptide containing the sequence NGR, such as a peptide containing the sequence CNGRCVSGCAGRC (SEQ ID NQ:3), NGRAHA (SEQ ID NO:6), CVLNGRMEC (SEQ ID NO:7) or CNGRC (SEQ ID NO:8). A tumor homing molecule for imaging angiogenic vasculature also can be, for example, an aminopeptidase inhibitor such as bestatin, o-phenanthroline, actinonin, amastatin, 2,2'-dipyridyl, fumagillin or another molecule that inhibits an aminopeptidase.

The invention also provides inhibitors of angiogenesis that are NGR receptor binding molecules. Such inhibitors can be, for example, an NGR receptor antibody or an aminopeptidase inhibitor such as bestatin, o-phenanthroline, actinonin, amastatin, 2,2'-dipyridyl or fumagillin, or a conjugate of such angiogenesis inhibitors to a drug or toxin.

BRIEF DESCRIPTION OF THE DRAWINGS

FIG. 1 shows inhibition of in vivo phage homing by synthetic peptides. Recovery of phage displaying tumor homing peptides from breast carcinoma xenografts was measured after injection of phage or coinjection of the phage with various peptides. (A) Left panel: Recovery of phage expressing the NGR tumor homing peptide, CNGRCVSG-CAGRC (SEQ ID NO:3; "NGR phage") from tumor (filled bars) and brain (striped bars), and inhibition of the tumor homing by the soluble peptide CNGRC (SEQ ID NO:8). Middle panel: Recovery of CGSLVRC-phage and inhibition of the tumor homing by the soluble peptide CGSLVRC. Right panel: Recovery of RGD-4C phage (positive control; the peptide insert in the RGD-4C phage is CDCRGDCFC; SEQ ID NO:1) and unselected phage library mix (negative control). (B) Left panel: Increasing amounts of the RGD-4C soluble peptide were injected with the CNGRCVSGCAGRC-phage. Right panel: Increasing amounts of the CNGRC soluble peptide were injected with the RGD-4C phage.

FIG. 2 shows the specificity of tumor homing by the NGR phage relative to the positive control (RGD-4C) and negative control (fd-tet) phage.

FIGS. 3A, 3C, 3G and 3J are from mice receiving insertless phage (control phage) and FIGS. 3B, 3D, 3E, 3F, 3H, 3I and 3K to 3V are from mice receiving NGR phage. FIGS. 3A, 3B, 3E, 3F and 3G are breast tumor samples; FIGS. 3C, 3D, 3H, 3I and 3J are Kaposi's sarcoma samples; FIG. 3K is brain; FIG. 3L is lymph node; FIG. 3M is kidney; FIG. 3N is pancreas; FIG. 3O is uterus; FIG. 3P is mammary fat pad; FIG. 3Q is lung; FIG. 3R is intestine; FIG. 3S is skin; FIG. 3T is skeletal muscle; FIG. 3U is heart and FIG. 3V is urinary tract epithelium. Magnification: FIGS. 3A to 3D, 40×; FIGS. 3E to 3V, 200×.

FIG. 12 shows the nucleotide and amino acid sequences of CD13/aminopeptidase N (SEQ ID NOS:200 and 201, respectively).

DETAILED DESCRIPTION OF THE INVENTION

Figure 3A:
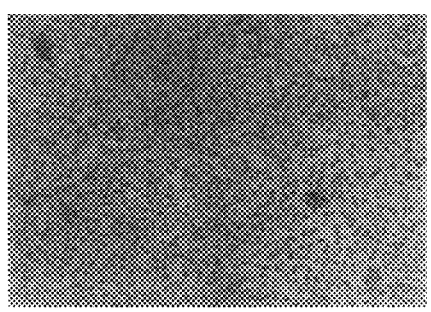
FIGS. 3A to 3V show the immunohistochemical staining of the NGR phage in tumors and normal tissues following intravenous injection into nude mice bearing a human breast carcinoma or a human Kaposi's sarcoma. Samples were taken 4 min (FIGS. 3E, 3G, 3H and 3J) or 24 hr (FIGS. 3A to 3D, 3F, 3I, and 3K to 3V) after administration of the phage.
Figure 3E:
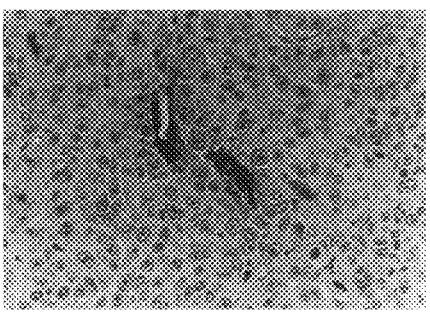
Figure 3B:
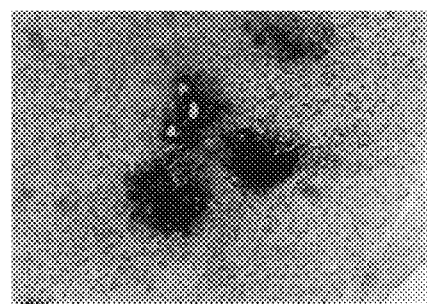
Figure 3F:
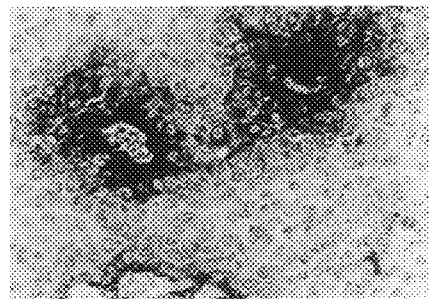

The present invention relates to the identification of a target molecule responsible for the homing of molecules to angiogenic vasculature. The identified target molecule can act as a receptor, for example, for tumor homing molecules that home to the angiogenic vasculature of a tumor. As disclosed herein, various tumor homing molecules were isolated using in vivo panning; a core binding motif present in several of the tumor homing peptides was identified as the sequence NGR (see Example IV). In particular, phage expressing the peptides CNGRCVSGCAGRC (SEQ ID NO:3), NGRAHA (SEQ ID NO:6) and CVLNGRMEC (SEQ ID NO:7) homed to human breast carcinomas, human Kaposi's sarcomas and mouse melanomas in mice bearing these tumors. Furthermore, such homing was competitively inhibited in vivo by the NGR containing peptide CNGRC (SEQ ID NO:8) but not by an unrelated peptide. Thus, the results disclosed herein indicate that a tumor homing peptide containing NGR can home to and specifically bind tumors of different types and species origin.

As further disclosed herein, a receptor that specifically binds tumor homing molecules containing the NGR motif has been identified (see Examples IX and X). Characterization of the NGR receptor revealed that this molecule immunoreacts with CD13 antibodies and that the isolated receptor specifically binds the NGR motif. Furthermore, the NGR receptor was expressed in angiogenic vasculature, including tumor vasculature, and is functionally important in angiogenesis. The identification of a target molecule such as the NGR receptor that is expressed in angiogenic vasculature can be advantageously used in vitro to identify new homing molecules, including high affinity ligands of the NGR receptor, as well as to target a tumor homing molecule and a linked moiety, such as a drug, to the angiogenic vasculature of a tumor in vivo.

Thus, the present invention provides a method of identifying a tumor homing molecule that homes to angiogenic vasculature of a tumor by using a substantially purified NGR receptor to identify the molecule. The method includes the steps of contacting a substantially purified NGR receptor with one or more molecules and determining specific binding of a molecule to the NGR receptor, where the presence of specific binding identifies the molecule as a tumor homing molecule that homes to angiogenic vasculature of a tumor. A method of the invention directed to identifying a tumor homing molecule that homes to angiogenic vasculature of a tumor can additionally include the steps of administering an NGR binding molecule in vivo and determining binding of the NGR binding molecule to angiogenic vasculature. If desired, the substantially purified NGR receptor can be immobilized on a support such as a plate or a bead.

In a method of the invention, the substantially purified NGR receptor can be, for example, CD13/aminopeptidase N (FIG. 12; see, also, Look et al., *J. Clin. Invest.* 83:1299–1307 (1989), which is incorporated herein by reference). This highly conserved transmembrane glycoprotein of about 150 kDa is incorporated into the cell membrane through an N-terminal hydrophobic segment (Look et al., supra, 1989; Xu et al., *Exp. Hematol.* 25:521–529 (1997), which is incorporated herein by reference). The large extracellular carboxy-terminal domain contains a pentapeptide that is characteristic of many zinc-dependent metalloproteases (Look et al., supra, 1989). Homologs of CD13 from several different species are well conserved (Look et al., supra, 1989; Xu et al., supra, 1997; Turner et al., in *Mammalian Ectoenzymes,* Kenny and Turner, eds., Elsevier Scientific Publishing Co., Amsterdam, p. 211 (1987)).

CD13 is expressed in normal and malignant cells of the myeloid lineage (Amoscato et al., *J. Immunol.* 142:1245–1252 (1989); Favaloro et al., *Br. J. Haematol.* 69:163–171 (1988); Makrynikola et al., *Exp. Hematol.* 23:1173–1179 (1995)) as well as in many epithelial, endothelial, and tumor cell types (Amoscato et al., *Biochem. Biophys. Acta* 1041:317–319 (1990); Rawlings and Barret, *Biochem. J.* 290:205–218 (1993); Mechtersheimer and Moller, *Am. J. Pathol.* 137:1215–1222 (1990); Menrad et al., *Cancer Res.* 53:1450–1455 (1993); Riemann et al., *J. Immunol.* 158:3425–3432 (1997)). CD13 can function differently depending on its location. In synaptic membranes, CD13 metabolizes enkephalins and endorphins (Matsas et al., *FEBS Lett.* 175:124–128 (1984)); in the intestinal brush border, it degrades regulatory peptides and scavenges amino acids (Turner et al., supra, 1997; Rawlings and Barret, supra, 1993); in lymphocytes, the cell surface activity of CD13 is associated with mitotic activation, antigen processing (Mouritsen et al., *J. Immunol.* 149:1987–1993 (1992); Falk et al., *Immunogenetics* 39:230–242 (1994)), cell adhesion, and migration (Menrad et al., supra, 1993; Saiki et al., *Int. J. Cancer* 54:137–143 (1993); Koch et al., *Am. J. Pathol.* 138:165–173 (1991)). In addition, CD13 has also been implicated in tumor invasion (Saiki et al., supra, 1993; Fujii et al., *Clin. Exp. Metastasis* 13:337–344 (1995)), signal transduction (O'Connell et al., *Transplant. Proc.* 21:3826–3827 (1989)), cell cycle control and differentiation (Makrynikola et al., supra, 1995;, Riemann et al., supra, 1997), and as a receptor for viruses (Delmas et al., *Nature* 357:417–420 (1992); Yeager et al., *Nature* 357:420–422 (1992)).

The expression levels and enzymatic activity of CD13 can be physiologically regulated, with the activity and substrate specificity of CD13 correlating with conformational changes and induced by various stimuli such as proliferative signals to cells. Studies using monoclonal antibodies also have indicated that CD13 undergoes regulatory intramolecular alterations that can result in the exposure of cryptic sites and can regulate enzyme activity. The presence of certain epitopes has also been related to prognosis of acute myeloid leukemia (Xu et al., supra, 1997; Favaloro et al., supra, 1988; Makrynikola et al., supra, 1995).

Cell-surface CD13/aminopeptidase N enzymatic activity can be potently blocked by bestatin, o-phenanthroline and actinonin (Taylor, *FASEB J.* 7:290–298 (1993); Rawlings and Barret, supra, 1993; Saiki et al., supra, 1993). Moreover, bestatin has been shown to possess immunomodulatory effects, and administration of high doses of bestatin results in marked suppression of experimental and spontaneous metastasis and inhibition of tumor cell invasion (Bruley-Rosset et al. *Immunol.* 38:75–83 (1979); van Hal et al., *J.*

Immunol. 153:2718–2728 (1994); Saiki et al., supra, 1993; Fujii et al., supra, 1995)). Although CD13 is expressed outside the vascular system, the results disclosed herein indicate that an NGR receptor having immunoreactivity with an anti-CD13 antibody is only exposed to the circulation in tumor vessels (see Example XII).

As used herein, the term "NGR receptor" means a target molecule that is expressed in angiogenic vasculature and that specifically binds an NGR motif. As described below and in Examples IX and X, an NGR receptor has been substantially purified and demonstrated to specifically bind several NGR containing peptides but not unrelated control peptides. The NGR receptor disclosed herein exhibits characteristics of a highly conserved transmembrane aminopeptidase designated CD13/aminopeptidase N (CD13/APN). As disclosed herein, an NGR receptor can be a transmembrane receptor. An NGR receptor also can be a molecule that immunoreacts with an anti-CD13 monoclonal antibody and that has aminopeptidase activity. An NGR receptor can have, for example, an amino acid sequence that is substantially similar to the amino acid sequence of CD13/APN (SEQ ID NO:201). Such an NGR receptor can have an amino acid sequence identical to the sequence of CD13/APN (SEQ ID NO:201) or can have one or more modifications, such as deletions, insertions or substitutions, including conservative and non-conservative amino acid substitutions, as long as the receptor remains expressed in angiogenic vasculature and retains specific NGR binding activity. The term "NGR receptor" also is intended to include polypeptides encompassing, for example, modified forms of naturally occurring amino acids such as D-stereoisomers, non-naturally occurring amino acids, amino acid analogues and mimetics, so long as such polypeptides retain functional activity as defined above.

A functional fragment of an NGR receptor also can be useful in the methods of the invention, for example, for identifying tumor homing molecules that home to angiogenic vasculature of a tumor. As used herein, the term "functional fragment," when used in reference to an NGR receptor, refers to a portion of an NGR receptor that retains some or all binding activity to a homing molecule. Such a functional fragment can be, for example, a domain that binds an NGR motif, such as the extracellular domain of an NGR receptor or an epitope specifically reactive with an antibody. A functional fragment of an NGR receptor useful in identifying a tumor homing molecule can be, for example, the extracellular carboxy-terminal domain of CD13/aminopeptidase N (Look et al., supra, 1989).

As used herein, the term "specific binding" means binding that is measurably different from a non-specific interaction. Specific binding can be measured, for example, by determining binding of a molecule compared to binding of a control molecule, which generally is a molecule of similar structure that does not have binding activity, for example, a peptide of similar size that lacks NGR. In this case, specific binding is indicated if the molecule has measurably higher affinity for the NGR receptor than the control molecule. Specificity of binding can be determined, for example, by competition with a control molecule that is known to bind to a target. For example, specific binding of an NGR peptide can be demonstrated by competing for binding with the same NGR peptide or a different peptide containing an NGR motif. In this case, specific binding is indicated if the binding of a molecule is competitively inhibited by the second NGR containing peptide.

The term "specific binding," as used herein, includes both low and high affinity specific binding. Specific binding can be exhibited, for example, by a low affinity homing molecule having a Kd of at least about $10^{-4}$ M. For example, if the receptor for a homing molecule has more than one binding site, a homing molecule having low affinity can be useful for targeting angiogenic vasculature. Specific binding also can be exhibited by a high affinity homing molecule, for example, a homing molecule having a Kd of at least about of $10^{-7}$ M, at least about $10^{-8}$ M, at least about $10^{-9}$ M, at least about $10^{-10}$ M, or can have a Kd of at least about $10^{-11}$ M or $10^{-12}$ M or greater. Both low and high affinity homing molecules are useful for targeting angiogenic vasculature.

The vasculature within a tumor generally undergoes active angiogenesis, resulting in the continual formation of new blood vessels to support the growing tumor. Such angiogenic blood vessels are distinguishable from mature vasculature in that angiogenic vasculature expresses unique endothelial cell surface markers, including the $\alpha_v\beta_3$ integrin (Brooks, Cell 79:1157–1164 (1994), which is incorporated herein by reference); WO 95/14714, Int. Filing Date Nov. 22, 1994) and receptors for angiogenic growth factors (Mustonen and Alitalo, J. Cell Biol. 129:895–898 (1995); Lappi, Semin. Cancer Biol. 6:279–288 (1995)). Moreover, tumor vasculature is histologically distinguishable from blood vessel in general in that tumor vasculature is fenestrated (Folkman, Nature Med. 1:27–31 (1995); Rak et al., Anticancer Drugs 6:3–18 (1995)). Thus, angiogenic vasculature is a particularly attractive target for targeting a tumor homing molecule. Such a tumor homing molecule can be useful for directing an agent such as a chemotherapeutic drug to a tumor, while reducing the likelihood the agent will have a toxic effect on normal, healthy organs or tissues (Examples VIII and XV). Moreover, a molecule that homes selectively to angiogenic vasculature also may have use in targeting other types of neovasculature such as that present in inflammatory, regenerating or wounded tissues. As used herein, the term "tumor homing molecule that homes to angiogenic vasculature of a tumor" means a molecule that can bind specifically to a target molecule expressed in angiogenic vasculature of a tumor. Similarly, the term "homing molecule that homes to angiogenic vasculature" means a molecule that can bind specifically to a target molecule expressed in angiogenic vasculature. It is understood that a homing molecule can be a tumor homing molecule.

A homing molecule can bind to angiogenic vasculature in a tumor or in non-tumor tissue. A homing molecule that binds to both tumor and non-tumor angiogenic vasculature also can exhibit preferential binding to tumor or non-tumor tissues. For example, a tumor homing peptide such as an NGR peptide can accumulate preferentially in angiogenic vasculature of tumors as compared to non-tumor angiogenic vasculature.

The invention also provides a method of identifying a homing molecule that homes to angiogenic vasculature using substantially purified NGR receptor. The method includes the steps of contacting a substantially purified NGR receptor with one or more molecules and determining specific binding of a molecule to the NGR receptor, where the presence of specific binding identifies the molecule as a homing molecule that homes to angiogenic vasculature.

A method of the invention for identifying a homing molecule also can include the steps of administering an NGR binding molecule in vivo and determining binding of the NGR binding molecule to angiogenic vasculature. Thus, the invention provides methods for identifying homing molecules that bind to angiogenic vasculature in non-tumor tissue as well as homing molecules that home to angiogenic vasculature of a tumor. As disclosed herein, a substantially purified NGR receptor can be used to identify homing molecules that home to non-tumor neovascularized tissues of a subject, as well as to identify tumor homing molecules.

A homing molecule that homes to angiogenic vasculature or a tumor homing molecule that homes to angiogenic vasculature of a tumor is identified by screening one or more molecules, for example, a library of molecules. As used herein, the term "library" means a collection of molecules. A library can contain a few or a large number of different molecules, varying from about ten molecules to several billion molecules or more. If desired, a molecule can be linked to a tag, which can facilitate recovery or identification of the molecule. As disclosed herein, a homing molecule that homes to angiogenic vasculature can be identified by in vitro screening against a substantially purified NGR receptor.

As used herein, the term "molecule" is used broadly to mean an organic chemical such as a drug; a nucleic acid molecule such as an RNA, a cDNA or an oligonucleotide; a peptide, including a variant or modified peptide or peptide-like molecules, referred to herein as peptidomimetics, which mimic the activity of a peptide; or a protein such as an antibody or a growth factor receptor or a fragment thereof such as an Fv, single chain Fv(scFv), Fd or Fab fragment of an antibody, which contains a binding domain. For convenience, the term "peptide" is used broadly herein to mean peptides, proteins, fragments of proteins and the like, which can have, for example, a cyclic or linear conformation. A molecule also can be a non-naturally occurring molecule, which does not occur in nature, but is produced as a result of in vitro methods, or can be a naturally occurring molecule such as a protein or fragment thereof expressed from a cDNA library or a peptidomimetic.

A molecule to be screened against a substantially purified NGR receptor according to a method of the invention can be a "peptidomimetic," which is used broadly to mean a peptide-like molecule that has the binding activity of a tumor homing peptide, such as a peptidomimetic analog of an NGR peptide. Thus, peptidomimetics, including chemically modified peptides, peptide-like molecules containing non-naturally occurring amino acids, peptoids and the like, and, in particular, peptidomimetics of an NGR containing peptide, can be screened for the ability to specifically bind an NGR receptor, and thus, for activity in homing to angiogenic vasculature (see, for example, "Burger's Medicinal Chemistry and Drug Discovery" 5th ed., vols. 1 to 3 (ed. M. E. Wolff; Wiley Interscience 1995), which is incorporated herein by reference). Peptidomimetics provide various advantages over a peptide, for example, increased stability during passage through the digestive tract and, therefore, are advantageously used for oral administration.

Collections or libraries of peptidomimetics are well known in the art, for example, databases that contain libraries of potential peptidomimetics. For example, the Cambridge Structural Database contains a collection of greater than 300,000 compounds that have known crystal structures (Allen et al., *Acta Crystallogr.* Section B, 35:2331 (1979)). This structural depository is continually updated as new crystal structures are determined and can be screened for compounds having suitable shapes, for example, the same shape as a tumor homing molecule such as an NGR peptide, as well as potential geometrical and chemical complementarity to a target molecule bound by a tumor homing peptide. Where no crystal structure of a tumor homing peptide or a target molecule, which binds the tumor homing molecule, is available, a structure can be generated using, for example, the program CONCORD (Rusinko et al., *J. Chem. Inf. Comput. Sci.* 29:251 (1989)). Another database, the Available Chemicals Directory (Molecular Design Limited, Informations Systems; San Leandro Calif.), contains about 100,000 compounds that are commercially available and can be screened to identify a tumor homing molecule or a homing molecule that homes to angiogenic vasculature according to a method of the invention.

Methods for preparing libraries containing diverse populations of various types of molecules such as peptides, peptoids and peptidomimetics are well known in the art and various libraries are commercially available (see, for example, Ecker and Crooke, *Biotechnology* 13:351–360 (1995), and Blondelle et al., *Trends Anal. Chem.* 14:83–92 (1995), and the references cited therein, each of which is incorporated herein by reference; see, also, Goodman and Ro, *Peptidomimetics for Drug Design,* in "Burger's Medicinal Chemistry and Drug Discovery" Vol. 1 (ed. M. E. Wolff; John Wiley & Sons 1995), pages 803–861, and Gordon et al., *J. Med. Chem.* 37:1385–1401 (1994), each of which is incorporated herein by reference). Where a molecule is a peptide, protein or fragment thereof, the molecule can be produced in vitro directly or can be expressed from a nucleic acid, which can be produced in vitro. Methods of synthetic peptide and nucleic acid chemistry are well known in the art.

A library of molecules also can be produced, for example, by constructing a cDNA expression library from mRNA collected from a cell, tissue, organ or organism of interest. Methods for producing such libraries are well known in the art (see, for example, Sambrook et al., *Molecular Cloning: A laboratory manual* (Cold Spring Harbor Laboratory Press 1989), which is incorporated herein by reference). Preferably, a peptide encoded by the cDNA is expressed on the surface of a cell or a virus containing the cDNA. For example, cDNA can be cloned into a phage vector such as fuse 5 (Example I), wherein, upon expression, the encoded peptide is expressed as a fusion protein on the surface of the phage.

In addition, a library of molecules can comprise a library of nucleic acid molecules, which can be DNA or RNA or an analog thereof. Nucleic acid molecules that bind, for example, to a cell surface receptor are well known (see, for example, O'Connell et al., *Proc. Natl. Acad. Sci., USA* 93:5883–5887 (1996); Tuerk and Gold, *Science* 249:505–510 (1990); Gold et al., *Ann. Rev. Biochem.* 64:763–797 (1995), each of which is incorporated herein by reference). Thus, a library of nucleic acid molecules can be contacted with a substantially purified NGR receptor to identify a tumor homing molecule or a homing molecule that homes to angiogenic vasculature. If desired, the nucleic acid molecules can be nucleic acid analogs that, for example, are less susceptible to attack by nucleases (see, for example, Jelinek et al., *Biochemistry* 34:11363–11372 (1995); Latham et al., *Nucl. Acids Res.* 22:2817–2822 (1994); Tam et al., *Nucl. Acids Res.* 22:977–986 (1994); Reed et al., *Cancer Res.* 59:6565–6570 (1990), each of which is incorporated herein by reference).

Particularly useful libraries of molecules to be screened for specific binding to an NGR receptor and, therefore, for activity in homing to angiogenic vasculature, include phage display libraries. Such phage display libraries of molecules include secondary libraries expressing NGR in various contexts, including cyclic phage display peptide libraries such as $X_2CNGRCX_2$ (SEQ ID NO:222), $CX_2(C/X)NGR(C/X)X_2C$ (SEQ ID NO:223), and $CNGRCX_6$ (SEQ ID NO:224) (where "C" is cysteine and "X" is any amino acid; see Example X). A library of molecules to be screened also can be a library of antibodies or antibody fragments such as Fv, single chain Fv or Fab fragments; as disclosed in Example X, such a library can be, for example, a combinatorial scfv library prepared from rabbits immunized with human tumor xenografts. Such antibodies can bind to the same epitope recognized by the anti-CD13 antibodies F23 and MY7, or can bind to a different epitope.

One skilled in the art understands that a molecule that specifically binds a substantially purified NGR receptor can bind and modulate the activity of the NGR receptor, or can be inert with respect to its ability to affect the activity of an NGR receptor. As disclosed herein, for example, an NGR receptor is functionally important in angiogenesis. A molecule that specifically binds a substantially purified NGR receptor can be an agonist or an inhibitor of the receptor and, thus, can enhance or inhibit angiogenesis.

An inhibitor of an NGR receptor can be highly specific for the NGR receptor. For example, a specific inhibitor can be an antibody that binds with high specificity to an NGR receptor. The antibody can have the inherent property of inhibiting NGR receptor activity upon binding of the antibody. Alternatively, an antibody that is not inhibitory but binds specifically to an NGR receptor can be conjugated to a drug or target to generate a specific inhibitor. The antibody can be a monoclonal or polyclonal antibody or can be a functional antibody fragment such as a Fv, single chain Fv or Fab fragment.

Accordingly, monoclonal or polyclonal antibodies exhibiting specific binding to an NGR receptor can be generated by methods well known to those skilled in the art (Harlow and Lane, *Antibodies: A laboratory manual* (Cold Spring Harbor Laboratory Press 1988), which is incorporated herein by reference). Alternatively, libraries of functional antibody fragments, which can bind to an NGR receptor, can also be screened to identify a homing molecule that binds to an NGR receptor. For example, a combinatorial scfv library generated by immunizing with human tumor xenografts or a substantially purified NGR receptor can be screened for binding to an NGR receptor (see Example X).

In addition to inhibitors that are highly specific for an NGR receptor, inhibitors also can exhibit inhibitory activity to other molecules related but not identical to an NGR receptor. For example, aminopeptidase inhibitors can exhibit activity specific for an aminopeptidase or can exhibit inhibitory activity to several aminopeptidases. A homing molecule that binds to an NGR receptor and is an aminopeptidase inhibitor is particularly useful if the inhibitor exhibits preferential binding to an NGR receptor in a target neovascularized tissue.

Accordingly, libraries of molecules to be screened for activity in specifically binding a substantially purified NGR receptor include structural analogs of natural substrates of aminopeptidase as well as structural analogs of aminopeptidase inhibitors. Such libraries can include structural analogs of substrates such as Ala-PNA; Leu enkephalin; Met enkephalin or tuftsin (Xu et al., *Experimental Hematology* 25:521–529 (1997), which is incorporated herein by reference). Such libraries also can include structural analogs of aminopeptidase inhibitors, such as actinonin; amastatin; bestatin; 1,10-phenanthroline or o-phenanthroline; or 2,2'-dipyridyl; or analogs of Phe-Leu (Xu et al., supra, 1997). Such libraries can additionally include structural analogs of fumagillin (Sin et al., *Proc. Natl. Acad. Sci. USA* 94:6099–6103 (1997), which is incorporated herein by reference). From the above, it is understood that a molecule that specifically binds a substantially purified NGR receptor can be a naturally or non-naturally occurring structural analog of Phe-Leu.

In addition to screening phage and DNA libraries as described above, combinatorial chemistry libraries also can be screened in vitro using a substantially purified NGP receptor according to a method of the invention. Methods for generating combinatorial libraries are well known in the art as described, for example, in Gordon et al., *J. Med. Chem.* 37:1385–1401 (1994); Gallop et al., *J. Med. Chem.* 37:1203–1251 (1994); and Wilson and Czarnik, eds., *Combinatorial Chemistry* John Wiley & Sons, New York (1997), each of which is incorporated herein by reference).

The presence of a tumor homing molecule or a homing molecule that specifically binds an NGR receptor within a library of molecules can be identified using various methods well known in the art. Generally, the compounds in a library can be tested individually, for example, using high throughput screening. If desired, the individual compounds can be tagged to facilitate recovery or identification of the molecule. Such tagged libraries are useful for in vivo and in vitro screening.

As used herein, the term "tag" means a physical, chemical or biological moiety such as a plastic microbead, an oligonucleotide or a bacteriophage, respectively, that is linked to a molecule of the library. Methods for tagging a molecule are well known in the art (Hermanson, *Bioconlugate Techniques* (Academic Press 1996), which is incorporated herein by reference).

A specific tag can be particularly useful in the methods of the invention for identifying a tumor homing molecule or a homing molecule that homes to angiogenic vasculature. As used herein, the term "specific tag" means a physical, chemical or biological tag that is linked to a particular molecule in a library and is unique for that particular molecule. A specific tag is particularly useful if it is readily identifiable. A nucleotide sequence that is unique for a particular molecule of a library is an example of a specific tag. For example, the method of synthesizing peptides tagged with a unique nucleotide sequence provides a library of molecules, each containing a specific tag, such that upon determining the nucleotide sequence, the identity of the peptide is known (see Brenner and Lerner, *Proc. Natl. Acad. Sci., USA* 89:5381–5383 (1992), which is incorporated herein by reference). The use of a nucleotide sequence as a specific tag for a peptide or other type of molecule provides a simple means to identify the presence of the molecule in a sample because an extremely sensitive method such as PCR can be used to determine the nucleotide sequence of the specific tag, thereby identifying the sequence of the molecule linked thereto. Similarly, the nucleic acid sequence encoding a peptide expressed on a phage is another example of a specific tag, since sequencing of the specific tag identifies the amino acid sequence of the expressed peptide.

Identified tumor homing molecules are useful, for example, for targeting a desired moiety such as a drug, a toxin or a detectable label, which can be linked to the molecule, to a tumor. In addition, a tumor homing molecule is useful for identifying the target molecule, to which the homing molecule binds in the tumor. Once a target molecule has been identified, for example, an NGR receptor as disclosed herein, the target molecule can be used to identify additional tumor homing molecules.

The present invention also provides a method of directing a moiety to angiogenic vasculature of a tumor in a subject by administering to the subject a conjugate including a moiety linked to a tumor homing molecule that exhibits specific binding to an NGR receptor, whereby the conjugate is directed to angiogenic vasculature of a tumor. In a method of the invention, the tumor homing molecule can be, for example, a peptide containing the sequence NGR, and, if desired, can be part of a conjugate in which the moiety is a cytotoxic agent, drug or chemotherapeutic agent, for example, doxorubicin. A tumor homing peptide containing the sequence NGR can have, for example, the sequence CNGRCVSGCAGRC (SEQ ID NO:3), NGRAHA (SEQ ID NO:6), CVLNGRMEC (SEQ ID NO:7) or CNGRC (SEQ ID NO:8). In a method of the invention for directing a moiety to angiogenic vasculature of a tumor in a subject, the tumor homing molecule also can be, for example, an aminopeptidase inhibitor such as bestatin, o-phenanthroline, actinonin, amastatin, 2,2'-dipyridyl or fumagillin and can be linked, if desired, to a doxorubicin moiety.

The present invention additionally provides a method of inhibiting angiogenesis in a tumor of a subject by administering to the subject a conjugate including a moiety linked to a tumor homing molecule that exhibits specific binding to an NGR receptor, whereby the conjugate is directed to angiogenic vasculature of a tumor. In a method of the invention, the tumor homing molecule can be, for example, a peptide containing the sequence NGR, and, if desired, can be part of a conjugate in which the moiety is a cytotoxic agent, drug or chemotherapeutic agent, for example, doxorubicin. A tumor homing peptide containing the sequence NGR can have, for example, the sequence CNGRCVSGCAGRC (SEQ ID NO:3), NGRAHA (SEQ ID NO:6), CVLNGRMEC (SEQ ID NO:7) or CNGRC (SEQ ID NO:8). In a method of the invention for directing a moiety to angiogenic vasculature of a tumor in a subject, the tumor homing molecule also can be, for example, an aminopeptidase inhibitor such as bestatin, o-phenanthroline, actinonin, amastatin, 2,2'-dipyridyl or fumagillin and can be linked, if desired, to a doxorubicin moiety.

The invention also provides a method of inhibiting angiogenesis in a non-tumor tissue. The method includes administering a conjugate including a moiety linked to a homing molecule that exhibits specific binding to an NGR receptor, whereby the conjugate is directed to angiogenic vasculature of a non-tumor tissue. Inhibiting angiogenesis in a non-tumor tissue is useful, for example, for treating diseases involving neovascularized tissue such as retinal neovascularization in macular degeneration and diabetes and neovascularization in rheumatoid arthritis synovium.

As disclosed, tumor homing molecules can be conjugated to moieties such as a drug or toxin in order to target the drug or toxin to a tumor. A tumor homing molecule such as one of the NGR containing peptides CNGRCVSGCAGRC (SEQ ID NO:3), NGRAHA (SEQ ID NO:6), CVLNGRMEC (SEQ ID NO:7), or CNGRC (SEQ ID NO:8) can be used to direct a moiety to angiogenic vasculature. Additional tumor homing molecules that bind to the NCGR receptor identified in vivo or in vitro as described above also can be used to direct a moiety to the angiogenic vasculature of a tumor.

In addition to tumor homing molecules that contain NGR, other tumor homing molecules that specifically bind to the NGR receptor are also useful for targeting angiogenic vasculature. As described below, the NGR receptor exhibits aminopeptidase activity, and the aminopeptidase activity can be inhibited by known inhibitors such as bestatin, o-phenanthroline and actinonin. Therefore, in addition to NGR containing peptides, other molecules that bind to the NGR receptor can also function as tumor homing molecules. For example, a molecule that functions as an aminopeptidase inhibitor such as bestatin, o-phenanthroline, actinonin, amastatin, 2,2'-dipyridyl or fumagillin can be used as conjugates with a drug or toxin to home to angiogenic vasculature.

The invention additionally provides a method of directing a moiety to angiogenic vasculature in a subject by administering to the subject a conjugate comprising a moiety linked to a homing molecule that exhibits specific binding to an NGR receptor, where the moiety is directed to angiogenic vasculature. Thus, the invention provides a method of directing a conjugate, for example, of a drug or toxin, to angiogenic vasculature of non-tumor tissue. The targeting of a conjugate to angiogenic vasculature of non-tumor tissue is useful, for example, for treating diseases involving neovascularized tissue such as retinal neovascularization in macular degeneration and diabetes and neovascularization in rheumatoid arthritis synovium.

A variety of moieties can be directed to angiogenic vasculature in a method of the invention. As used herein, the term "moiety" is used broadly to mean a physical, chemical, or biological material that is linked to a tumor homing molecule for the purpose of being targeted in vivo to a tumor or to angiogenic vasculature expressing a target molecule recognized by the tumor homing molecule. In particular, a moiety is a biologically useful moiety such as therapeutic moiety, a diagnostic moiety or a drug delivery vehicle. Thus, a moiety can be a therapeutic agent, for example, a cancer chemotherapeutic agent such as doxorubicin, which, when linked to a tumor homing molecule, provides a conjugate useful for treating a cancer in a subject. In addition, a moiety can be a drug delivery vehicle such as a chambered microdevice, a cell, a liposome or a virus, which can contain an agent such as a drug or a nucleic acid.

A moiety also can be a molecule such as a polypeptide or nucleic acid, to which a tumor homing molecule is grafted for the purpose of directing the polypeptide or nucleic acid to a selected tumor (Smith et al., *J. Biol. Chem.* 269:32788–32795 (1994); Goldman et al., *Cancer Res.* 15:1447–1451 (1997), each of which is incorporated herein by reference). For example, a peptide tumor homing molecule can be expressed as a fusion protein with a desired polypeptide such that the peptide targets the grafted polypeptide to a selected tumor. Such a desired polypeptide, which is grafted to the tumor homing peptide, can be a polypeptide involved in initiating a cell death pathway, for example, caspase 8, thus providing a means to direct caspase 8 to a tumor, where it can induce apoptosis of the tumor cells or of the vasculature supplying the tumor. A tumor homing peptide also can be grafted to a polypeptide expressed by a virus, for example, the adenovirus penton base coat protein, thus providing a means to target a virus to a tumor (Wickham et al., *Gene Ther.* 2:750–756 (1995); Weitzman et al., In: "Gene Therapy and Vector Systems" 2:17–25 (1997), each of which is incorporated herein by reference; see, also, Example III). Such a grafted virus can contain an exogenous gene useful in a method of gene therapy. Accordingly, the invention provides compositions of matter comprising a tumor homing molecule/moiety conjugate.

A moiety can be a detectable label such a radiolabel or can be a cytotoxic agent, including a toxin such as ricin or a drug such as a chemotherapeutic agent or can be a physical, chemical or biological material such as a liposome, microcapsule, micropump or other chambered microdevice, which can be used, for example, as a drug delivery system. Generally, such microdevices, should be nontoxic and, if desired, biodegradable. Various moieties, including microcapsules, which can contain an agent, and methods for linking a moiety, including a chambered microdevice, to a molecule of the invention are well known in the art and commercially available (see, for example, "Remington's Pharmaceutical Sciences" 18th ed. (Mack Publishing Co.

1990), chapters 89–91; Harlow and Lane, *Antibodies: A laboratory manual* (Cold Spring Harbor Laboratory Press 1988), each of which is incorporated herein by reference; see, also, Hermanson, supra, 1996).

As disclosed herein, a moiety can be, for example, a cancer chemotherapeutic agent linked to a tumor homing molecule to produce a tumor homing molecule/moiety conjugate. Cytotoxic chemotherapy is the basis of the systemic treatment of disseminated malignant tumors. However, a major limitation of the currently used chemotherapeutic agents is that these drugs have the narrowest therapeutic index in all of medicine. As such, the dose of cancer chemotherapeutic agents generally is limited by undesirable toxicity to the patient being treated. Thus, the ability of tumor homing peptides of the invention to target drugs into tumors was examined. As disclosed herein, the linking of a cancer chemotherapeutic agent, doxorubicin, to a tumor homing molecule reduced the systemic toxicity of the doxorubicin and enhanced anti-tumor activity of the agent (see Examples VIII and XV).

A conjugate of the invention is exemplified herein by doxorubicin linked to various tumor homing peptides (see Examples VII and VIII). In view of the exemplified method of linking doxorubicin to various tumor homing peptides and the disclosed efficacy of such conjugates of the invention, the skilled artisan will recognize that various other chemotherapeutic agents also can be linked to a tumor homing molecule to make a conjugate of the invention. Cancer chemotherapeutic agents have been linked to antibodies, for example, for the purpose of targeting the agents to cells such as tumor cells that express the antigen recognized by the antibodies. In addition, in such antibody/drug conjugates, the agent can maintain its therapeutic function and the antibody can maintain its antigen binding specificity. For example, the anthracyclin, doxorubicin, has been linked to antibodies and the antibody/doxorubicin conjugates have been therapeutically effective in treating tumors (Sivam et al., *Cancer Res.* 55:2352–2356 (1995); Lau et al., *Bioorg. Med. Chem.* 3:1299–1304 (1995); Shih et al., *Cancer Immunol. Immunother.* 38:92–98 (1994)). Similarly, other anthracyclins, including idarubicin and daunorubicin, have been chemically conjugated to antibodies, which have delivered effective doses of the agents to tumors (Rowland et al., *Cancer Immunol. Immunother.* 37:195–202 (1993); Aboud-Pirak et al., *Biochem. Pharmacol.* 38:641–648 (1989)).

In addition to the anthracyclins, alkylating agents such as melphalan and chlorambucil have been linked to antibodies to produce therapeutically effective conjugates (Rowland et al., supra, 1994; Smyth et al., *Immunol. Cell Biol.* 65:315–321 (1987)), as have vinca alkaloids such as vindesine and vinblastine (Aboud-Pirak et al., supra, 1989; Starling et al., *Bioconj. Chem.* 3:315–322 (1992)). Similarly, conjugates of antibodies and antimetabolites such as 5-fluorouracil, 5-fluorouridine and derivatives thereof have been effective in treating tumors (Krauer et al., *Cancer Res.* 52:132–137 (1992); Henn et al., *J. Med. Chem.* 36:1570–1579 (1993)). Other chemotherapeutic agents, including cis-platinum (Schechter et al., *Int. J. Cancer* 48:167–172 (1991)), methotrexate (Shawler et al., *J. Biol. Resp. Mod.* 7:608–618 (1988); Fitzpatrick and Garnett, *Anticancer Drug Des.* 10:11–24 (1995)) and mitomycin-C (Dillman et al., *Mol. Biother.* 1:250–255 (1989)) also are therapeutically effective when administered as conjugates with various different antibodies.

The results obtained using antibody/drug conjugates demonstrate that a chemotherapeutic agent can be linked to an antibody to produce a conjugate that maintains the antigen binding specificity of the antibody and the therapeutic function of the agent. As disclosed herein, a conjugate comprising doxorubicin and a tumor homing peptide maintains the tumor homing specificity of the tumor homing peptide as well as the therapeutic efficacy of the chemotherapeutic agent (see Examples VIII and XV). Such results are remarkable, since, in the doxorubicin/CNGRC (SEQ ID NO:8) conjugate, for example, the doxorubicin component has only a slightly lower molecular weight than the peptide and comprises about 46% of the molecular weight of the conjugate.

Since the moiety component of a tumor homing molecule/moiety conjugate can comprise a substantial portion of the conjugate without adversely affecting the ability of the tumor homing molecule to home to a tumor, additional components can be included as part of the conjugate, if desired. For example, in some cases, it can be desirable to utilize an oligopeptide spacer between a tumor homing peptide and the moiety (Fitzpatrick and Garnett, *Anticancer Drug Des.* 10:1–9 (1995)). In this way, panels of moiety/spacer complexes can be constructed, in which a common spacer is linked to various different moieties. Such panels of moiety/spacer conjugates can facilitate linkage of the moiety to a tumor homing molecule such as a tumor homing peptide of choice.

Doxorubicin is one of the most commonly used cancer chemotherapeutic agents and, particularly, is used for treating breast cancer (Stewart and Ratain, In: "Cancer: Principles and practice of oncology" 5th ed., chap. 19 (eds. DeVita, Jr., et al.; J. P. Lippincott 1997); Harris et al., In "Cancer: Principles and practice of oncology," supra, 1997). In addition, doxorubicin has anti-angiogenic activity (Folkman, supra, 1997; Steiner, In "Angiogenesis: Key principles-Science, technology and medicine," pp. 449–454 (eds. Steiner et al.; Birkhauser Verlag, 1992)), which can contribute to its effectiveness in treating cancer. Thus, treatment of human breast cancer xenografts in mice using doxorubicin was selected as a model for exemplifying the present invention.

As used herein, the term "tumor" means a mass of cells that are characterized, at least in part, by containing angiogenic vasculature. The term "tumorr" is used broadly to include the tumor parenchymal cells as well as the supporting stroma, including the angiogenic blood vessels that infiltrate the tumor parenchymal cell mass. Although a tumor generally is a malignant tumor, i.e., a "cancer," a tumor also can be nonmalignant, provided that neovascularization is associated with the tumor. The term "normal" or "nontumor" tissue is used to refer to tissue that is not a "tumor." As disclosed herein, a tumor homing molecule can be identified based on its ability to home a tumor, but not to a corresponding nontumor tissue.

As used herein, the term "corresponding," when used in reference to tumors or tissues or both, means that two or more tumors, or two or more tissues, or a tumor and a tissue are of the same histologic type. The skilled artisan will recognize that the histologic type of a tissue is a function of the cells comprising the tissue. Thus, the artisan will recognize, for example, that a nontumor tissue corresponding to a breast tumor is normal breast tissue, whereas a nontumor tissue corresponding to a melanoma is skin, which contains melanocytes. Furthermore, for purposes of the invention, it is recognized that a tumor homing molecule can bind specifically to a target molecule expressed by the vasculature in a tumor, which generally contains blood vessels undergoing neovascularization, in which case a tissue corresponding to the tumor would comprise nontumor tissue containing blood vessels that are not undergoing active angiogenesis.

The term "corresponding" also is used herein in reference to the evolutionarily conserved nature of target molecules, which are expressed in a tumor, for example, in a mouse as compared to a human. Thus, reference to the corresponding target molecules in mouse tumor vasculature as compared, for example, to human vasculature, means target molecules having a similar function, particularly the ability to specifically bind a tumor homing molecule.

Further provided herein is a method of imaging the angiogenic vasculature of a tumor or other pathological tissue in a subject by administering to the subject a conjugate having a detectable moiety linked to a molecule that exhibits specific binding to an NGR receptor, whereby the conjugate selectively binds the angiogenic vasculature, and detecting the conjugate. A detectable moiety for imaging angiogenic vasculature can be, for example, a radionuclide. A useful homing molecule for imaging angiogenic vasculature can be, for example, a peptide containing the sequence NGR, such as a peptide containing the sequence CNGRCVSG-CAGRC (SEQ ID NO:3), NGRAHA (SEQ ID NO:6), CVLNGRMEC (SEQ ID NO:7) or CNGRC (SEQ ID NO:8). A tumor homing molecule for imaging angiogenic vasculature also can be, for example, an aminopeptidase inhibitor such as bestatin, o-phenanthroline, actinonin, amastatin, 2,2'-dipyridyl or fumagillin. Methods for coupling detectable moieties to a tumor homing molecule are described below. Thus, the identification of tumor homing molecules that bind an NGR receptor as described herein provides reagents useful for imaging tumors for diagnostic and prognostic purposes.

The invention also provides a substantially purified target molecule, comprising an NGR receptor that binds a peptide comprising the sequence NGR, provided that the NGR receptor does not have the amino acid sequence of CD13/aminopeptidase N (SEQ ID NO:201). Accordingly, an NGR receptor that has one or more modifications of amino acids relative to the sequence of CD13/aminopeptidase (SEQ ID NO:201), for example, deletions, insertions or substitutions, including conservative and non-conservative amino acid substitutions, and that specifically binds the sequence NGR is provided by the invention.

The present invention relates to molecules that selectively home to tumors. For example, the invention provides tumor homing peptides such as the peptides CGRECPRLCQSSC (SEQ ID NO:2) and CNGRCVSGCAGRC (SEQ ID NO:3), which were identified based on their ability to home to a breast carcinoma, and the peptide CLSGSLSC (SEQ ID NO:4, which was identified based on its ability to home to a melanoma. Such tumor homing peptides were identified using in vivo panning (see U.S. Pat. No. 5,622,699, issued Apr. 22, 1997; Pasqualini and Ruoslahti, *Nature* 380:364–366 (1996), each of which is incorporated herein by reference).

The disclosed tumor homing peptides were identified based on their homing to various particular tumors. For example, in vivo panning was performed using a mouse bearing a human breast carcinoma xenograft and peptides that homed to the breast tumor were identified. However, as disclosed herein, such tumor homing peptides generally homed to other types of tumors, including a mouse melanoma and a human Kaposi's sarcoma. Thus, while the tumor homing peptide CNGRCVSGCAGRC (SEQ ID NO:3) was identified by its ability to home in vivo to a breast tumor, this peptide also homed in vivo to a melanoma and to a Kaposi's sarcoma, but not to nontumor tissues.

Similarly, the tumor homing peptide CLSGSLSC (SEQ ID NO:4) was identified based on its homing to melanoma. However, further examination of this peptide revealed that it also homed to a breast tumor and to Kaposi's sarcoma. Immunohistological analysis revealed that such tumor homing peptides initially are associated with the vasculature of the various tumors, although at later time the molecules are associated with tumor parenchymal cells. Thus, the general tumor homing ability of a tumor homing molecule of the invention is due, at least in part, to the ability of the tumor homing molecules to target angiogenic vasculature associated with a tumor. These results indicate that specific target molecules are expressed by the cells comprising the vasculature in a tumor as compared to the cell surface molecule expressed by vasculature in nontumor tissues. Using methods as disclosed herein, the artisan readily can determine whether a tumor homing molecule homes generally to the angiogenic vasculature associated with a tumor or homes specifically to a particular type of tumor cell.

Identified tumor homing molecules are useful, for example, for targeting a desired moiety such as a drug, a toxin or a detectable label, which can be linked to the molecule, to a tumor. Thus, the invention provides tumor homing molecule/moiety conjugates, which are useful for targeting the moiety to a tumor. Accordingly, the invention also provides methods of targeting a moiety to a tumor and, therefore, methods of reducing the severity of a tumor and of treating a subject having a cancer (see Examples VIII and XV). In addition, a tumor homing molecule is useful for identifying the target molecule, to which the homing molecule binds in the tumor.

Methods for identifying a tumor homing molecule within a library of molecules have been described hereinabove. Generally, the presence of a tumor homing molecule in a tumor is identified based on one or more characteristics common to the molecules present in the library, then the structure of a particular tumor homing molecule is identified. For example, a highly sensitive detection method such as mass spectrometry, either alone or in combination with a method such as gas chromatography, can be used to identify tumor homing molecules in a tumor. Thus, where a library comprises diverse molecules based generally on the structure of an organic molecule such as a drug, a tumor homing molecule can be identified by determining the presence of a parent peak for the particular molecule.

If desired, the tumor can be collected, then processed using a method such as HPLC, which can provide a fraction enriched in molecules having a defined range of molecular weights or polar or nonpolar characteristics or the like, depending, for example, on the general characteristics of the molecules comprising the library. Conditions for HPLC will depend on the chemistry of the particular molecule and are well known to those skilled in the art. Similarly, methods for bulk removal of potentially interfering cellular materials such as DNA, RNA, proteins, lipids or carbohydrates are well known in the art, as are methods for enriching a fraction containing an organic molecule using, for example, methods of selective extraction. Where a library comprises a population of diverse organic chemical molecules, each linked to a specific oligonucleotide tag, such that the specific molecule can be identified by determining the oligonucleotide sequence using polymerase chain reaction (PCR), genomic DNA can be removed from the sample of the collected tumor in order to reduce the potential for background PCR reactions. In addition, a library can comprise a population of diverse molecules such as organic chemical molecules, each linked to a common, shared tag. Based on the presence and properties of the shared tag, molecules of the library that selectively home to a tumor can be substantially isolated from a sample of the tumor. These and other methods can be useful for enriching a sample of a collected tumor for the particular tumor homing molecule, thereby removing potentially contaminating materials from the collected tumor sample and increasing the sensitivity of detecting a molecule.

Evidence provided herein indicates that a sufficient number of tumor homing molecules selectively homes to a tumor during in vivo panning such that the molecules readily can be identified. For example, various independent phage expressing the same peptide were identified in tumors formed from implanted human breast cancer cells (Table 1), from mouse melanoma cells (Table 2) or from human Kaposi's sarcoma cells (Table 3).

Although a substantial fraction of the identified tumor homing molecules have the same structure, the peptide inserts of only a small number of isolated phage were determined. It should be recognized, however, that hundreds of thousands to millions of phage expressing organ homing peptides have been recovered following in vivo pannings for organ homing molecules (see, for example, U.S. Pat. No. 5,622,699; Pasqualini and Ruoslahti, supra, 1996). These results indicate that specific tumor homing molecules will be present in substantial numbers in a tumor following in vivo homing, thereby increasing the ease with which the molecules can be identified.

Ease of identification of a tumor homing molecule, particularly an untagged molecule, depends on various factors, including the presence of potentially contaminating background cellular material. Thus, where the tumor homing molecule is an untagged peptide, a larger number must home to the tumor in order to identify the specific peptides against the background of cellular protein. In contrast, a much smaller number of an untagged organic chemical homing molecule such as a drug is identifiable because such molecules normally are absent from or present in only small numbers in the body. In such a case, a highly sensitive method such as mass spectrometry can be used to identify a tumor homing molecule. The skilled artisan will recognize that the method of identifying a molecule will depend, in part, on the chemistry of the particular molecule.

Several rounds of in vivo homing can be performed with partial purification of the library molecule by extracting the target tissue between rounds of screening. To ensure the recovery of an adequate number of homing molecules after the final round of screening, material can be pooled from several animals used in an earlier round of screening and injected into a smaller number of animals in the subsequent rounds of screening. Alternatively, a larger animal can be used in the earlier rounds than in the subsequent rounds of screening. The feasibility of screening without intervening steps has been demonstrated with phage.

Where a tumor homing molecule is a nucleic acid or is tagged with a nucleic acid, an assay such as PCR can be particularly useful for identifying the presence of the molecule because, in principle, PCR can detect the presence of a single nucleic acid molecule (see, for example, Erlich, *PCR Technology: Principles and Applications for DNA Amplification* (Stockton Press 1989), which is incorporated herein by reference). Preliminary studies have demonstrated that, following intravenous injection of 10 ng of an approximately 6000 base pair plasmid into a mouse and 2 minutes in the circulation, the plasmid was detectable by PCR in a sample of lung. These results indicate that nucleic acids are sufficiently stable when administered into the circulation such that in vivo panning can be used to identify nucleic acid molecules that selectively home to a tumor.

The molecules of a library can be tagged, which can facilitate recovery or identification of the molecule. As used herein, the term "tag" means a physical, chemical or biological moiety such as a plastic microbead, an oligonucleotide or a bacteriophage, respectively, that is linked to a molecule of the library. Methods for tagging a molecule are well known in the art (Hermanson, supra (1996)), which is incorporated herein by reference).

A tag, which can be a shared tag or a specific tag, can be useful for identifying the presence or structure of a tumor homing molecule of a library. As used herein, the term "shared tag" means a physical, chemical or biological moiety that is common to each molecule in a library. Biotin, for example, can be a shared tag that is linked to each molecule in a library. A shared tag can be useful to identify the presence of a molecule of the library in a sample and also can be useful to substantially isolate the molecules from a sample. For example, where the shared tag is biotin, the biotin-tagged molecules in a library can be substantially isolated by binding to streptavidin or their presence can be identified by binding with a labeled streptavidin. Where a library is a phage display library, the phage that express the peptides are another example of a shared tag, since each peptide of the library is linked to a phage. In addition, a peptide such as the hemaglutinin antigen can be a shared tag that is linked to each molecule in a library, thereby allowing the use of an antibody specific for the hemaglutinin antigen to substantially isolate molecules of the library from a sample of a selected tumor.

A shared tag also can be a nucleic acid sequence that can be useful to identify the presence of molecules of the library in a sample or to substantially isolate molecules of a library from a sample. For example, each of the molecules of a library can be linked to the same selected nucleotide sequence, which constitutes the shared tag. An affinity column containing a nucleotide sequence that is complementary to the shared tag then can be used to hybridize molecules of the library containing the shared tag, thus substantially isolating the molecules from a tumor sample. A nucleotide sequence complementary to a portion of the shared nucleotide sequence tag also can be used as a PCR primer such that the presence of molecules containing the shared tag can be identified in a sample by PCR.

The molecules of a library can be tagged, which can facilitate recovery or identification of the molecule. As used herein, the term "tag" means a physical, chemical or biological moiety such as a plastic microbead, an oligonucleotide or a bacteriophage, respectively, that is linked to a molecule of the library. Methods for tagging a molecule are well known in the art (Hermanson, *Bioconjugate Techniques* (Academic Press 1996), which is incorporated herein by reference).

A specific tag can be particularly useful in the methods of the invention for identifying a tumor homing molecule that homes to angiogenic vasculature. As used herein, the term "specific tag" means a physical, chemical or biological tag that is linked to a particular molecule in a library and is unique for that particular molecule. A specific tag is particularly useful if it is readily identifiable. A nucleotide sequence that is unique for a particular molecule of a library is an example of a specific tag. For example, the method of synthesizing peptides tagged with a unique nucleotide sequence provides a library of molecules, each containing a specific tag, such that upon determining the nucleotide sequence, the identity of the peptide is known (see Brenner and Lerner, supra (1992), which is incorporated herein by reference). The use of a nucleotide sequence as a specific tag for a peptide or other type of molecule provides a simple means to identify the presence of the molecule in a sample because an extremely sensitive method such as PCR can be used to determine the nucleotide sequence of the specific tag, thereby identifying the sequence of the molecule linked thereto. Similarly, the nucleic acid sequence encoding a peptide expressed on a phage is another example of a specific tag, since sequencing of the specific tag identifies the amino acid sequence of the expressed peptide.

The presence of a shared tag or a specific tag can provide a means to identify or recover a tumor homing molecule of the invention following in vivo panning. In addition, the combination of a shared tag and specific tag can be particularly useful for identifying a tumor homing molecule. For example, a library of peptides can be prepared such that each is linked to a specific nucleotide sequence tag (see, for example, Brenner and Lerner, supra, 1992), wherein each specific nucleotide sequence tag has incorporated therein a shared tag such as biotin. Upon homing to a tumor, the particular tumor homing peptides can be substantially isolated from a sample of the tumor based on the shared tag and the specific peptides can be identified, for example, by PCR of the specific tag (see Erlich, supra, 1989).

A tag also can serve as a support. As used herein, the term "support" means a tag having a defined surface to which a molecule can be attached. In general, a tag useful as a support is a shared tag. For example, a support can be a biological tag such as a virus or virus-like particle such as a bacteriophage ("phage"); a bacterium such as *E. coli;* or a eukaryotic cell such as a yeast, insect or mammalian cell; or can be a physical tag such as a liposome or a microbead, which can be composed of a plastic, agarose, gelatin or other biological or inert material. If desired, a shared tag useful as a support can have linked thereto a specific tag. Thus, the phage display libraries used in the exemplified methods can be considered to consist of the phage, which is a shared tag that also is a support, and the nucleic acid sequence encoding the expressed peptide, the nucleic acid sequence being a specific tag.

In general, a support should have a diameter less than about 10 μm to about 50 μm in its shortest dimension, such that the support can pass relatively unhindered through the capillary beds present in the subject and not occlude circulation. In addition, a support can be nontoxic, so that it does not perturb the normal expression of cell surface molecules or normal physiology of the subject, and biodegradable, particularly where the subject used for in vivo panning is not sacrificed to collect a selected tumor.

Where a molecule is linked to a support, the tagged molecule comprises the molecule attached to the surface of the support, such that the part of the molecule suspected of being able to interact with a target molecule in a cell in the subject is positioned so as to be able to participate in the interaction. For example, where the tumor homing molecule is suspected of being a ligand for a growth factor receptor, the binding portion of the molecule attached to a support is positioned so it can interact with the growth factor receptor on a cell in the tumor. If desired, an appropriate spacer molecule can be positioned between the molecule and the support such that the ability of the potential tumor homing molecule to interact with the target molecule is not hindered.

A spacer molecule also can contain a reactive group, which provides a convenient and efficient means of linking a molecule to a support and, if desired, can contain a tag, which can facilitate recovery or identification of the molecule (see Hermanson, supra, 1996).

As exemplified herein, a peptide suspected of being able to home to a selected tumor such as a breast carcinoma or a melanoma was expressed as the N-terminus of a fusion protein, wherein the C-terminus consisted of a phage coat protein. Upon expression of the fusion protein, the C-terminal coat protein linked the fusion protein to the surface of a phage such that the N-terminal peptide was in a position to interact with a target molecule in the tumor. Thus, a molecule having a shared tag was formed by the linking of a peptide to a phage, wherein the phage provided a biological support, the peptide molecule was linked as a fusion protein, the phage-encoded portion of the fusion protein acted as a spacer molecule, and the nucleic acid encoding the peptide provided a specific tag allowing identification of a tumor homing peptide.

As used herein, the term "in vivo panning," when used in reference to the identification of a tumor homing molecule, means a method of screening a library by administering the library to a subject and identifying a molecule that selectively homes to a tumor in the subject (see U.S. Pat. No. 5,622,699). The term "administering to a subject", when used in referring to a library of molecules or a portion of such a library, is used in its broadest sense to mean that the library is delivered to a tumor in the subject, which, generally, is a vertebrate, particularly a mammal such as a human.

A library can be administered to a subject, for example, by injecting the library into the circulation of the subject such that the molecules pass through the tumor; after an appropriate period of time, circulation is terminated by sacrificing the subject or by removing a sample of the tumor (Example I; see, also, U.S. Pat. No. 5,622,699; Pasqualini and Ruoslahti, supra, 1996). Alternatively, a cannula can be inserted into a blood vessel in the subject, such that the library is administered by perfusion for an appropriate period of time, after which the library can be removed from the circulation through the cannula or the subject can be sacrificed to collect the tumor, or the tumor can be sampled, to terminate circulation. Similarly, a library can be shunted through one or a few organs, including the tumor, by cannulation of the appropriate blood vessels in the subject. It is recognized that a library also can be administered to an isolated perfused tumor. Such panning in an isolated perfused tumor can be useful to identify molecules that bind to the tumor and, if desired, can be used as an initial screening of a library.

The use of in vivo panning to identify tumor homing molecules is exemplified herein by screening a phage peptide display library in tumor-bearing mice and identifying specific peptides that selectively homed to a breast tumor or to a melanoma tumor (Example I). However, phage libraries that display protein receptor molecules, including, for example, an antibody or an antigen binding fragment of an antibody such an Fv, Fd or Fab fragment; a hormone receptor such as a growth factor receptor; or a cell adhesion receptor such as an integrin or a selectin also can be used to practice the invention. Variants of such molecules can be constructed using well known methods such as random, site-directed or codon based mutagenesis (see Huse, U.S. Pat. No. 5,264,563, issued Nov. 23, 1993, which is incorporated herein by reference) and, if desired, peptides can be chemically modified following expression of the phage but prior to administration to the subject. Thus, various types of phage display libraries can be screened by in vivo panning.

Phage display technology provides a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993, which is incorporated herein by reference) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

Similarly, Smith and Scott (*Meth. Enzymol.* 217:228–257 (1993); see, also, Scott and Smith, *Science* 249: 386–390 (1990), each of which is incorporated herein by reference) describe methods of producing phage peptide display libraries, including vectors and methods of diversifying the population of peptides that are expressed (see, also, Huse, WO 91/07141 and WO 91/07149, each of which is incorporated herein by reference; see, also, Example I). Phage display technology can be particularly powerful when used, for example, with a codon based mutagenesis method, which can be used to produce random peptides or randomly or desirably biased peptides (Huse, U.S. Pat. No. 5,264,563, supra, 1993). These or other well known methods can be used to produce a phage display library, which can be subjected to the in vivo panning method of the invention in order to identify a peptide that homes to a tumor.

In addition to screening a phage display library, in vivo panning can be used to screen various other types of libraries, including, for example, an RNA or DNA library or a chemical library. If desired, the tumor homing molecule can be tagged, which can facilitate recovery of the molecule from the tumor or identification of the molecule in the tumor. For example, where a library of organic molecules, each containing a shared tag, is screened, the tag can be a moiety such as biotin, which can be linked directly to the molecule or can be linked to a support containing the molecules. Biotin provides a shared tag useful for recovering the molecule from a selected tumor sample using an avidin or streptavidin affinity matrix. In addition, a molecule or a support containing a molecule can be linked to a hapten such as 4-ethoxy-methylene-2-phenyl-2-oxazoline-5-one (phOx), which can be bound by an anti-phOx antibody linked to a magnetic bead as a means to recover the molecule. Methods for purifying biotin or phOx labeled conjugates are known in the art and the materials for performing these procedures are commercially available (e.g., Invitrogen, La Jolla Calif.; and Promega Corp., Madison Wis.). In the case where a phage library is screened, the phage can be recovered using methods as disclosed in Example I.

In vivo panning provides a method for directly identifying molecules that can selectively home to a tumor. As used herein, the term "home" or "selectively home" means that a particular molecule binds relatively specifically to a target molecule present in the tumor following administration to a subject. In general, selective homing is characterized, in part, by detecting at least a two-fold (2×) greater specific binding of the molecule to the tumor as compared to a control organ or tissue.

It should be recognized that, in some cases, a molecule can localize nonspecifically to an organ or tissue containing a tumor. For example, in vivo panning of a phage display library can result in high background in organs such as liver and spleen, which contain a marked component of the reticuloendothelial system (RES). Thus, where a tumor is present, for example, in the liver, nonspecific binding of molecules due to uptake by the RES can make identifying a tumor homing molecule more difficult.

Selective homing can be distinguished from nonspecific binding, however, by detecting differences in the abilities of different individual phage to home to a tumor. For example, selective homing can be identified by combining a putative tumor homing molecule such as a peptide expressed on a phage with a large excess of non-infective phage or with about a five-fold excess of phage expressing unselected peptides, injecting the mixture into a subject and collecting a sample of the tumor. In the latter case, for example, provided the number of injected phage expressing tumor homing peptide is sufficiently low so as to be nonsaturating for the target molecule, a determination that greater than about 20% of the phage in the tumor express the putative tumor homing molecule is demonstrative evidence that the peptide expressed by the phage is a specific tumor homing molecule. In addition, nonspecific localization can be distinguished from selective homing by performing competition experiments using, for example, phage expressing a putative tumor homing peptide in combination with an excess amount of the "free" peptide (Example V).

In addition, various methods can be used to prevent nonspecific binding of a molecule to an organ containing a component of the RES. For example, a molecule that homes selectively to a tumor present in an organ containing a component of the RES can be obtained by first blocking the RES using, for example, polystyrene latex particles or dextran sulfate (see Kalin et al., *Nucl. Med. Biol.* 20:171–174 (1993); Illum et al., *J. Pharm. Sci.* 75:16–22 (1986); Takeya et al., *J. Gen. Microbiol.* 100:373–379 (1977), each of which is incorporated herein by reference), then administering the library to the subject. For example, pre-administration of dextran sulfate 500 or polystyrene microspheres prior to administration of a test substance has been used to block nonspecific uptake of the test substance by Kupffer cells, which are the RES component of the liver (Illum et al., supra, 1986). Similarly, nonspecific uptake of agents by the RES has been blocked using carbon particles or silica (Takeya et al., supra, 1977) or a gelatine colloid (Kalin et al., supra, 1993). Thus, various agents useful for blocking nonspecific uptake by the RES are known and routinely used.

Nonspecific binding of phage to RES or to other sites also can be prevented by coinjecting, for example, mice with a specific phage display library together with the same phage made noninfective (Smith et al., supra, 1990, 1993). In addition, a peptide that homes to tumor in an organ containing an RES component can be identified by preparing a phage display library using phage that exhibit low background binding to the particular organ. For example, Merrill et al. (*Proc. Natl. Acad. Sci., USA* 93:3188–3192 (1996), which is incorporated herein by reference) selected lambda-type phage that are not taken up by the RES and, as a result, remain in the circulation for a prolonged period of time. A filamentous phage variant, for example, can be selected using similar methods.

Selective homing can be demonstrated by determining the specificity of a tumor homing molecule for the tumor as compared to a control organ or tissue. Selective homing also can be demonstrated by showing that molecules that home to a tumor, as identified by one round of in vivo panning, are enriched for tumor homing molecules in a subsequent round of in vivo panning. For example, phage expressing peptides that selectively home to a melanoma tumor were isolated by in vivo panning, then were subjected to additional rounds of in vivo panning. Following a second round of screening, phage recovered from the tumor showed a 3-fold enrichment in homing to the tumor as compared to brain. Phage recovered from the tumor after a third round of screening showed an average of 10-fold enrichment in homing to the tumor as compared to brain. Selective homing also can be demonstrated by showing that molecules that home to a selected tumor, as identified by one round of in vivo panning, are enriched for tumor homing molecules in a subsequent round of in vivo panning.

Tumor homing molecules can be identified by in vivo panning using, for example, a mouse containing a transplanted tumor. Such a transplanted tumor can be, for example, a human tumor that is transplanted into immunodeficient mice such as nude mice or a murine tumor that is maintained by passage in tissue culture or in mice. Due to the conserved nature of cellular receptors and of ligands that bind a particular receptor, it is expected that angiogenic vasculature and histologically similar tumor cells in various species can share common cell surface markers useful as target molecules for a tumor homing molecule. Thus, the skilled artisan would recognize that a tumor homing molecule identified using, for example, in vivo panning in a mouse having a murine tumor of a defined histological type such as a melanoma also would bind to the corresponding target molecule in a tumor in a human or other species. Similarly, tumors growing in experimental animals require associated neovascularization, just as that required for a tumor growing in a human or other species. Thus, a tumor homing molecule that binds a target molecule present in the vasculature in a tumor grown in a mouse likely also can bind to the corresponding target molecule in the vasculature of a tumor in a human or other mammalian subject. The general ability of a tumor homing molecule identified, for example, by homing to a human breast tumor, also to home to a human Kaposi's sarcoma or to a mouse melanoma indicates that the target molecules are shared by many tumors. Indeed, the results disclosed herein demonstrate that the target molecules are expressed in the neovasculature, which is host tissue (see Examples V and VIII).

A tumor homing molecule identified using in vivo panning in an experimental animal such as a mouse readily can be examined for the ability to bind to a corresponding tumor in a human patient by demonstrating, for example, that the molecule also can bind specifically to a sample of the tumor obtained from the patient. For example, the RGD-4C (CDCRGDCFC; SEQ ID NO:1) phage and NGR peptides have been shown to bind to blood vessels in microscopic sections of human tumors, whereas little or no binding occurs in the blood vessels of nontumor tissues. Thus, routine methods can be used to confirm that a tumor homing molecule identified using in vivo panning in an experimental animal also can bind the target molecule in a human tumor.

The steps of administering the library to the subject, collecting a selected tumor and identifying the molecules that home to the tumor, comprise a single round of in vivo panning. Although not required, one or more additional rounds of in vivo panning generally are performed. Where an additional round of in vivo panning is performed, the molecules recovered from the tumor in the previous round are administered to a subject, which can be the same subject used in the previous round, where only a part of the tumor was collected.

By performing a second round of in vivo panning, the relative binding selectivity of the molecules recovered from the first round can be determined by administering the identified molecules to a subject, collecting the tumor, and determining whether more phage is recovered from the tumor following the second round of screening as compared to those recovered following the first round. Although not required, a control organ or tissue also can be collected and the molecules recovered from the tumor can be compared with those recovered from the control organ. Ideally, no molecules are recovered from a control organ or tissue following a second or subsequent round of in vivo panning. Generally, however, a proportion of the molecules also will be present in a control organ or tissue. In this case, the ratio of molecules in the selected tumor as compared to the control organ (selected:control) can be determined. For example, phage that homed to melanoma following a first round of in vivo panning demonstrated a 3× enrichment in homing to the selected tumor as compared to the control organ, brain, following two additional rounds of panning (Example VI).

Additional rounds of in vivo panning can be used to determine whether a particular molecule homes only to the selected tumor or can recognize a target on the tumor that also is expressed in one or more normal organs or tissues in a subject or is sufficiently similar to the target molecule on the tumor. It is unlikely that a tumor homing molecule also will home to a corresponding normal tissue because the method of in vivo panning selects only those molecules that home to the tumor, which is selected. Where a tumor homing molecule also directs homing to one or more normal organs or tissues in addition to the tumor, the organs or tissues are considered to constitute a family of selected organs or tissues. Using the method of in vivo panning, molecules that home to only the selected tumor can be distinguished from molecules that also home to one or more selected organs or tissues. Such identification is expedited by collecting various organs or tissues during subsequent rounds of in vivo panning.

The term "control organ or tissue" is used to mean an organ or tissue other than the tumor for which the identification of a tumor homing molecule is desired. A control organ or tissue is characterized in that a tumor homing molecule does not selectively home to the control organ. A control organ or tissue can be collected, for example, to identify nonspecific binding of the molecule or to determine the selectivity of homing of the molecule. In addition, nonspecific binding can be identified by administering, for example, a control molecule, which is known not to home to a tumor but is chemically similar to a potential tumor homing molecule. Alternatively, where the administered molecules are linked to a support, administration of the supports, alone, also can be used to identify nonspecific binding. For example, a phage that expresses the gene III protein, alone, but that does not contain a peptide fusion protein, can be studied by in vivo panning to determine the level of nonspecific binding of the phage support.

As disclosed herein, specific homing of a tumor homing molecule readily can be identified by examining the selected tumor tissue as compared to a corresponding nontumor tissue, as well as to control organs or tissues. For example, immunohistological analysis can be performed on a tumor tissue and corresponding nontumor tissue using an antibody specific for a phage used to display tumor homing peptides (see Example V). Alternatively, an antibody can be used that is specific for a shared tag that expressed with the peptide, for example, a FLAG epitope or the like, such detection systems being commercially available.

In general, a library of molecules, which contains a diverse population of random or selectively randomized molecules of interest, is prepared, then administered to a subject. At a selected time after administration, the subject is sacrificed and the tumor is collected such that the molecules present in the tumor can be identified (see Example I). If desired, one or more control organs or tissues or a part of a control organ or tissue can be sampled. For example, mice bearing a breast tumor or a melanoma tumor were injected with a phage peptide display library, then, after about 1 to 5 minutes, the mice were anesthetized, either frozen in liquid nitrogen or, preferably, are perfused through the heart to terminate circulation of the phage, the tumor and one or more control organs were collected from each, phage present in the tumor and the control organs were recovered and peptides that selectively homed to the respective tumors were identified (see Examples I, II and VI).

In the examples provided, the animals were sacrificed to collect the selected tumor and control organ or tissue. It should be recognized, however, that only a part of a tumor need be collected to recover a support containing a molecule that homes to that tumor and, similarly, only part of an organ or tissue need be collected as a control. Thus, a part of a tumor, for example, can be collected by biopsy, such that a molecule such as a peptide expressed by a phage can be administered to the same subject a second time or more, as desired. Where the molecule that is to be administered a second time to the same subject is tagged or linked, for example, to a support, the tag or support should be nontoxic and biodegradable, so as not to interfere with subsequent rounds of screening.

In vitro screening of phage libraries previously has been used to identify peptides that: bind to antibodies or to cell surface receptors (Smith and Scott, supra, 1993). For example, in vitro screening of phage peptide display libraries has been used to identify novel peptides that specifically bound to integrin adhesion receptors (Koivunen et al., *J. Cell Biol.* 124:373–380 (1994a), which is incorporated herein by reference) and to the human urokinase receptor (Goodson et al., *Proc. Natl. Acad. Sci., USA* 91:7129–7133 (1994)). However, such in vitro studies provide no insight as to whether a peptide that can specifically bind to a selected receptor in vitro also will bind the receptor in vivo or whether the binding peptide or the receptor are unique to a specific organ in the body. Furthermore, the in vitro methods are performed using defined, well-characterized target molecules in an artificial system. For example, Goodson et al. (supra, 1994) utilized cells expressing a recombinant urokinase receptor. However, such in vitro methods are limited in that they require prior knowledge of the target molecule and yield little if any information regarding in vivo utility.

In vitro panning against cells in culture also has been used to identify molecules that can specifically bind to a receptor expressed by the cells (Barry et al., *Nature Med.* 2:299–305 (1996), which is incorporated herein by reference). However, the cell surface molecules that are expressed by a cell in vivo often change when the cell is grown in culture. Thus, in vitro panning methods using cells in culture also are limited in that there is no guarantee a molecule that is identified due to its binding to a cell in culture will have the same binding ability in vivo. Furthermore, it is not possible using in vitro panning to distinguish molecules that home only to the tumor cells used in the screening, but not to other cell types.

In contrast, in vivo panning requires no prior knowledge or availability of a target molecule and identifies molecules that bind to cell surface target molecules that are expressed in vivo. Also, since the "nontargeted" tissues are present during the screening, the probability of isolating tumor homing molecules that lack specificity of homing is greatly reduced. Furthermore, in obtaining tumor homing molecules by in vivo panning, any molecules that may be particularly susceptible to degradation in the circulation in vivo due, for example, to a metabolic activity, are not recovered. Thus, in vivo panning provides significant advantages over previous methods by identifying molecules that selectively home in vivo and the target molecule present in a tumor.

Once a target molecule has been identified, however, in vitro screening methods are useful for identifying additional tumor homing molecules. For example, the NGR receptor described herein is a target molecule that is useful for identifying additional tumor homing molecules that home to angiogenic vasculature. Methods of in vitro screening are well known in the art. For example, an NGR receptor can be contacted with a library of molecules and screened for binding in vitro. If desired, the NGR receptor can be immobilized, for example, to a solid support such as a bead or plate. An NGR receptor can be directly bound to the support, through covalent or non-covalent interactions, or can be immobilized indirectly through a molecule that binds to the NGR receptor. For example, an antibody that binds to an NGR receptor can be used to immobilize an NGR receptor (see Example X). The library is contacted with the NGR receptor in vitro and screened for binding activity. A library with tagged molecules are particularly useful for identifying molecules that bind to an NGR receptor.

Once additional molecules that bind to the target molecule are identified, these additional molecules can be tested in vivo to determine if the newly identified molecules can bind to the target molecule and home to angiogenic vasculature in vivo. For example, a newly identified molecule that binds to an NGR receptor can be further characterized by screening the molecule in vivo using the methods described herein and determining if the newly identified molecule can home to angiogenic vasculature. Thus, the identification of a target molecule such as an NGR receptor can be advantageously used to identify molecules that bind to an NGR receptor and home to angiogenic vasculature.

Although mechanisms by which the disclosed method of in vivo panning works have not been fully defined, one possibility is that a molecule such as a peptide expressed on a phage recognizes and binds to a target molecule present on endothelial cells lining the blood vessels in a tumor. Evidence indicates, for example, that the vascular tissues in various organs differ from one another and that such differences can be involved in regulating cellular trafficking in the body. For example, lymphocytes home to lymph nodes or other lymphoid tissues due, in part, to the expression of specific "address" molecules by the endothelial cells in those tissues (Salmi et al., *Proc. Natl. Acad. Sci. USA* 89:11436–11440 (1992); Springer, *Cell* 76:301–314 (1994)). Similarly, various leukocytes can recognize sites of inflammation due, in part, to the expression of endothelial cell markers induced by inflammatory signals (see Butcher and Picker, *Science* 272:60–66 (1996); Springer, supra, 1994). Thus, endothelial cell markers provide a potential target for directing, for example, a drug, which can be linked to a tumor homing molecule, to a tumor in a subject.

In some cases, the metastasis of cancer cells to specific organs also can be due to recognition by the tumor cell of an organ specific marker, including organ specific endothelial cell markers (Fidler and Hart, *Science* 217:998–1003 (1982)). The pattern of metastasis of many cancers can be explained by assuming that circulating tumor cells are preferentially trapped in the first vascular bed encountered. Thus, the lungs and the liver are the most frequent sites of cancer metastasis. However, some cancers show patterns of metastasis that are not explained by circulatory routing. Metastasis of such cancers may be due to the presence of selectively expressed address molecules such as endothelial cell surface molecules expressed in the organ to which the cancer metastasizes (see Goetz et al., *Int. J. Cancer* 65:192–199 (1996); Zhu et al., *Proc. Natl. Acad. Sci., USA* 88:9568–9572 (1991); Pauli et al., *Cancer Metast. Rev.* 9:175–189 (1990); Nicolson, *Biochim. Biophys. Acta* 948:175–224 (1988)). The identification of molecules that bind to such organ-specific endothelial cell markers can provide a means to prevent tumor cell metastasis to the particular organ.

Using in vivo panning to a breast carcinoma, a melanoma and a Kaposi's sarcoma, phage expressing various peptides that selectively homed to tumors were identified (see Tables 1, 2 and 3, respectively). Due to the large size of the phage (900–1000 nm) and the short time the phage were allowed to circulate (3 to 5 min), it is unlikely that a substantial number of phage would have exited the circulatory system, particularly in the brain and kidney. Tissue staining studies indicated that the tumor homing molecules that were identified primarily homed to and bound endothelial cell surface markers, which likely are expressed in an organ-specific manner. These results indicate that in vivo panning can be used to identify and analyze endothelial cell specificities. Such an analysis is not possible using endothelial cells in culture because the cultured cells tend to lose their tissue-specific differences (Pauli and Lee, *Lab. Invest.* 58:379–387 (1988)).

Although the conditions under which the in vivo pannings were performed identified tumor homing peptides that generally bind to endothelial cell markers, the specific presence of phage expressing tumor homing peptides also was observed in tumor parenchyma, particularly at later times after administration of the peptides (Example V). These results demonstrate that phage expressing peptides can pass through the blood vessels in the tumor, possibly due to the fenestrated nature of the blood vessels, and indicate that the in vivo panning method can be useful for identifying target molecules expressed by tumor cells, as well as target molecules expressed by endothelial cells.

Phage peptide display libraries were constructed essentially as described by Smith and Scott (supra, 1993; see, also, Koivunen et al., *Biotechnology* 13:265–270 (1995); Koivunen et al., *Meth. Enzymol.* 245:346–369 (1994b), each of which is incorporated herein by reference). Oligonucleotides encoding peptides having substantially random amino acid sequences were synthesized based on an "NNK" codon, wherein "N" is A, T, C or G and "K" is G or T. "NNK" encodes 32 triplets, which encode the twenty amino acids and an amber STOP codon (Scott and Smith, supra, 1990). In some libraries, at least one codon encoding cysteine also was included in each oligonucleotide so that cyclic peptides could be formed through disulfide linkages (Example I). The oligonucleotides were inserted in frame with the sequence encoding the gene III protein (gIII) in the vector fuse 5 such that a peptide-gIII fusion protein can be expressed. Following expression, the fusion protein is expressed on the surface of the phage containing the vector (Kcoivunen et al., supra, 1994b; Smith and Scott, supra, 1993).

Following in vivo panning, the phage isolated based on their ability to selectively home to human breast carcinoma, mouse melanoma or human Kaposi's sarcoma tumors displayed only a few different peptide sequences (see Tables 1, 2 and 3, respectively). One of the screenings revealed peptide sequences that contained the arginine-glycine-aspartic acid (RGD) integrin recognition sequence (Ruoslahti, *Ann. Rev. Cell Devel. Biol.* 12:697 (1996)) in the context of a peptide previously demonstrated to bind selectively to $\alpha_V$-containing integrins (Koivunen et al., supra, 1995; WO 95/14714). The sequences of most of the remaining tumor homing peptides did not reveal any significant similarities with known ligands for endothelial cell receptors. However, one of the tumor homing peptides contained the asparagine-glycine-arginine (NGR) motif, which is a weak integrin binding motif similar to the motifs present in integrin-binding peptides (Ruoslahti et al., U.S. Pat. No. 5,536,814, issued Jul. 16, 1996, which is incorporated herein by reference; see, also, Koivunen et al., supra, 1994a). Other screenings have revealed numerous NGR-containing peptides (see Table 1). Despite the weak integrin binding ability of NGR peptides, an integrin receptor may not be the target molecule recognized by the NGR tumor homing peptices exemplified herein (Example VIII). As used herein, the term "integrin" means a heterodimeric cell surface adhesion receptor.

The peptides expressed by the phage that homed to the breast tumor included the peptides CGRECPRLCQSSC (SEQ ID NO:2) and CNGRCVSGCAGRC (SEQ ID NO:3; see Table 1; Example II). Similarly, tumor homing peptides, including the peptides CDCRGDCFC (SEQ ID NO:1) and CGSLVRC (SEQ ID NO:5), were identified from two other phage libraries administered to breast tumor bearing mice (Table 1). Some of these motifs, as well as novel one, also were isolated in the screen with mouse melanoma and human Kaposi's sarcoma (see Tables 2 and 3). These results demonstrated that tumor homing molecules can be identified using in vivo panning.

Three main tumor homing motifs emerged. As discussed above, one motif contained the sequence RGD (Ruoslahti, supra, 1996) embedded in the peptide structure, CDCRGD-CFC (SEQ ID NO:1), which is known to bind selectively to $\alpha_V$ integrins (Koivunen et al., supra, 1995; WO 95/14714). Since the $\alpha_V\beta_3$ and $\alpha_V\beta_5$ integrins are markers of angiogenic vessels (Brooks et al., supra, 1994; Friedlander et al., *Science* 270:1500 (1995)), a phage expressing the peptide CDCRGDCFC (SEQ ID NO:1) (designated RGD-4C) was examined for tumor targeting and, as disclosed herein, homed to tumors in a highly selective manner (see Example III). Furthermore, homing by the RGD-4C (CDCRGDCFC; SEQ ID NO:1) phage was inhibited by coadministration of the free CDCRGDCFC (SEQ ID NO:1) peptide.

Another breast tumor homing peptide had the sequence CNGRCVSGCAGRC (SEQ ID NO:3), which contains the NGR motif previously shown to have weak integrin binding activity (Koivunen et al., *J. Biol. Chem.* 268:20205–20210 (1993), which is incorporated herein by reference),; Koivunen et al., supra, 1994a; WO 95/14714). Since an NGR containing peptide was identified, two additional peptides, the linear peptide, NGRAHA (SEQ ID NO:6), and the cyclic peptide, CVLNGRMEC (SEQ ID NO:7), each of which contains the NGR motif, were examined for tumor homing. Like the phage expressing CNGRCVSGCAGRC (SEQ ID NO:3), phage expressing NGRAHA (SEQ ID NO:6) or CVLNGRMEC (SEQ ID NO:7) homed to the tumors. Furthermore, tumor homing was not dependent on the tumor type or on species, as the phage accumulated selectively in human breast carcinoma, as well as in the tumors of mice bearing a mouse melanoma and mice bearing a human Kaposi's sarcoma xenograft.

The various peptides, including RGD- and NGR-containing peptides, generally were bound to the tumor blood vessels. The minimal cyclic NGR peptide, CNGRC (SEQ ID NO:8), was synthesized based on the CNGRCVS-GCAGRC (SEQ ID NO:3) sequence. When the CNGRC (SEQ ID NO:8) peptide was co-injected with phage expressing either CNGRCVSGCAGRC (SEQ ID NO:3), NGRAHA (SEQ ID NO:6) or CVLNGRMEC (SEQ ID NO:7), accumulation of the phage in the breast carcinoma xenografts was inhibited. However, the CNGRC (SEQ ID NO:8) peptide did not inhibit the homing of phage expressing the RGD-4C (CDCRGDCFC; SEQ ID NO:1) peptide, even when administered in amounts up to ten times higher than those that inhibited the homing of the NGR phage. In comparison, the RGD-4C (CDCRGDCFC; SEQ ID NO:1) peptide partially inhibited the homing of the NGR phage, although the amount needed was 5 to 10 fold higher than that of the CNGRC peptide (SEQ ID NO:8). These results indicate that NGR peptides and RGD peptides bind to different receptor sites in tumor vasculature.

A third motif, GSL (glycine-serine-leucine), also was identified following in vivo panning in mice bearing breast carcinoma, malignant melanoma or Kaposi's sarcoma. Homing of phage expressing the GSL peptide, CGSLVRC (SEQ ID NO:5), was inhibited by coadministration of the free CGSLVRC (SEQ ID NO:5) peptide. Like the RGD and NGR peptides, phage expressing GSL peptides also bound to blood vessels of tumors. In view of the identification of the conserved RGD, NGR and GSL motifs present in tumor homing peptides, as disclosed herein, it will be recognized that peptides containing such motifs can be useful as tumor homing peptides and, in particular, for forming conjugates that can target a moiety such as a cancer chemotherapeutic agent or a diagnostic agent to a tumor.

Various peptide libraries containing up to 13 amino acids were constructed and the NGR peptide, CNGRCVSG-CAGRC (SEQ ID NO:3), was obtained as a result of in vivo panning against a breast tumor. This NGR peptide, which was obtained by screening a random peptide library, was a tumor homing peptide (see Example VIII). In addition, when a peptide library was constructed based on the formula CXXXNGRXX (SEQ ID NO:13) or CXXCNGRCX (SEQ ID NO:14), each of which is biased toward NGR sequences, and used for in vivo panning against a breast tumor, numerous NGR peptides were obtained (see Table 1).

These results indicate that a tumor homing peptide of the invention can comprise the amino acid sequence RGD or NGR or GSL. Such tumor peptides can be as small as five amino acids, such as CNGRC (SEQ ID NO:8). Such tumor homing peptides also can be not only at least 13 amino acids in length, which is the largest peptide exemplified herein, but can be up to 20 amino acids, or 30 amino acids, or 50 to 100 amino acids in length, as desired. A tumor homing peptide of the invention conveniently is produced by chemical synthesis.

Immunohistochemical analysis was performed by comparing tissue staining for phage allowed to circulate for about four minutes, followed by perfusion through the heart of the mice, or with tissues analyzed 24 hours after phage injection (see FIG. 3). At 24 hours following administration, essentially no phage remain in the circulation and, therefore, perfusion is not required (Pasqualini et al., supra, 1997). Strong phage staining was observed in tumor vasculature, but not in normal endothelium, in samples examined four minutes after administration of the CNGRCVSGCAGRC (SEQ ID NO:3) phage (Example V; compare FIGS. 3E, 3G, 3H and 3J). In comparison, staining of the tumor was strong at 24 hours and appeared to have spread outside the blood vessels into the tumor parenchyma (compare FIGS. 3A to 3D and 3F (tumor) with FIGS. 3I and 3K to 3V (nontumor)).

The NGRAHA (SEQ ID NO:6) and CVLNGRMEC (SEQ ID NO:7) phage showed similar staining patterns (Example V). In contrast, the control organs and tissues showed little or no immunostaining, confirming the specificity of the NGR motifs for tumor vessels. Spleen and liver, however, captured phage, as expected, since uptake by the reticuloendothelial system is a general property of phage particles, independent of the presence of peptide expression by the phage (Pasqualini et al., supra, 1997).

Immunostaining also was observed following administration of phage expressing the GSL motif containing peptide, CLSGSLSC (SEQ ID NO:4), and, like that of the NGR peptides, was localized to the blood vessels, in this case, within a melanoma tumor (see below; see, also, Examples V and VI). Similarly, immunostaining following administration of phage expressing the RGD motif containing peptide, RGD-4C (CDCRGDCFC; SEQ ID NO:1), to breast tumor bearing mice was localized to the blood vessels in the tumor, but was not observed in brain, kidney or various other nontumor tissues (see Examples III and V; see, also, Pasqualini et al., supra, 1997). These results demonstrate that the various tumor homing peptides generally home to tumor vasculature.

The general applicability of the in viva panning method for identifying molecules that home to a tumor was examined by injecting mice bearing a syngeneic melanoma with phage expressing a diverse population of peptides (Example VI). The B16 mouse melanoma model was selected for these studies because the tumors that form are highly vascularized and because the biology of this tumor line has been thoroughly characterized (see Miner et al., *Cancer Res.* 42:4631–4638 (1982)). Furthermore, because the B16 melanoma cells are of mouse origin, species differences between the host and the tumor cell donor will not affect, for example, the distribution of phage into the tumor as compared to into normal organs. As disclosed herein, in vivo panning against B16 melanoma cells revealed tumor homing peptides, including, for example, the GSL moiety containing peptide CLSGSLSC (SEQ ID NO:4; see, also, Table 2) and immunohistochemical staining of the tumor and other organs using an anti-phage antibody demonstrated that the CLSGSLSC (SEQ ID NO:4) expressing phage resulted in immunostaining in the melanoma, but essentially no staining in skin, kidney or other control organs (Example VI). The staining pattern generally followed the blood vessels within the melanoma, but was not strictly confined to the blood vessels.

Although in vivo panning was performed in mice, at least the peptides comprising an NGR, RGD or GSL motif also likely can target human vasculature. The NGR phage binds to blood vessels in the transplanted human breast tumor, but not to blood vessels in normal tissues, indicating that this motif can be particularly useful for tumor targeting in patients. The CDCRGDCFC (SEQ ID NO:1) peptide binds to human $\alpha_v$-integrins (Koivunen et al., supra, 1995), which are selectively expressed in tumor blood vessels of human patients (Max et al., *Int. J. Cancer* 71:320 (1997); Max et al., *Int. J. Cancer* 72:706 (1997)). Use of a moiety/CDCRGDCFC (SEQ ID NO:1) conjugate to target the moiety to a tumor also provides the additional advantage that the moiety will be targeted to tumor cells, themselves, because breast carcinoma cells, for example, can express the $\alpha_v\beta_3$ integrin (Pasqualini et al., supra, 1997). In fact, many human tumors express this integrin, which may be involved in the progression of certain tumors such as malignant melanomas (Albelda et al., *Cancer Res.* 50:6757–6764 (1990); Danen et al., *Int. J. Cancer* 61:491–496 (1995);

Felding-Habermann et al., *J. Clin. Invest.* 89:2018–2022 (1992); Sanders et al., *Cold Spring Harb. Symp. Quant. Biol.* 58:233–240 (1992); Mitjans et al., *J. Cell. Sci.* 108:3067–3078 (1995)). Unlike the RGD-4C (CDCRGDCFC; SEQ ID NO:1) peptide, the NGR peptides do not appear to bind to MDA-MD-435 breast carcinoma cells. However, NCR peptides were able to deliver a therapeutically effective amount of doxorubicin to breast tumors (Examples VIII and XV), indicating that, even where a tumor homing molecule homes only to tumor vasculature, i.e., not directly to the tumor cells, such vasculature targeting in sufficient to confer the effect of the moiety linked to the molecule.

Since the $\alpha_V\beta_3$ integrin is expressed by endothelial cells in angiogenic vasculature, experiments were performed to determine whether tumor vasculature that is undergoing angiogenesis can be targeted in vivo using methods as disclosed herein. Phage expressing the peptide, RGD-4C (CDCRGDCFC; SEQ ID NO:1; see, Koivunen et al., supra, 1995), which is known to bind to the $\alpha_V\beta_3$ integrin, were injected into mice bearing tumors formed from human breast carcinoma cells, mouse melanoma cells or human Kaposi's sarcoma cells (see Example V). The RGD-4C (CDCRGDCFC; SEQ ID NO:1) phage selectively homed to each of the tumors, whereas such homing did not occur with control phage. For example, in mice bearing tumors formed by implantation of human breast carcinoma cells, a twenty- to eighty-fold greater number of the RGD-4C (CDCRGDCFC; SEQ ID NO:1) phage, as compared to unselected control phage, accumulated in the tumor.

Tissue staining for the phage showed accumulation of the RGD-4C (CDCRGDCFC; SEQ ID NO:1) phage in the blood vessels within the tumor, whereas no staining was observed in brain, kidney or other control organs. Specificity of tumor homing by the RGD-4C (CDCRGDCFC; SEQ ID NO:1) phage was demonstrated by competition experiments, in which coinjection of the free RGD-4C (CDCRGDCFC; SEQ ID NO:1) peptide greatly reduced tumor homing of the RGD phage, whereas coinjection of a non-RGD-containing control peptide had no effect on homing of the RGD phage (see Example III). These results demonstrate that the $\alpha_V\beta_3$ target molecule is expressed on the luminal surface of endothelial cells in a tumor and that a peptide that binds to an $\alpha_V$-containing integrin can bind selectively to this integrin and, therefore, to vasculature undergoing angiogenesis.

The results of these studies indicate that tumor homing molecules can be identified by in vivo panning and that, in some cases, a tumor homing molecule can home to vascular tissue in the tumor as well as to tumor parenchyma, probably due to the fenestrated nature of the blood vessels permitting ready exit of the phage from the circulatory system. Due to the ability of such tumor homing molecules to home to tumors, the molecules are useful for targeting a linked moiety to tumors. Thus, the invention provides conjugates comprising a tumor homing molecule linked to a moiety, such conjugates being useful for targeting the moiety to tumor cells.

The ability of a molecule that homes to a particular tumor to selectively home to another tumor of the same or a similar histologic type can be determined using, for example, human tumors grown in nude mice or mouse tumors grown in syngeneic mice for these experiments. For example, various human breast cancer cell lines, including MDA-MB-435 breast carcinoma (Price et al., *Cancer Res.* 50:717–721 (1990)), SKBR-1-II and SK-BR-3 (Fogh et al., *J. Natl. Cancer Inst.* 59:221–226 (1975)), and mouse mammary tumor lines, including EMT6 (Rosen et al., *Int. J. Cancer* 57:706–714 (1994)) and C3-L5 (Lala and Parhar, *Int. J. Cancer* 54:677–684 (1993)), are readily available and commonly used as models for human breast cancer. Using such breast tumor models, for example, information relating to the specificity of an identified breast tumor homing molecule for diverse breast tumors can be obtained and molecules that home to a broad range of different breast tumors or provide the most favorable specificity profiles can be identified. In addition, such analyses can yield new information, for example, about tumor stroma, since stromal cell gene expression, like that of endothelial cells, can be modified by the tumor in ways that cannot be reproduced in vitro.

Selective homing of a molecule such as a peptide or protein to a tumor can be due to specific recognition by the peptide of a particular cell target molecule such as a cell surface receptor present on a cell in the tumor. Selectivity of homing is dependent on the particular target molecule being expressed on only one or a few different cell types, such that the molecule homes primarily to the tumor. As discussed above, the identified tumor homing peptides, at least in part, can recognize endothelial cell surface markers in the blood vessels present in the tumors. However, most cell types, particularly cell types that are unique to an organ or tissue, can express unique target molecules. Thus, in vivo panning can be used to identify molecules that selectively home to a particular type of tumor cell such as a breast cancer cell and specific homing can be demonstrated by performing the appropriate competition experiments.

Treatment of human breast cancer xenografts in mice using doxorubicin was selected as a model for exemplifying the present invention. CDCRGDCFC (SEQ ID NO:1) and CNGRC (SEQ ID NO:8) were coupled to doxorubicin (Example VII) and the peptide/doxorubicin conjugates were used to treat mice bearing tumors derived from human MDA-MB-435 breast carcinoma cells (Examples VIII and XV). Mice were treated with 5 μg/week of doxorubicin equivalent (i.e., either free doxorubicin or the doxorubicin component of the peptide/doxorubicin conjugate), as compared to the more commonly used 50–200 μg/mouse used in tumor bearing mice (Berger et al., In "The Nude Mouse in Oncology Research" (CRC Press 1991)). The lower dose was selected because it was expected that the conjugate would be more effective than the free drug.

MDA-MB-435 tumor-bearing mice treated with the doxorubicin/RGD-4C (CDCRGDCFC; SEQ ID NO:1) conjugate had significantly smaller tumors, less spread to regional lymph nodes, and fewer pulmonary metastasis than mice treated with free doxorubicin (see Example VIII). All of the mice treated with the doxorubicin/RGD-4C (CDCFRGDCFC; SEQ ID NO:1) conjugate survived beyond the time when all of the mice treated with free doxorubicin had died from widespread disease. In a dose-escalation experiment, the tumor bearing mice were treated with the doxorubicin/RGD-4C (CDCRGDCFC; SEQ ID NO:1) conjugate at 30 μg/mouse every three weeks for three cycles, then were observed, without further treatment, for an extended period of time. The conjugate treated mice all remained alive more than 6 months after the control, doxorubicin treated mice had died (Example VIII). These results indicate that primary tumor growth and metastasis significantly were inhibited in mice treated with the conjugate and that cures may have occurred.

Many of the mice that received doxorubicin/RGD-4C (CDCRGDCFC; SEQ ID NO:1) conjugate presented marked skin ulceration and tumor necrosis; no such signs were observed in mice treated with free doxorubicin or with doxorubicin conjugated to an unrelated peptide (Example VIII). Histopathological analysis disclosed a pronounced destruction of the vasculature in the tumors treated with conjugate as compared to mice treated with free doxorubicin. Furthermore, when tumors were removed from the mice and the tumor cells plated in culture, viability of cells from the tumors of mice receiving the doxorubicin/RGD-4C (CDCRGDCFC; SEQ ID NO:1) conjugate was about 3 fold less than cells from tumors of mice treated with the free doxorubicin (see Example VIII). These results demonstrate that administration to a tumor bearing mouse of a conjugate comprising a chemotherapeutic agent linked to a tumor homing molecule is more efficacious than administration of the agent, alone, in treating a tumor.

Toxicity was determined by administration of 200 μg/doxorubicin equivalent in mice with very large, size matched breast tumors. All of the mice treated with the doxorubicin/RGD-4C (CDCRGDCFC; SEQ ID NO:1) conjugate survived more than a week, while all of the mice treated with free doxorubicin died within 48 hours of the administration of the drug (Example VIII). These results indicate that accumulation of the tumor homing peptide/doxorubicin conjugate in the large tumors can reduce systemic toxicity of the agent.

Similar toxicity and treatment efficacy results were obtained when breast tumor bearing mice were treated using a doxorubicin/CNGRC (SEQ ID NO:8) conjugate. Tumors in the mice treated with the CNGRC (SEQ ID NO:8) conjugate were significantly smaller than in the control groups; the conjugate suppressed tumor growth almost completely. A strong effect on survival also occurred. Free doxorubicin or doxorubicin conjugated to an unrelated peptide, at the dose used, had little if any effect on tumor growth relative to vehicle alone.

Cytotoxic activity of free doxorubicin and the doxorubicin/peptide conjugates was compared in vitro using MDA-MB-435 cells. When cells were exposed to free doxorubicin, doxorubicin/RGD-4C (CDCRGDCFC; SEQ ID NO:1) or doxorubicin conjugated to an unrelated peptide for 30 minutes, cell death occurred only in the cultures treated with the doxorubicin/RGD-4C (CDCRGDCFC; SEQ ID NO:1) conjugate. In comparison, cells were killed by all of the treatments after 24 hours of exposure. These results indicate that enhanced cellular uptake of the doxorubicin/RGD-4C (CDCRGDCFC; SEQ ID NO:1) conjugate occurs.

As disclosed herein, tumor homing molecules of the invention can bind to the endothelial lining of small blood vessels of tumors. The vasculature within tumors is distinct, presumably due to the continual neovascularization, resulting in the formation of new blood vessels required for tumor growth. The distinct properties of the angiogenic neovasculature within tumors are reflected in the presence of specific markers in endothelial cells and pericytes (Folkman, *Nature Biotechnol.* 15:510 (1997); Risau, *FASEB J.* 9:926–933 (1995); Brooks et al., supra, 1994); these markers likely are being targeted by the tumor homing molecules of the invention.

The ability of a tumor homing molecule to target the blood vessels in a tumor provides substantial advantages over methods of systemic treatment or methods that directly target the tumor cells. For example, tumor cells depend on a vascular supply for survival and the endothelial lining of blood vessels is readily accessible to a circulating probe. Conversely, in order to reach solid tumor cells, a chemotherapeutic agent must overcome potentially long diffusion distances, closely packed tumor cells, and a dense fibrous stroma with a high interstitial pressure that impedes extravasation (Burrows and Thorpe, *Pharmacol. Ther.* 64:155–174 (1994)).

In addition, where the tumor vasculature is targeted, the killing of all target cells may not be required, since partial denudation of the endothelium can lead to the formation of an occlusive thrombus halting the blood flow through the entirety of the affected tumor vessel (Burrows and Thorpe, supra, 1994). Furthermore, unlike direct tumor targeting, there is an intrinsic amplification mechanism in tumor vasculature targeting. A single capillary loop can supply nutrients to up to 100 tumor cells, each of which is critically dependent on the blood supply (Denekamp, *Cancer Metast. Rev.* 9:267–282 (1990); Folkman, supra, 1997).

Endothelial cells in a tumor also are unlikely to lose a cell surface target receptor or develop a drug resistance phenotype, as can develop through mutation and clonal evolution of tumor cells, because endothelial cells are genetically stable despite their high proliferation rates (Burrows and Thorpe, supra, 1994; Folkman, supra, 1995; Folkman, supra, 1997). In this regard, it has been long recognized by medical oncologists that, while tumors treated with chemotherapeutic agents commonly develop drug resistance, normal tissues such as bone marrow do not develop such resistance. Thus, toxicity to normal tissues such as chemotherapy induced myelosuppression continues to occur during a treatment, even after tumor cells have become drug resistant. Since the endothelial cells in blood vessels supplying a tumor are nontumor cells, it is expected that they will not develop resistance to chemotherapeutic agents, in a manner analogous to bone marrow cells. In fact, drug resistance has not been observed during long term anti-angiogenic therapy in either experimental animals or in clinical trials (Folkman, supra, 1997).

Linking of a moiety larger than an agent such as a drug or other organic or biologic molecule to a tumor homing molecule for the purpose of directing homing of the moiety to the selected tumor is exemplified by expressing an RGD-containing peptide on a phage, wherein the peptide directed homing of the phage to breast tumor vasculature (Example V). These results indicate that a tumor homing molecule of the invention can be linked to other moieties including, for example, a chambered microdevice or a liposome or a cell such as a white blood cell (WBC), which can be a cytotoxic T cell or a killer cell, wherein upon administration of the tumor homing molecule/WBC conjugate, the molecule directs homing of the WBC to the tumor, where the WBC can exert its effector function.

The linking of a moiety to a tumor homing molecule can result in the molecule directing homing of the linked moiety to a tumor. For example, the linking of a brain homing peptide to a RBC directed homing of the RBC to brain (see U.S. Pat. No. 5,622,699; Pasqualini and Ruoslahti, supra, 1996). This result indicates that a tumor homing molecule of the invention also can be linked to cell type or to a physical, chemical or biological delivery system such as a liposome or other encapsulating device, which can contain an agent such as drug, in order to direct the cell type or the delivery system to a selected tumor. For example, a tumor homing molecule identified by in vivo panning can be linked to a white blood cell (WBC) such as a cytotoxic T cell or a killer cell, wherein upon administration of the tumor homing molecule/WBC conjugate, the molecule directs homing of the WBC to the tumor, where the WBC can exert its effector function. Similarly, a tumor homing molecule can be linked to a liposome or to a chambered microdevice comprising, for example, a permeable or semipermeable membrane, wherein an agent such as a drug to be delivered to a selected tumor is contained within the liposome or microdevice. Such compositions also can be useful, for example, for delivering a nucleic acid molecule to a tumor cells, thereby providing a means for performing in vivo targeted gene therapy.

In one embodiment, a tumor homing molecule is linked to a moiety that is detectable external to the subject, thereby providing a composition useful to perform an in vivo diagnostic imaging study. For example, in vivo imaging using a detectably labeled tumor homing peptide can identify the presence of a tumor in a subject. For such studies, a moiety such as a gamma ray emitting radionuclide, for example, indium-111 or technitium-99, can be linked to the tumor homing molecule and, following administration to a subject, can be detected using a solid scintillation detector. Similarly, a positron emitting radionuclide such as carbon-11 or a paramagnetic spin label such as carbon-13 can be linked to the molecule and, following administration to a subject, the localization of the moiety/molecule can be detected using positron emission transaxial tomography or magnetic resonance imaging, respectively. Such methods can identify a primary tumor as well as a metastatic lesion, which may not be detectable using other methods. Having identified the presence of a cancer in a subject, in another embodiment of the invention, the tumor homing molecule is linked to a cytotoxic agent such as ricin or a cancer chemotherapeutic agent such as doxorubicin in order to direct the moiety to the tumor or can be linked to a chambered microdevice, which can contain a chemotherapeutic drug or other cytotoxic agent. Use of such a composition provides a means to selectively killing of the tumor, while substantially sparing normal tissues in a cancer patient and, therefore, the conjugates of the invention provide useful medicaments for diagnosing or treating a cancer patient.

The skilled artisan would recognize that: various tumor homing molecules can selectively home only to a tumor or can selectively home to a tumor and to a family of selected organs, including, in some cases, the normal tissue counterpart to the tumor. Thus, the artisan would select a tumor homing peptide for administration to a subject based on the procedure being performed. For example, a tumor homing molecule that homes only to a tumor can be useful for directing a therapy to the tumor. In comparison, a tumor homing molecule that selectively homes not only to the tumor, but also to one or more normal organs or tissues, can be used in an imaging method, whereby homing to an organ or tissue other than the tumor provides an internal imaging control. Such an internal control can be useful, for example, for detecting a change in the size of a tumor in response to a treatment, since the normal organ is not expected to change in size and, therefore, can be compared with the tumor size.

Tumor homing peptides, which are identified by in vivo panning, can be synthesized in required quantities using routine methods of solid state peptide synthesis or can be purchased from commercial sources (for example, Anaspec; San Jose Calif.) and a desired moiety can be linked to the molecule. Several methods useful for linking a moiety to a molecule are known in the art, depending on the particular chemical characteristics of the molecule. For example, methods of linking haptens to carrier proteins as used routinely in the field of applied immunology (see, for example, Harlow and Lane, supra, 1988; Hermanson, supra, 1996).

It is recognized that, in some cases, a drug can lose cytotoxic efficacy upon conjugation or derivatization depending, for example, on the conjugation procedure or the chemical group utilized (Hurwitz et al., *Cancer Res.* 35:1175–1181 (1975); Trail et al., *Science* 261:212–215 (1993); Nagy et al., *Proc. Natl. Acad. Sci., USA* 93:7269–7273 (1996)). Moreover, it is recognized that a phage that yields a tumor homing peptide of the invention displays as many as five of the peptides. Thus, there is a possibility that the affinity of an individual peptide is too low for effective tumor homing and that multivalent, rather than univalent, peptide conjugates must be used. However, as disclosed herein, doxorubicin maintained cytotoxic activity when used as a conjugate with tumor homing peptides (see Examples VIII and XV), thus allaying the potential concerns discussed above.

A moiety such as a therapeutic or diagnostic agent can be conjugated to a tumor homing peptide using, for example, carbodiimide conjugation (Bauminger and Wilchek, *Meth. Enzymol.* 70:151–159 (1980), which is incorporated herein by reference)(see Example VII). Alternatively, a moiety can be coupled to a homing molecule as described by Nagy et al., *Proc. Natl. Acad. Sci. USA* 93:7269–7273 (1996); and Nagy et al., *Proc. Natl. Acad. Sci. USA* 95:1794–1799 (1998), each of which is incorporated herein by reference.

Carbodiimides comprise a group of compounds that have the general formula R—N=C=N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups. Carbodiimide conjugation has been used to conjugate a variety of compounds to carriers for the production of antibodies.

The water soluble carbodiimide, 1-ethyl-3-(3-dimethylaminopropyl) carbodiimide (EDC) is particularly useful for conjugating a moiety to a tumor homing peptide and was used to conjugate doxorubicin to tumor homing peptides (Example VII). The conjugation of doxorubicin and a tumor homing peptide requires the presence of an amino group, which is provided by doxorubicin, and a carboxyl group, which is provided by the peptide. EDC coupling of doxorubicin to the CNGRC (SEQ ID NO:8) peptide was performed using a 1:1 molar ratio of the peptide (carboxyl groups) to obtain a doxorubicin/CNGRC (SEQ ID NO:8; see Example VII).

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of the doxorubicin. The use of EDC and NHS in combination is commonly used for conjugation in order to increase yield of conjugate formation (Bauminger and Wilchek, supra, 1980).

Other methods for conjugating a moiety to a tumor homing molecule also can be used. For example, sodium periodate oxidation followed by reductive alkylation of appropriate reactants can be used, as can glutaraldehyde crosslinking. However, it is recognized that, regardless of which method of producing a conjugate of the invention is selected, a determination must be made that the tumor homing molecule maintains its targeting ability and that the moiety maintains its relevant function. Methods as disclosed in Examples VIII and XV or otherwise known in the art can confirm the activity of the moiety/tumor homing molecule conjugate.

The yield of moiety/tumor homing molecule conjugate formed is determined using routine methods. For example, HPLC or capillary electrophoresis or other qualitative or quantitative method can be used (see, for example, Liu et al., *J. Chromatogr.* 735:357–366 (1996); Rose et al., *J. Chro-* matogr. 425:419–412 (1988), each of which is incorporated herein by reference; see, also, Example VII). In particular, the skilled artisan will recognize that the choice of a method for determining yield of a conjugation reaction depends, in part, on the physical and chemical characteristics of the specific moiety and tumor homing molecule. Following conjugation, the reaction products are desalted to remove any free peptide and free drug.

When administered to a subject, the tumor homing molecule/moiety conjugate is administered as a pharmaceutical composition containing, for example, the conjugate and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art would know that a pharmaceutical composition containing a tumor homing molecule can be administered to a subject by various routes including, for example, orally or parenterally, such as intravenously. The composition can be administered by injection or by intubation. The pharmaceutical composition also can be a tumor homing molecule linked to liposomes or other polymer matrices, which can have incorporated therein, for example, a drug such as a chemotherapeutic agent (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

For the diagnostic or therapeutic methods disclosed herein, an effective amount of the tumor homing molecule/moiety conjugate must be administered to the subject. As used herein, the term "effective amount" means the amount of the conjugate that produces the desired effect. An effective amount often will depend on the moiety linked to the tumor homing molecule. Thus, a lesser amount of a radiolabeled molecule can be required for imaging as compared to the amount of a drug/molecule conjugate administered for therapeutic purposes. An effective amount of a particular molecule/moiety for a specific purpose can be determined using methods well known to those in the art.

The route of administration of a tumor homing molecule will depend, in part, on the chemical structure of the molecule. Peptides, for example, are not particularly useful when administered orally because they can be degraded in the digestive tract. However, methods for chemically modifying peptides to render them less susceptible to degradation by endogenous proteases or more absorbable through the alimentary tract are well known (see, for example, Blondelle et al., supra, 1995; Ecker and Crooke, supra, 1995; Goodman and Ro, supra, 1995). Such modifications can be performed on peptides identified by in vivo panning. In addition, methods for preparing libraries of peptidomimetics, which can contain D-amino acids, other non-naturally occurring amino acids, or chemically modified amino acids; or can be organic molecules that mimic the structure of peptide; or can be peptoids such as vinylogous peptoids, are known in the art and can be used to identify molecules that home to a tumor and are stable for oral administration.

Tumor homing molecules obtained using the methods disclosed herein also can be useful for identifying a target molecule such as a cell surface receptor or a ligand for a receptor, which is recognized by the tumor homing peptide, or for substantially isolating the target molecule. For example, a tumor homing peptide can be linked to a solid support such as a chromatography matrix. The linked peptide then can be used for affinity chromatography by passing an appropriately processed sample of a tumor over the column in order to bind a particular target molecule. The target molecule, which forms a complex with the tumor homing molecule, then can be eluted from the column and collected in a substantially isolated form. The substantially isolated target molecule then can be characterized using well known methods. A tumor homing peptide also can be linked to a detectable moiety such as a radionuclide, a fluorescent molecule, an enzyme or biotin and can be used, for example, to screen a sample in order to detect the presence of the target molecule in a tumor or to follow the target molecule during various isolation steps.

It follows that, upon identifying the presence of a target molecule in a tumor sample, the skilled artisan readily can obtain the target molecule in a substantially isolated form. For example, the sample containing the target molecule can be passed over a column containing attached thereto the relevant tumor homing molecule, thereby providing a means to obtain the target molecule in substantially isolated form (see Example X). Thus, the invention further provides a substantially isolated target molecule, which specifically binds a tumor homing molecule and which can be obtained using the methods disclosed herein.

The methods of the present invention were used to identify tumor homing peptides, which can selectively home to various tumors. It should be recognized that cysteine residues were included in some peptides such that cyclization of the peptides could be effected. In fact, the peptides containing at least two cysteine residues cyclize spontaneously. However, such cyclic peptides also can be active when present in a linear form (see, for example, Koivunen et al., supra, 1993) and, as disclosed herein, a linear peptide, NGRAHA (SEQ ID NO:6), also was useful as tumor homing molecule (Example VIII; see, also, Table 1). Thus, in some cases one or more cysteine residues in the peptides disclosed herein or otherwise identified as tumor homing peptides can be deleted without significantly affecting the tumor homing activity of the peptide. Methods for determining the necessity of a cysteine residue or of amino acid residues N-terminal or C-terminal to a cysteine residue for tumor homing activity of a peptide of the invention are routine and well known in the art.

A tumor homing peptide is useful, for example, for targeting a desired moiety to the selected tumor as discussed above. In addition, a tumor homing peptide can be used to identify the presence of a target molecule in a sample. As used herein, the term "sample" is used in its broadest sense to mean a cell, tissue, organ or portion thereof, including a tumor, that is isolated from the body. A sample can be, for example, a histologic section or a specimen obtained by biopsy or cells that are placed in or adapted to tissue culture. If desired, a sample can be processed, for example, by homogenization, which can be an initial step for isolating the target molecule to which a tumor homing molecule binds.

A tumor homing peptide such as a breast tumor homing peptide can be used to identify the target molecule expressed in a breast tumor. For example, a breast tumor homing peptide can be attached to a matrix such as a chromatography matrix to produce a peptide affinity matrix. A homogenized sample of a breast tumor can be applied to the peptide-affinity matrix under conditions that allow specific binding of the target: molecule to the tumor homing peptide (see, for example, Deutshcer, *Meth. Enzymol.*, Guide to Protein Purification (Academic Press, Inc., ed. M. P. Deutscher, 1990), Vol. 182, which is incorporated herein by reference; see, for example, pages 357–379). Unbound and nonspecifically bound material can be removed and the specifically bound breast tumor-derived target molecule can be isolated in substantially purified form. The presence or absence of the target molecule in normal breast tissue also can be determined. Such an analysis can provide insight into methods of treating the tumor.

As disclosed herein, a target molecule, which specifically binds a tumor homing molecule, can be identified by contacting a sample of a tumor with such a tumor homing molecule and identifying a target molecule bound by the tumor homing molecule. In parallel, the tumor homing molecule is contacted with a sample of a nontumor tissue corresponding to the tumor. The presence of the target molecule in the tumor sample can be identified by determining that the tumor homing molecule does not bind to a component of the corresponding nontumor tissue sample. Thus, the invention provides methods for dentifying the presence of a target molecule, which is expressed in a tumor and specifically bound by a tumor homing molecule.

Since numerous tumor homing peptides containing the NCR motif have been identified, for example, a tumor homing peptide comprising an NGR sequence can be used to isolate the NCR receptor. Thus, an NCR tumor homing target molecule for the NGR tumor homing peptide, then can be obtained in a substantially isolated form, as described in Example X. When used in reference to a target molecule, the term "substantially isolated" means that the target molecule comprises at least 30% of the total protein present, although the target molecule can comprise at least 50% of the total protein, or 80%; of the total protein, or 90% or 95% of the total protein, or more. A method such as gel electrophoresis and silver staining can be used to determine the relative amount of a target molecule in a sample, following a purification protocol, and, therefore, can be used to identify a substantially isolated target molecule.

The skilled artisan will recognize that a substantially isolated target molecule can be used as an immunogen to obtain antibodies that specifically bind the target molecule. As used herein, the term "antibody" is used in its broadest sense to include polyclonal and monoclonal antibodies, as well as antigen binding fragments of such antibodies. With regard to an antibody of the invention, which specifically binds a target molecule targeted by a tumor homing molecule, the term "antigen" means the target molecule polypeptide or peptide portion thereof. An antibody or antigen binding fragment of an antibody that binds a target molecule is characterized by having specific binding activity for the target molecule or a peptide portion thereof of at least about $1 \times 10^5$ M$^{-1}$, preferably at least about $1 \times 10^6$ M$^{-1}$, and more preferably at least about $1 \times 10^{-8}$ M$^{-1}$. Thus, Fab, F(ab')$_2$, Fd and Fv fragments of the antibody, which retain specific binding activity for a target molecule, which is expressed by angiogenic vasculature, are included within the definition of an antibody.

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275–1281 (1989), which is incorporated herein by reference. These and other methods of making, for example, chimeric, humanized, CDR-grafted, single chain, and bifunctional antibodies are well known to those skilled in the art (Winter and Harris, *Immunol. Today* 14:243–246 (1993); Ward et al., *Nature* 341:544–546 (1989); Hilyard et al., *Protein Engineering: A practical approach* (IRL Press 1992); Borrabeck, *Antibody Engineering*, 2d ed. (Oxford University Press 1995); each of which is incorporated herein by reference; see, also, Harlow and Lane, supra, 1988).

Antibodies that specifically bind a target molecule of the invention can be raised using as an immunogen a substantially isolated target molecule, which can be obtained as disclosed herein, or a peptide portion of the target molecule, which can be obtained, for example, by enzymatic degradation of the target molecule and gel purification. A non-immunogenic peptide portion of a target molecule can be made immunogenic by coupling the hapten to a carrier molecule such as bovine serum albumin (BSA) or keyhole limpet hemocyanin (KLH). Various other carrier molecules and methods for coupling hapten to a carrier molecule are well known in the art and described, for example, by Harlow and Lane, supra, 1988).

Particularly useful antibodies of the invention are those that bind to the tumor homing molecule binding site on the target molecule, such antibodies being readily identifiable by detecting competitive inhibition of binding of the antibody and the particular tumor homing molecule that binds to the target molecule. Conversely, antibodies that bind to an epitope of the target molecule that is not involved in binding the tumor homing molecule also are valuable, since such antibodies, which, themselves, can be "tumor homing molecules," can be bind to target molecules having another tumor homing molecule bound thereto.

An antibody that specifically binds a target molecule, for example, the NGR receptor, is useful for determining the presence or level of the target molecule in a tissue sample, which can be a lysate or a histological section. The identification of the presence or level of the target molecule in the sample can be made using well known immunoassay and immunohistochemical methods (Harlow and Lane, supra, 1988). An antibody specific for a target molecule also can be used to substantially isolate the target molecule from a sample. In addition, an antibody of the invention can be used in a screening assay to identify, for example, peptidomimetics of a tumor homing molecule that bind to the target molecule or as a tool for tumor targeting.

Upon obtaining a target molecule, which, due to the nature of a tumor homing molecule, is expressed in angiogenic vasculature, for example, the angiogenic vasculature in a tumor, the naturally occurring ligand for the target molecule, where it exists, can be identified. Methods for identifying a ligand for such a target molecule, which is akin to an "orphan receptor," are well known in the art and include, for example, screening biological samples to identify the ligand. A convenient screening assay to identify a natural ligand for the target molecule can utilize the ability of a putative natural ligand to competitively inhibit the binding to the target molecule of a tumor homing molecule that specifically binds the target molecule, for example, the tumor homing peptide used to obtain the substantially isolated target molecule.

A screening assay comprising a competitive binding assay for the target molecule and, for example, the natural ligand for the target molecule or a tumor homing peptide that specifically binds the target molecule, also provides a means to identify peptidomimetics of a tumor homing molecule. As discussed above, such peptidomimetics can provide advantages over tumor homing peptides in that they can be small, relatively stable for storage, conveniently produced in suitable quantities, and capable of being administered orally. A peptidomimetic of a tumor homing peptide can be identified by screening libraries of peptidomimetics in a competitive binding assay as described above.

The disclosed in vivo panning method can be used to detect four different kinds of target molecules in tumors. First, because tumor vasculature undergoes active angiogenesis, target molecules that are characteristic of angiogenic vasculature, in general, or angiogenic tumor vasculature, in particular, can be identified. Second, vascular target molecules that are characteristic of the tissue of origin of the tumor can be identified. Third, target molecules that are expressed in the vasculature of a particular type of tumor can be identified. Fourth, tumor stroma or tumor cell target molecules can be identified due to the fenestrated nature of tumor vasculature, which allows the potential tumor homing molecules to leave the circulation and contact the tumor parenchyma.

As further disclosed herein, some, but not all, tumor homing molecules also can home to angiogenic vasculature that is not contained within a tumor. For example, tumor homing molecules containing either the RGD motif or the GSL motif also homed effectively to retinal neovasculature (Smith et al., *Invest. Ophthamol. Vis. Sci.* 35:101–111 (1994), which is incorporated herein by reference), whereas tumor homing peptides containing the NGR motif accumulated to a lesser extent in retinal neovasculature than in tumor vasculature. Thus, the present invention also provides peptides that home to nontumor angiogenic vasculature as well as peptides that home preferentially to tumor vasculature compared to non-tumor neovasculature. Furthermore, these results indicate that tumor vasculature express target molecules that are not substantially expressed by other kinds of angiogenic vasculature. Thus, the present invention provides a means to identify target molecules expressed specifically by angiogenic vasculature present in a tumor, as well as for target molecules expressed by angiogenic vasculature not associated with a tumor. Methods as disclosed herein can be used to distinguish such homing peptides and to isolate the various target molecules.

As an alternative to using a tumor sample to obtain the target molecule, extracts of cultured tumor cells or endothelial cells, depending on which cell type expresses the target molecule, can be used as the starting material in order to enhance the concentration of the target molecule in the sample. It is recognized, however, that the characteristics of such cells can change upon adaptation to tissue culture. Thus, care must be exercised if such a preselection step is attempted. The presence of the target molecule can be established, for example, by using phage binding and cell attachment assays (see, for example, Barry et al., supra, 1996).

A cell line expressing a particular target molecule can be identified and surface iodination of the cells can be used to label the target molecule. The cells then can be extracted, for example, with octylglucoside and the extract can be fractionated by affinity chromatography using a tumor homing peptide (see Tables 1 and 2) coupled to a matrix such as SEPHAROSE (see Hermanson, supra, 1996). The purified target molecule can be microsequenced and antibodies can be prepared. If desired, oligonucleotide probes can be prepared and used to isolate cDNA clones encoding the target molecule. Alternatively, an anti-target molecule antibody can be used to isolate a cDNA clone from an expression library (see Argraves et al., *J. Cell Biol.* 105:1183–1190 (1987), which is incorporated herein by reference).

As an alternative to isolating the target molecule, a nucleic acid encoding the target molecule can be isolated using a mammalian cell expression cloning system such as the COS cell system. An appropriate library can be prepared, for example, using mRNA from primary tumor cells. The nucleic acids can be cloned into the pcDNAIII vector (Invitrogen), for example. Cells expressing a cDNA for the target molecule can be selected by binding to the tumor homing peptide. Purified phage can be used as the carrier of the peptide and can be attached to magnetic beads coated, for example, with anti-M13 antibodies (Pharmacia Biotech; Piscataway N.J.). Cells that bind to the peptide coating can be recovered using a magnet and the plasmids can be isolated. The recovered plasmid preparations then can be divided into pools and examined in COS cell transfections. The procedure can be repeated until single plasmids are obtained that can confer upon the COS cells the ability to bind the tumor homing peptide.

The following examples are intended to illustrate but not limit the present invention.

EXAMPLE I

In Vivo Panning

This example demonstrates methods for preparing a phage library and screening the library using in vivo panning to identify phage expressing peptides that home to a tumor.

A. Preparation of Phage Libraries

Phage display libraries were constructed using the fuse 5 vector as described by Koivunen et al. (supra, 1995; Koivunen et al., supra, 1994b). Libraries encoding peptides designated $CX_5C$ (SEQ ID NO:9), $CX_6C$ (SEQ ID NO:10), $CX_7C$ (SEQ ID NO:11) and $CX_3CX_3CX_3C$ (SEQ ID NO:12) were prepared, where "C" indicates cysteine and "$X_N$" indicates the given number of individually selected amino acids. These libraries can display cyclic peptides when at least two cysteine residues are present in the peptide. In addition, a library that did not contain defined cysteine residues also was constructed. Such a library results in the production primarily of linear peptides, although cyclic peptides also can occur due to random probability.

A biased library based on the sequence CXXXNGRXX (SEQ ID NO:13) also was constructed. Furthermore, in some cases the CXXXNGRXX (SEQ ID NO:13) library was further biased by the incorporation of cysteine residues flanking the NGR sequence, i.e., CXXCNGRCX (SEQ ID NO:14; see Table 1).

The libraries containing the defined cysteine residues were generated using oligonucleotides constructed such that "C" was encoded by the codon TGT and "$X_N$" was encoded by NNK, where "N" is equal molar mixtures of A, C, G and T, and where "K" is equal molar mixtures of G and T. Thus, the peptide represented by $CX_5C$ (SEQ ID NO:9) can be represented by an oligonucleotide having the sequence TGT (NNK)$_5$TGT (SEQ ID NO:206). Oligonucleotides were made double stranded by 3 cycles of PCR amplification, purified and ligated to the nucleic acid encoding the gene III protein in the fuse 5 vector such that, upon expression, the peptide is present as a fusion protein at the N-terminus of the gene III protein.

The vectors were transfected by electroporation into MC1061 cells. Bacteria were cultured for 24 hr in the presence of 20 μg/ml tetracycline, then phage were collected from the supernatant by precipitation twice using polyethylene glycol. Each library contained about 5×10$^9$ to 5×10$^{14}$ transducing units (TU; individual recombinant phage).

B. In Vivo Panning of Phage

Tumors were transplanted into mice as described in Examples II and III, below. A mixture of phage libraries containing 1×10$^9$ to 1×10$^{14}$ TU was diluted in 200 μl DMEM and injected into the tail vein of anesthetized mice (AVERTIN (0.015 ml/g); see U.S. Pat. No. 5,622,699; Pasqualini and Ruoslahti, supra, 1096). After 1–4 minutes, mice were snap frozen in liquid nitrogen. To recover the phage, carcasses were partially thawed at room temperature for 1 hr, tumors and control organs were collected and weighed, then were ground in 1 ml DMEM-PI (DMEM containing protease inhibitors (PI); phenylmethylsulfonyl fluoride (PMSF; 1 mM), aprotinin (20 μg/ml), leupeptin (1 μg/ml)).

Alternatively, following introduction of a library into a mouse, circulation of the library is terminated by perfusion through the heart. Briefly, mice were anesthetized with AVERTIN, then the heart was exposed and a 0.4 mm needle connected through a 0.5 mm cannula to a 10 cc syringe was inserted into the left ventricle. An incision was made on the right atrium and 5 to 10 ml of DMEM was slowly administered, perfusing the whole body over about a 5 to 10 min period. Efficiency of the perfusion was monitored directly by histologic analysis.

Tumor and organ samples were washed 3 times with ice cold DMEM-PI containing 1% bovine serum albumin (BSA), then directly incubated with 1 ml K9-kan bacteria for 1 hr. Ten ml NZY medium containing 0.2 μg/ml tetracycline (NZY/tet) was added to the bacterial culture, the mixture was incubated in a 37° C shaker for 1 hr, then 10 μl or 100 μl aliquots were plated in agar plates containing 12.5 μg/ml tetracycline (tet/agar).

Individual colonies containing phage recovered from a tumor were grown for 16 hr in 5 ml NZY/tet. The bacterial cultures obtained from the individual colonies were pooled and the phage were purified and re-injected into mice as described above for a second round of in vivo panning. In general, a third round of panning also was performed. Phage DNA was purified from individual bacterial colonies obtained from the final round of in vivo panning and the DNA sequences encoding the peptides expressed by selected phage were determined (see Koivunen et al., supra, 1994b).

EXAMPLE II

Identification of Tumor Homing Peptides by In Vivo Panning Against a Breast Tumor This example demonstrates that in vivo panning can be performed against a breast tumor to identify tumor homing peptides that home to various tumors.

Human 435 breast carcinoma cells (Price et al., supra (1990)) were inoculated into the mammary fat pad of nude mice. When the tumors attained a diameter of about 1 cm, either a phage targeting experiment was performed, in which phage expressing a specific peptide were administered to the tumor bearing mouse, or in vivo panning was performed.

The breast tumor bearing mice were injected with 1×10$^9$ phage expressing a library of CX$_3$CX$_3$CX$_3$C (SEQ ID NO:12) peptides, where X$_3$ indicates three groups of independently selected, random amino acids. The phage were allowed to circulate for 4 min, then the mice were anesthetized, snap frozen in liquid nitrogen while under anesthesia, and the tumor was removed. Phage were isolated from the tumor and subjected to two additional rounds of in vivo panning.

Following the third round of panning, phage were quantitated and the peptide sequences expressed by the cloned phage were determined. The cloned phage expressed various different peptides, including those shown in Table 1. Similarly, CX$_7$C (SEQ ID NO:11) and CX$_5$C (SEQ ID NO:9) libraries were screened and breast tumor homing peptides were identified (Table 1). These results demonstrate that in vivo panning against a breast tumor can identify tumor homing molecules.

TABLE 1

PEPTIDES FROM PHAGE RECOVERED FROM HUMAN BREAST CANCER

| | | |
|---|---|---|
| CGRECPRLCQSSC (2*) | | CNGRCVSGCAGRC (3) |
| CGEACGGQCALPC (20) | | IWSGYGVYW (21) |
| PSCAYMCIT (22) | | WESLYFPRE (23) |
| SKVLYYNWE (24) | | CGLMCQGACFDVC (25) |
| CERACRNLCREGC (26) | | CPRGCLAVCVSQC (27) |
| CKVCNGRCCG (28) | CEMCNGRCMG (29) | CPLCNGRCAL (30) |
| CPTCNGRCVR (31) | CGVCNGRCGL (32) | CEQCNGRCGQ (33) |
| CRNCNGRCEG (34) | CVLCNGRCWS (35) | CVTCNGRCRV (36) |
| CTECNGRCQL (37) | CRTCNGRCLE (38) | CETCNGRCVG (39) |
| CAVCNGRCGF (40) | CRDLNGRKVM (41) | CSCCNGRCGD (42) |
| CWGCNGRCRM (43) | CPLCNGRCAR (44) | CKSCNGRCLA (45) |
| CVPCNGRCHE (46) | CQSCNGRCVR (47) | CRTCNGRCQV (48) |
| CVQCNGRCAL (49) | CRCCNGRCSP (50) | CASNNGRVVL (51) |
| CGRCNGRCLL (52) | CWLCNGRCGR (53) | CSKCNGRCGH (54) |
| CVWCNGRCGL (55) | CIRCNGRCSV (56) | CGECNGRCVE (57) |
| CEGVNGRRLR (58) | CLSCNGRCPS (59) | CEVCNGRCAL (60) |
| CGSLVRC (5) | GRSQMQI (61) | HHTRFVS (62) |
| SKGLRHR (63) | VASVSVA (64) | WRVLAAF (65) |
| KMGPKVW (66) | IFSGSRE (67) | SPGSWTW (68) |
| NPRWFWD (69) | GRWYKWA (70) | IKARASP (71) |
| SGWCYRC (72) | ALVGLMR (73) | LWAEMTG (74) |
| CWSGVDC (75) | DTLRLRI (76) | SKSSGVS (77) |
| IVADYQR (78) | VWRTGHL (79) | VVDRFPD (80) |
| LSMFTRP (81) | GLPVKWS (82) | IMYPGWL (83) |
| CVMVRDGDC (84) | CVRIRPC (85) | CQLAAVC (86) |
| CGVGSSC (87) | CVSGPRC (88) | CGLSDSC (89) |
| CGEGHPC (90) | CYTADPC (91) | CELSLISKC (92) |
| CPEHRSLVC (93) | CLVVHEAAC (94) | CYVELHC (95) |
| CWRKFYC (96) | CFWPNRC (97) | CYSYFLAC (98) |
| CPRGSRC (99) | CRLGIAC (100) | CDDSWKC (1O1) |
| CAQLLQVSC (102) | CYPADPC (103) | CKALSQAC (104) |
| CTDYVRC (105) | CGETMRC (106) | |

*numbers in parentheses indicate SEQ ID NO:.

EXAMPLE III

In Vivo Targeting of a Phage Expressing an RGD Peptide to a Tumor

Human 435 breast carcinoma cells were inoculated into the mammary fat pad of nude mice. When the tumors attained a diameter of about 1 cm, phage expressing a specific RGD-containing peptide were administered to the tumor bearing mouse. Similar results to those discussed below also were obtained with nude mice bearing tumors formed by implantation of human melanoma C8161 cells or by implantation of mouse B16 melanoma cells.

1×10$^9$ phage expressing the RGD-containing peptide, RGD-4C (CDCRGDCFC; SEQ ID NO:1; see, Koivunen et al., supra, 1995) or control (insertless) phage were injected intravenously (iv) into the mice and allowed to circulate for 4 min. The mice then were snap frozen or perfused through the heart while under anesthesia, and various organs, including tumor, brain and kidney, were removed and the phage present in the organs was quantitated (see U.S. Pat. No. 5,622,699; Pasqualini and Ruoslahti, supra, 1996).

Approximately 2–3 times more phage expressing the RGD-4C (CDCRGDCFC; SEQ ID NO:1) peptide were detected in the breast tumor as compared to brain and kidney, indicating the CDCRGDCFC (SEQ ID NO:1; RGD-4C phage) peptide resulted in selective homing of the phage to the breast tumor. In a parallel study, unselected phage, which express various, diverse peptides, were injected into tumor-bearing mice and various organs were examined for the presence of phage. Far more phage were present in kidney and, to a lesser extent, brain, as compared to the tumor. Thus, the 80-fold more RGD-expressing phage than unselected phage concentrated in the tumor. These results indicate that phage expressing the RGD-containing peptide home to a tumor, possibly due to the expression of the $\alpha_v\beta_3$ integrin on blood vessels forming in the tumor.

Specificity of the breast tumor homing peptide was demonstrated by competition experiments, in which coinjection of 500 μg free peptide, ACDCRGDCFCG (SEQ ID NO:16; see Pasqualini et al., supra, 1997) with the phage expressing the tumor homing peptide reduced the amount of phage in the tumor by about tenfold, whereas coinjection with the inactive control peptide, GRGESP (SEQ ID NO:17) essentially had no effect. These results demonstrate that phage displaying a peptide that can bind to an integrin expressed on angiogenic vasculature can selectively home in vivo to an organ or tissue such as a tumor containing such vasculature.

EXAMPLE IV

In Vivo Targeting of Phage Expressing Tumor Homing Peptides

This example describes in vivo targeting of phage expressing peptides that home to tumors.

One of the peptides that accumulated in tumors was derived from a library with the structure $CX_3CX_3CX_3C$ (Arap et al., Science 279:377–380 (1998), which is incorporated herein by reference). This peptide, C NGRCVSGCAGRC (SEQ ID NO:3), contained the sequence NGR (asparagine-glycine-arginine), which has been identified previously as a weak cell adhesion motif (Koivunen et al., J. Biol. Chem. 268:20205–20210 (1993); Healy et al., Biochem. 34:3948–3955 (1995), each of which is incorporated herein by reference). Two other peptides that contain the NGR motif, but are otherwise entirely different from the CNGRCVSGCAGRC (SEQ ID NO:3) peptide, were tested for the ability to home to various tumors in vivo. One of them is a linear peptide, NGRAHA (SEQ ID NO:6) (Koivunen et al. supra (1993) and the other a cyclic one, CVLNGRMEC.

Phage displaying tumor homing peptides were recovered from breast carcinoma xenografts. Briefly, phage were injected at $10^9$ transducing units (TU) into the tail vein of mice bearing size-matched MDA-MB-435 derived tumors (~1000 mm$^3$) and recovered after perfusion. The mean number of phage recovered from the tumor or control tissue (brain) and the standard error of the mean (SEM) from triplicate platings are shown in FIG. 1. FIG. 1A, left panel, shows recovery of CNGRCVSGCAGRC (SEQ ID NO:3) phage from tumor (filled bars) and brain (striped bars). The minimal cyclic NGR peptide from the CNGRCVSG-CAGRC (SEQ ID NO:3) phage (CNGRC) was synthesized, and, when 500 μg of CNGRC (SEQ ID NO:8) peptide was co-injected with the phage, the peptide inhibited the accumulation of CNGRCVSGCAGRC (SEQ ID NO:3) phage as shown in FIG. 1B. The CNGRC (SEQ ID NO:8) peptide also inhibited the accumulation of the two other NGR-displaying phage in breast carcinoma xenografts. FIG. 1A, middle panel, shows recovery of CGSLVRC (SEQ ID NO:5) phage and inhibition of tumor homing by the soluble peptide CGSLVRC (SEQ ID NO:5) (500 μg). FIG. 1A, right panel, shows recovery of RGD-4C (CDCRGDCFC; SEQ ID NO:1) phage (positive control) and unselected phage library mix (negative control).

In FIG. 1B, left panel, increasing amounts of the RGD-4C (CDCRGDCFC; SEQ ID NO:1) soluble peptide were injected with the CNGRCVSGCAGRC (SEQ ID NO:3) phage. In FIG. 1B, right panel, increasing amounts of the CNGRC (SEQ ID NO:8) soluble peptide were injected with the RGD-4C (CDCRGDCFC; SEQ ID NO:1) phage. Inhibition of the CNGRCVSGCAGRC (SEQ ID NO:3) phage homing by the CNGRC (SEQ ID NO:8) peptide is shown in FIG. 1A. Inhibition of the RGD-4C (CDCRGDCFC; SEQ ID NO:1) phage by the RGD-4C (CDCRGDCFC; SEQ ID NO:1) peptide is described above.

As shown in FIG. 1, the CNGRCVSGCAGRC (SEQ ID NO:3) phage homed specifically to the xenografted human breast carcinomas. Similar results were obtained with the other NGR-displaying phage. The tumor homing was not dependent on the tumor type or on the species of the tumor: the phage accumulated selectively in the human breast carcinoma used in the selection as shown in FIG. 1A, as well as in a human Kaposi's sarcoma and in a mouse melanoma (data not shown).

As shown in FIG. 1B, left panel, the RGD-4C (CDCRGDCFC; SEQ ID NO:1) phage homes selectively to the breast cancer tumor, and its homing is readily inhibited by free RGD-4C peptide (see above). However, the tumor homing of RGD-4C phage was not inhibited by the CNGRC peptide (FIG. 1B, left panel), even when the peptide was used in amounts higher than those that inhibited the homing of the NGR phage (FIG. 1A, left panel). As shown in FIG. 1B, right panel, the tumor homing of the NGR phage was partially inhibited by the RGD-4C (CDCRGDCFC; SEQ ID NO:1) peptide, but this peptide was 5–10 times less potent than the CNGRC peptide. An unrelated cyclic peptide, GACVFSIAHECGA (SEQ ID NO:19), had no effect in the tumor homing ability of either phage (data not shown). In sum, these results indicate that the two peptides displaying RGD and NGR bind to different receptor sites in tumor vasculature, although the RGD and NGR receptor sites can be related.

To further characterize and quantitate the tumor homing ability of phage expressing peptides, CNGRC (SEQ ID NO:8), RGD-4C (CDCRGDCFC; SEQ ID NO:1), and control phage (insertless fd-amp and fd-tet) were injected at $10^9$ transducing units (TU) into the tail vein of mice bearing size-matched, MDA-MB-435-derived tumors (~1000 mm$^3$) and recovered from tumors and brain tissue after perfusion. An insertless phage with a different selective marker (ampicillin instead of tetracycline) was co-injected with the NGR phage at the same input to assess specificity within the same tumor-bearing animal. The ratios were calculated using the number of co-injected control ampicillin-resistant phage recovered from the same tissues. The phage were quantitated from triplicate platings on tetracycline (the homing phage) or ampicillin (control phage) selective plates.

Various additional control phage were injected separately into tumor-bearing mice. These controls included: fd-tet phage without insert; unselected phage library mixtures; phage selected and shown to home to other normal vascular beds; and phage displaying peptides that were unrelated to NGR. The RGD-4C (CDCRGDCFC; SEQ ID NO:1) phage served as a positive control.

Over 10-fold more NGR phage than control ampicillin-resistant phage accumulated in the tumor in the co-injection experiments (FIG. 2). The RGD-4C (CDCRGDCFC; SEQ ID NO:1) phage also bound selectively to the tumors. In contrast, more ampicillin phage than NGR phage were recovered from brain (FIG. 2) and other control organs tested. Moreover, co-injection of the NGR-phage with a 10-fold excess of phage particles engineered to be non-infective did not affect tumor homing. The inclusion of excess non-infective phage particles did decrease the trapping of phage in organs containing reticuloendothelial tissue such as the spleen and the liver.

EXAMPLE V

Immunohistochemical Analysis of Tumor Homing Peptides

This example provides a method of identifying the localization of tumor homing molecules by immunohistochemical examination.

Localization of phage expressing a tumor homing peptide was identified by immunochemical methods in histologic sections obtained either 5 min or 24 hr after administration of phage expressing a tumor homing peptide ("peptide-phage") to a tumor bearing mouse (FIG. 3). For samples obtained 5 min following administration of the peptide-phage, mice were perfused with DMEM and various organs, including the tumor, were removed and fixed in Bouin's solution. For samples obtained at 24 hr, no peptide-phage remains in the circulation and, therefore, perfusion was not required. Histologic sections were prepared and reacted with anti-M13 (phage) antibodies (Pharmacia Biotech; see U.S. Pat. No. 5,622,699; Pasqualini and Ruoslahti, supra, 1996). Visualization of the bound anti-M13 antibody was performed using a peroxidase-conjugated second antibody (Sigma; St. Louis Mo.) according to the manufacturer's instructions.

As discussed in Example III, phage expressing the tumor homing peptide, RGD-4C (CDCRGDCFC; SEQ ID NO:1; also designated "RGD phage"), were administered intravenously to mice bearing the breast tumor. In addition, the RGD phage were administered to mice bearing a mouse melanoma or a human Kaposi's sarcoma. Circulation of the phage was terminated and mice were sacrificed as described above and samples of the tumor and of skin adjacent to the tumor, brain, kidney, lung and liver were collected. Immunohistochemical staining for the phage showed accumulation of the RGD phage in the blood vessels present in the breast tumor as well as in the melanoma and the Kaposi's sarcoma, whereas little or no staining was observed in the control organs.

Similar experiments were performed using phage expressing the tumor homing peptide, CNGRCVSG-CAGRC (SEQ ID NO:3; "NGR phage"), which was identified by in vivo panning against a tumor formed by the MDA-MB-435 breast carcinoma. In these experiments, NGR phage or control phage, which do not express a peptide, were administered to mice bearing tumors formed by the MDA-MB-435 breast carcinoma or by a human SLK Kaposi's sarcoma xenograft, then the mice were sacrificed as described above and tumors were collected as well as control organs, including brain, lymph node, kidney, pancreas, uterus, mammary fat pad, lung, intestine, skin, skeletal muscle, heart and epithelium of the renal calices, bladder and ureter (see FIG. 3). Histological samples were prepared and examined by immunostaining as described above.

Figure 3C:
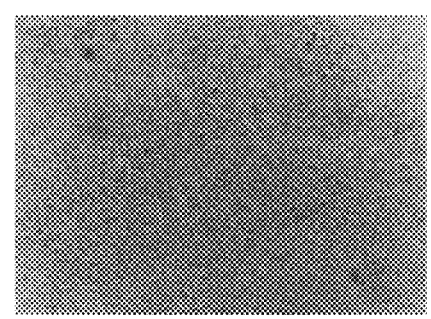
Figure 3G:
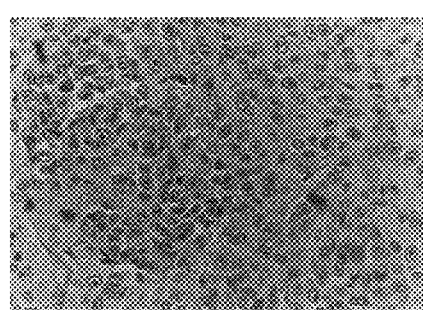
Figure 3D:
Figure 3H:
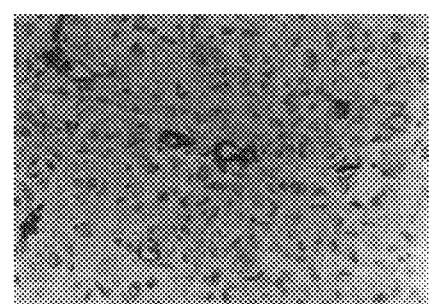
Figure 3I:
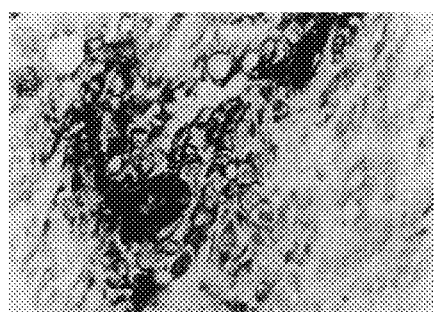
Figure 3M:
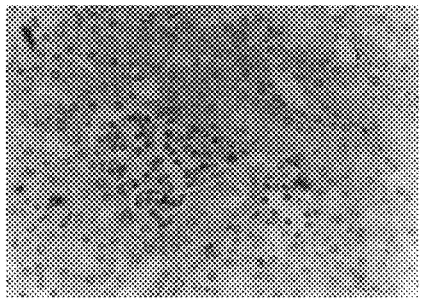
Figure 3J:
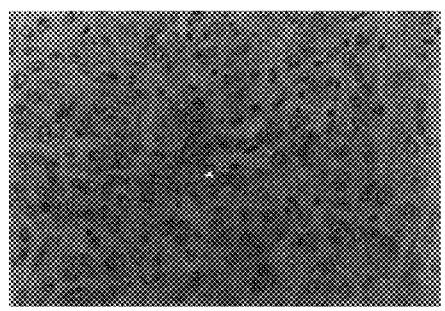
Figure 3N:
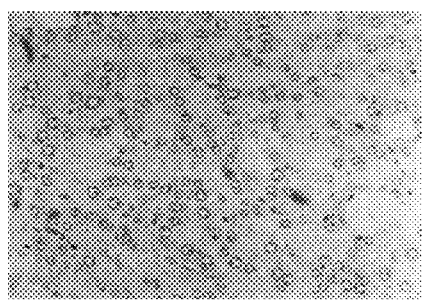
Figure 3K:
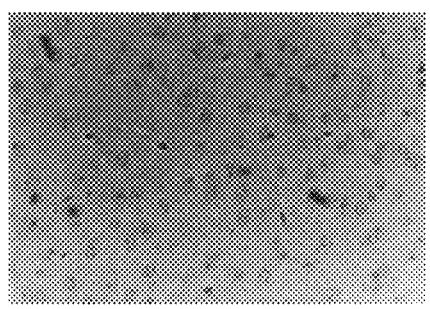
Figure 3O:
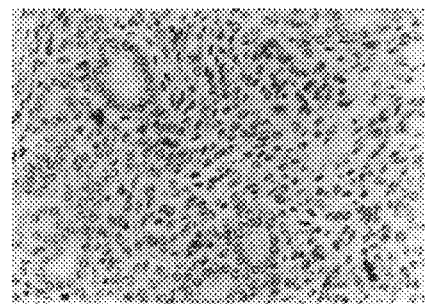
Figure 3L:
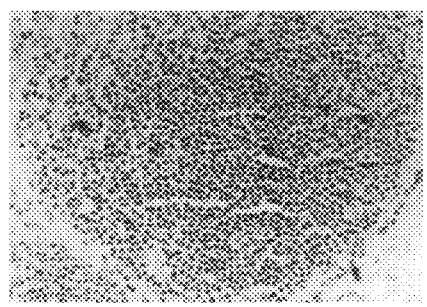
Figure 3P:
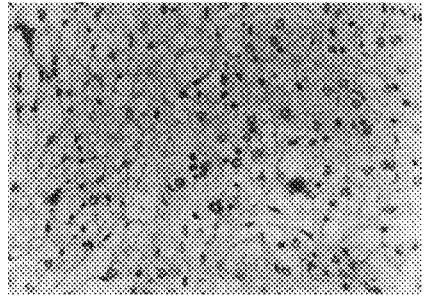
Figure 3Q:
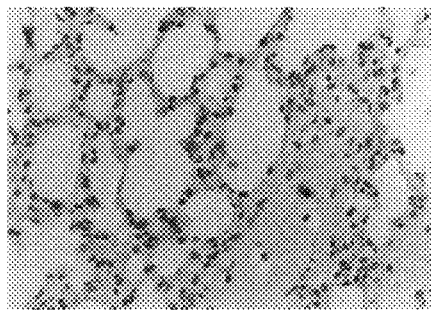
Figure 3T:
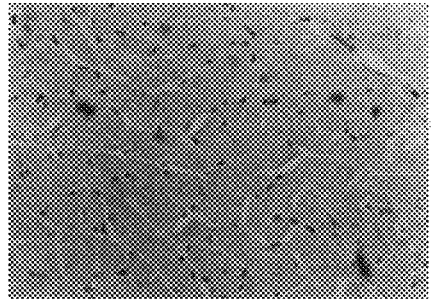
Figure 3R:
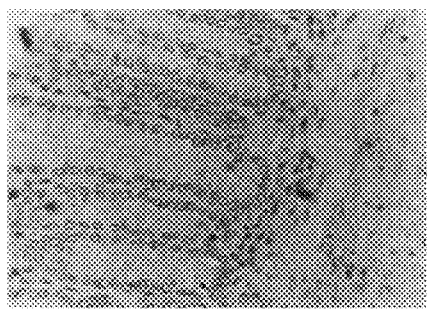
Figure 3U:
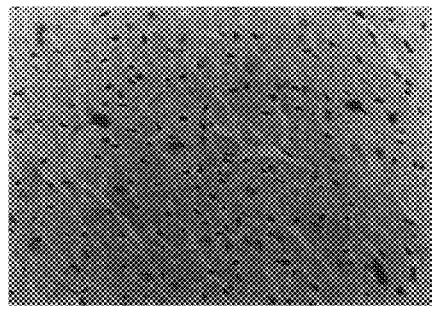
Figure 3S:
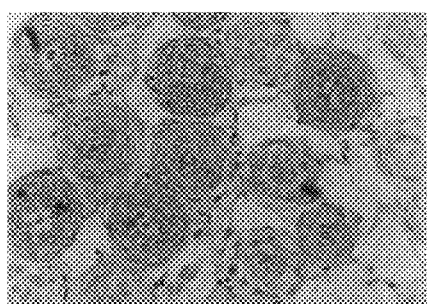
Figure 3V:
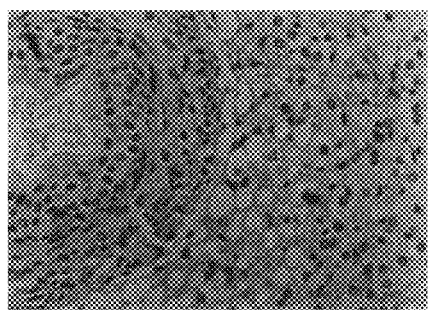

In samples obtained from mice sacrificed 4 min after administration of the NGR phage, immunostairing of the vasculature of both the breast tumor (FIG. 3E) and the Kaposi's sarcoma (FIG. 3H) was observed. Very little or no staining was observed in the endothelium of the these tumors in mice administered an insertless control phage (FIGS. 3G and 3J, respectively). In the samples obtained from mice sacrificed 24 hr after administration of the NGR phage, staining of the tumor samples appeared to have spread outside of the vessels, into the breast tumor parenchyma (FIGS. 3B and 3F) and the Kaposi's sarcoma parenchyma (FIGS. 3D and 3I). Again, little or no staining was observed in samples prepared from these tumors in mice administered the insertless control phage (FIGS. 3A and 3C, respectively). In addition, little or no staining was observed in various control organs in mice administered the NGR phage (FIGS. 3K to 3V).

In other experiments, similar results were obtained following administration of phage expressing the NGR tumor homing peptides, NGRAHA (SEQ ID NO:6) or CVLN-GRMEC (SEQ ID NO:7), to tumor bearing mice. Also, as discussed below, similar results were obtained using phage expressing the GSL tumor homing peptide, CLSGSLSC (SEQ ID NO:4), which was identified by in vivo panning of a melanoma (see Example VI, below).

These results demonstrate that tumor homing peptides selectively home to tumors, particularly to the vasculature in the tumors and that tumor homing peptides identified, for example, by in vivo panning against a breast carcinoma also selectively home to other tumors, including Kaposi's sarcoma and melanoma. In addition, these results demonstrate that immunohistochemica analysis provides a convenient assay for identifying the localization of phage expressing tumor homing peptides.

EXAMPLE VI

Identification of Tumor Homing Peptides by In Vivo Panning Against a Melanoma Tumor The general applicability of the in vivo panning method to identify tumor homing peptides was examined by performing in vivo panning against an implanted mouse melanoma tumor.

Mice bearing a melanoma were produced by implantation of B16B15b mouse melanoma cells, which produce highly vascularized tumors. B16B15b mouse melanoma cells were injected subcutaneously into the mammary fat pad of nude mice (2 months old) and tumors were allowed to grow until the diameter was about 1 cm. In vivo panning was performed as disclosed above. Approximately $1 \times 10^{12}$ transducing units of phage expressing the $CX_5C$ (SEQ ID NO:9), $CX_6C$ (SEQ ID NO:10) or $CX_7C$ (SEQ ID NO:11) library were injected, iv, and allowed to circulate for 4 min. Mice then were snap frozen in liquid nitrogen or perfused through the heart while under anesthesia, tumor tissue and brain (control organ) were removed, and phage were isolated as described above. Three rounds of in vivo panning were performed.

The amino acid sequences were determined for the inserts in 89 cloned phage recovered from the B16B15b tumors. The peptides expressed by these phage were represented by two predominant sequences, CLSGSLSC (SEQ ID NO:4; 52% of the clones sequenced) and WGTGLC (SEQ ID NO:18; 25% of the clones; see Table 2). Reinfection of phage expressing one of the selected peptides resulted in approximately three-fold enrichment of phage homing to the tumor relative to brain.

TABLE 2

PEPTIDES FROM PHAGE RECOVERED FROM MOUSE B16B15b MELANOMA

| | | |
|---|---|---|
| CLSGSLSC (4*) | GICKDDWCQ (107) | TSCDPSLCE (108) |
| KGCGTRQCW (109) | YRCREVLCQ (110) | CWGTGLC (111) |
| WSCADRTCM (112) | AGCRLKSCA (113) | SRCKTGLCQ (114) |
| PICEVSRCW (115) | WTCRASWCS (116) | GRCLLMQCR (117) |
| TECDMSRCM (118) | ARCRVDPCV (119) | CIEGVLGGC (120) |
| CSVANSC (121) | CSSTMRC (122) | SIDSTTF (123) |
| GPSRVGG (124) | WWSGLEA (125) | LGTDVRQ (126) |
| LVGVRLL (127) | GRPGDJW (128) | TVWNPVG (129) |
| GLLLVVP (130) | FAATSAE (131) | WCCRQFN (132) |
| VGFGKAL (133) | DSSLRLP (134) | KLWCAMS (135) |
| SLVSFLG (136) | GSFAFLV (137) | IASVRWA (138) |
| TWGHLRA (139) | QYREGLV (140) | QSADRSV (141) |
| YMFWTSR (142) | LVRRWYL (143) | TARGSSR (144) |
| TTREKNL (145) | PKWLLFS (146) | LRTNVVH (147) |
| AVMGLAA (148) | VRNSLRN (149) | |

*numbers in parentheses indicate SEQ ID NO:.

Localization of the phage expressing a tumor homing peptide in the mouse organs also was examined by immunohistochemical staining of the tumor and various other tissues (see Example V). In these experiments, 1×10$^9$ pfu of a control (insertless) phage or a phage expressing the tumor homing peptide, CLSGSLSC (SEQ ID NO:4), were injected, iv, into tumor bearing mice and allowed to circulate for 4 min.

Immunostaining was evident in the melanoma obtained from a mouse injected with phage expressing the CLSGSLSC (SEQ ID NO:4) tumor homing peptide. Staining of the melanoma generally was localized to the blood vessels within the tumor, although some staining also was present in the tumor parenchyma. Essentially no staining was observed in a tumor obtained from a mouse injected with the insertless control phage or in skin or in kidney samples obtained from mice injected with either phage. However, immunostaining was detected in the liver sinusoids and in spleen, indicating that phage can be trapped nonspecifically in organs containing RES.

Using similar methods, in vivo panning was performed in mice bearing a SLK human Kaposi's sarcoma. Tumor homing peptides were identified and are disclosed in Table 3. Together, these results demonstrate that the in vivo panning method is a generally applicable method for screening a phage library to identify phage expressing tumor homing peptides.

TABLE 3

PEPTIDES FROM PHAGE RECOVERED FROM HUMAN KAPOSI'S SARCOMA

| | | |
|---|---|---|
| TDCTPSRCT (150*) | SWCQFEKCL (151) | VPCRFKQCW (152) |
| CTAMRNTDC (153) | CRESLKNC (154) | CMEMGVKC (155) |
| VTCRSLMCQ (156) | CNNVGSYC (157) | CGTRVDHC (158) |
| CISLDRSC (159) | CAMVSMED (160) | CYLGVSNC (161) |
| CYLVNVDC (162) | CIRSAVSC (163) | LVCLPPSCE (164) |
| RHCFSQWCS (165) | FYCPGVGCR (166) | ISCAVDACL (167) |

TABLE 3-continued

PEPTIDES FROM PHAGE RECOVERED FROM HUMAN KAPOSI'S SARCOMA

| | | |
|---|---|---|
| EACEMAGCL (168) | PRCESQLCP (169) | RSCIKHQCP (170) |
| QWCSRRWCT (171) | MFCRMRSCD (172) | GICKDLWCQ (173) |
| NACESAICG (174) | APCGLLACI (175) | NRCRGVSCT (176) |
| FPCEGKKCL (177) | ADCRQKPCL (178) | FGCVMASCR (179) |
| AGCINGLCG (180) | RSCAEPWCY (181) | DTCRALRCN (182) |
| KGCGTRQCW (109) | GRCVDGGCT (183) | YRCIARECE (184) |
| KRCSSSLCA (185) | ICLLAHCA (186) | QACPMLLCM (187) |
| LDCLSELCS (188) | AGCRVESC (189) | HTCLVALCA (190) |
| IYCPGQECE (191) | RLCSLYGCV (192) | RKCEVPGCQ (193) |
| EDCTSRFCS (194) | LECVVDSCR (195) | EICVDGLCV (196) |
| RWCREKSCW (197) | FRCLERVCT (198) | RPCGDQACE (199) |
| CNKTDGDEGVTC (15) | | |

*numbers in parentheses indicate SEQ ID NO:.

EXAMPLE VII

Preparation and Characterization of Tumor Homing Peptide/Doxorubicin Conjugates

This example provides methods for conjugating a moiety such as the chemotherapeutic agent, doxorubicin, to a tumor homing peptide and for characterizing the conjugation product.

The peptides CNGRC (SEQ ID NO:8), CDCRGDCFC (SEQ ID NO:1; RGD-4C; Koivunen et al., supra, 1995; Pasqualini et al., supra, 1997), CGSLVRC (SEQ ID NO:5) and GACVFSIAHECGA (SEQ ID NO:19) were synthesized, cyclized under high dilution and purified to homogeneity by HPLC. Conjugation of the peptides to doxorubicin (Aldrich; Milwaukee Wis.) was performed using 1-ethyl-3-(3-dimethylaminopropyl)carbodiimide hydrochloride (EDC; Sigma; St. Louis Mo.) and N-hydroxysuccinimide (NHS; Sigma) as described (Bauminger and Wilchek, supra, 1980; Harlow and Lane, supra, 1988; Hurwitz et al., supra, 1975). Unreacted doxorubicin and peptide were re:moved from the doxorubicin/peptide conjugates by SEPHADEX G25 column chromatography using phosphate buffered saline. The conjugates were lyophilized for storage and were resuspended in sterile water prior to use.

Doxorubicin concentration of the conjugates (see Example VI) was determined by measuring the optical absorbance of the solution at 490 nm in a standard spectrophotometer; this wavelength detects only the doxorubicin, not the peptides. A calibration curve for doxorubicin was generated and used to calculate the concentration prior to use. Conjugation of doxorubicin to the various peptides did not affect this curve. This procedure ensures that each of the administered conjugates contained the same amounts of doxorubicin equivalent.

HPLC, mass spectrometry, capillary electrophoresis and NMR analyses were performed to characterize the conjugates. HPLC-fluorescence was performed using an INTER-SIL ODS-2 column (4.6×150 mm) and a mobile phase composed of 0.08% triethanolamine/0.02% phosphoric acid (85%)/27% acetonitrile at 1 ml/min. Fluorescence detection was performed with excitation at 490 nm and emission at 560 nm wavelength and the retention time (RT) and the area under the curves (AUC) for doxorubicin (dox) and for the major peaks was determined. Each of the conjugates has a unique retention time, depending on the peptide, as follows: doxorubicin/CDCRGDCFC (SEQ ID NO:1), RT 7.4 min, AUC 26%; doxorubicin/CNGRC (SEQ ID NO:8), RT 4.7 min, AUC 56%; and doxorubicin/GACVFSIAHECGA (SEQ ID NO:19), RT 7.7 min, AUC 43%. In comparison, the retention time of doxorubicin is 10.6 min and, in the various reactions, the AUC was about 5%.

Capillary electrophoresis (CE; Liu et al., supra, 1996) was performed in uncoated fused-silica capillaries with 75 μm internal diameter and an effective separation length of 50 cm. The CE detection system was equipped with an UV absorbance detector and an argon laser emitting at 488 nm. The laser beam is transmitted via a fiber optic cable to the detector and illuminates the capillary window and the fluorescence signal is collected through an emission filter. Conjugation of doxorubicin to the peptides changed the electrophoretic characteristics of each of the conjugates, indicating that this method can be used as a fast screening method to identify progress of the conjugation reaction.

An alternative method of conjugating doxorubicin to peptides was also used (Nagy et al., supra 1996; Nagy et al., supra 1998). The doxorubicin/CNGRC conjugate prepared by this method was found to be homogeneous by HPLC. Mass spectrometry showed that the doxorubicin/CNGRC (SEQ ID NO:8) conjugate had one predominant mass number (1192.6), which agreed with the mass predicted from the coupling chemistry (predicted mass 1192.2). Similar results were obtained when the RGD-4C (CDCRGDCFC; SEQ ID NO:1) peptide was coupled to doxorubicin.

One dimensional NMR analysis of the doxorubicin/CNGRC conjugate revealed no evidence of resonances arising from free doxorubicin. Two dimension NMR analysis can allow a determination of the precise molecular structure of the doxorubicin-peptide species.

These results demonstrate that a moiety such as the cancer chemotherapeutic agent, doxorubicin, can be efficiently linked to tumor homing peptides of the invention to produce homogeneous doxorubicin/tumor homing peptide conjugates.

EXAMPLE VIII

Tumor Therapy Using Doxorubicin/Tumor Homing Peptide Conjugates

This example demonstrates that doxorubicin/tumor homing peptide conjugates provide a therapeutic advantage over the use of doxorubicin, alone, for treating tumors.

Doxorubicin concentration of the conjugates (see Example VI) was determined by measuring the optical absorbance of the solution at 490 nm in a standard spectrophotometer; this wavelength detects only the doxorubicin, not the peptides. A calibration curve for doxorubicin was generated and used to calculate the concentration prior to use. Conjugation of doxorubicin to the various peptides did not affect this curve. This procedure ensures that each of the administered conjugates contained the same amounts of doxorubicin equivalent.

In addition, the viability of tumor cells obtained from tumors of mice treated with a tumor homing peptide/doxorubicin conjugate was compared to that of tumors from mice treated with free doxorubicin. In these experiments, breast tumor bearing mice were size matched with regard to the tumors, then treated intravenously with 30 μg equivalent of doxorubicin/RGD-4C (CDCRGDCFC; SEQ ID NO:1) or of free doxorubicin. Five days after treatment, the mice were euthanized and the tumors were removed. The tumor pairs were weighed and ground and the cell suspensions were plated (2 g tumor tissue per 150 mm plate).

Cell numbers were determined at 24 hours and 7 days after plating. Viability of tumor cells from the tumors of mice receiving the doxorubicin/RGD-4C (CDCRGDCFC; SEQ ID NO:1) conjugate was about 3 fold less than cells from tumors of mice treated with the free doxorubicin. These results demonstrate that administration to a tumor bearing mouse of a conjugate comprising a chemotherapeutic agent linked to a tumor homing molecule is more efficacious than administration of the agent, alone, in reducing the viability of tumor cells.

A. In Vitro Characterization of Cytotoxicity

MDA-MB-435 human breast carcinoma cells were plated at $1 \times 10^5$ cells/well in 96 well plates. Cells were incubated with increasing amounts of doxorubicin, the doxorubicin/RGD-4C (CDCRGDCFC; SEQ ID NO:1) conjugate, or the doxorubicin/GACVFSIAHECGA (SEQ ID NO:19; control) conjugate (0.1 to 10 μg/well of doxorubicin-equivalent) for either 30 min or overnight. Following incubation, the agents were removed by extensive washing with PBS, then fresh medium added and incubation was continued. The number of surviving cells was determined at 24 hours with crystal violet staining (see Koivunen et al., supra, 1994).

In cells exposed to free doxorubicin, the doxorubicin/RGD-4C (CDCRGDCFC; SEQ ID NO:1) conjugate, or the doxorubicin/GACVFSIAHECGA (SEQ ID NO:19) for 30 min, cell death was present only in the cultures treated with the doxorubicin/RGD-4C (CDCRGDCFC; SEQ ID NO:1) conjugate. However, if the agents were not removed after 30 min, the cells were killed by all of the treatments after 24 hr. These results indicate that enhanced cellular uptake occurs for the doxorubicin/RGD-4C (CDCRGDCFC; SEQ ID NO:1) conjugate.

B. In Vivo Characterization of Doxorubicin/Tumor Homing Peptide Conjugates

Female 2-month old Balb c nu/nu mice (Harlan Sprague Dawley; San Diego Calif.) were used for these studies and were cared for according to the Burnham Institute animal facility guidelines. MDA-MB-435 breast carcinoma cells (Price et al., supra (1993)) were injected in the mammary fat pad of the nude mice and tumor growth was monitored (Pasqualini et al., supra, 1997). Tumors were allowed to grow to a size of about 1 cm³ (about 5% of the mouse's body weight) before starting the treatment experiments, except for the toxicity experiments as discussed below.

Weekly doxorubicin/peptide conjugate or control treatments (5 μg/mouse/week of doxorubicin-equivalent) were administered intravenously. In some experiments, as indicated, a dose of 30 μg/mouse was administered every 3 weeks. Treatment with doxorubicin, alone, is referred to as "dox control" and treatment with doxorubicin conjugated to the non-tumor homing control peptide, GACVFSIAHECGA (SEQ ID NO:19), is referred to as "conjugate control." The results obtained in the doxorubicin control groups as compared to the conjugate control groups were not significantly different. As an additional control, in some experiments the tumor homing peptide was mixed with doxorubicin, without linking, and the mixture was administered to tumor bearing mice. Such treatment produced results that were not statistically different from those obtained with the above described doxorubicin controls.

Mice were anesthetized with a tribromoethanol-based anesthetic mixture (AVERTIN; Papaioannou and Fox, *Lab. Anim.* 43:189–192 (1993)) before each treatment. Anesthetization facilitated the tail vein injections (final volume, 200 μl) and allowed precise serial three dimensional tumor size measurements. Tumor volume calculations were based on the equation for the volume of an ovaloid: $V = \frac{1}{3}(\pi abc)$, where a, b, and c are ½ of the measured diameters in each of the three dimensions.

At necropsy, MDA-MB-435 tumor-bearing mice treated with the doxorubicin/RGD-4C (CDCRGDCFC; SE-Q ID NO:1) conjugate had significantly smaller tumors (t test, p=0.02), less spread to regional lymph nodes (t test, p<0.0001), a lower incidence of pulmonary metastascis and fewer metastatic lesions (t test, p<0.0001) than the doxorubicin control treated mice. All of the mice treated with the doxorubicin/RGD-4C (CDCRGDCFC; SEQ ID NO:1) conjugate survived beyond the time when the doxorubicin control and conjugate control mice had died (Log-Rank test, p<0.0001; Wilcoxon test, p=0.0007). Essentially the same results were obtained in five separate experiments. These results indicate that a doxorubicin/tumor homing peptide provides a therapeutic advantage over doxorubicin, alone, in reducing the growth of a primary tumor and preventing metastasis of the tumor.

Gross and histopathologic examination was performed on the mice. Many of the tumors in the mice treated with 5 µg doxorubicin equivalent of doxorubicin/RGD-4C (CDCRGDCFC; SEQ ID NO:1) presented marked skin ulceration and tumor necrosis, whereas no such signs were observed in doxorubicin control group or conjugate control group. Histopathological analysis disclosed a pronounced destruction of the vasculature in the tumors treated with doxorubicin/RGD-4C (CDCRGDCFC; SEQ ID NO:1) conjugate as compared to the doxorubicin control group.

In a dose escalation experiment, tumor bearing mice were treated with the doxorubicin/RGD-4C (CDCRGDCFC; SEQ ID NO:1) at 30 µg/mouse every three weeks for three cycles and were observed, without further treatment, for an extended period of time. The doxorubicin/RGD-4C (CDCRGDCFC; SEQ ID NO:1) treated mice all remained alive more than 6 months after the doxorubicin control and conjugate control mice had died. The results indicate that treatment with a doxorubicin/tumor homing peptide conjugate can have a curative effect.

Acute toxicity studies also were performed. In these experiments, mice bearing extremely large tumors (about 25% of body weight) were treated with 200 µg/mouse doxorubicin or doxorubicin/RGD-4C (CDCRGDCFC; SEQ ID NO:1) conjugate. All of the mice treated with the doxorubicin/RGD-4C (CDCRGDCFC; SEQ ID NO:1) conjugate survived for longer than one week, whereas all of the doxorubicin control mice had died within 48 hr of treatment. These results suggest that accumulation of the doxorubicin/RGD-4C (CDCRGDCFC; SEQ ID NO:1) conjugate in the large tumors reduced the circulating level of the conjugated doxorubicin, thus reducing its toxicity.

Similar results were obtained using the doxorubicin/CNGRC (SEQ ID NO:8) conjugate. In each of three series of experiments, tumors in the mice treated with doxorubicin/CNGRC (SEQ ID NO:8) were significantly smaller than tumor is the doxorubicin control and conjugate control groups. Treatment with the doxorubicin/CNGRC (SEQ ID NO:8) conjugate almost completely suppressed tumor growth, whereas free doxorubicin and doxorubicin conjugated to the control peptide had essentially no effect on tumor growth relative to treatment with the vehicle, alone. A marked effect on survival also was observed and some of the doxorubicin/CNGRC (SEQ ID NO:8) treated animals survived for extended periods of time (Log-Rank test, p=0.0064; Wilcoxon test, p=0.0343). In addition, the doxorubicin/CNGRC (SEQ ID NO:8) conjugate was less toxic than free doxorubicin. These results confirm that conjugates comprising a chemotherapeutic agent and a tumor homing molecule provide a therapeutic advantage in treating cancer.

EXAMPLE IX

Interaction of CD13/APN with NGR Ligands

This example describes the interaction of CD13/APN with NGR containing peptides.

The use of phage display peptide libraries to isolate minimal receptor sequences that bind to fibronectin and RCD-containing fibronectin fragments in affinity panning is described in Pasqualini et al., *J. Cell Biol.* 130:1189–1196 (1995), which is incorporated herein by reference. A predominant motif, CWDD(G/L)WLC was obtained and shown to be a structural mimic of an RGD-binding site on integrins (Pasqualini et al., supra, 1995). By searching the protein database for sequences homologous to the W(D/N)DGWL sequence (an RGD-binding peptide, Pasqualini et al., supra, 1995), an identical peptide sequence, except for the flanking cysteines, was found in aminopeptidases. The W(D/N) DGWL sequence was highly conserved in aminopeptidases from bacteria to humans, indicating that this motif represents a functionally relevant domain (Favaloro et al., supra (1988); Rawlings and Barret, *Biochem J.* 290:205–218 (1993), each of which is incorporated herein by reference). CD13/Aminopeptidase N contains the closely related WNDGWL sequence (Look et al., supra (1989); Chen et al., *J. Immunol.* 157:2593–2600 (1996), each of which is incorporated herein by reference).

Binding of CNGRC-Phage to Immobilized CD13/APN

Given that the NGR sequence closely resembles a reverse RGD sequence, NGR-containing phage were tested to determine whether they would bind to CD13/aminopeptidase (CD13/APN). Kaposi's sarcoma tumor cell octylglucoside extracts were used as a source of CD13/APN. Aminopeptidase enzymatic activity was measured in these extracts utilizing Ala-pNA or Leu-pNA as substrates by monitoring the absorbance of the samples at 405 nm (Look et al., supra (1989); Taylor, supra (1993); Amoscato et al., supra (1989), each of which is incorporated herein by reference). The specificity was confirmed by demonstrating inhibition by o-phenanthroline, a specific inhibitor of aminopeptidase N.

Figure 4A:
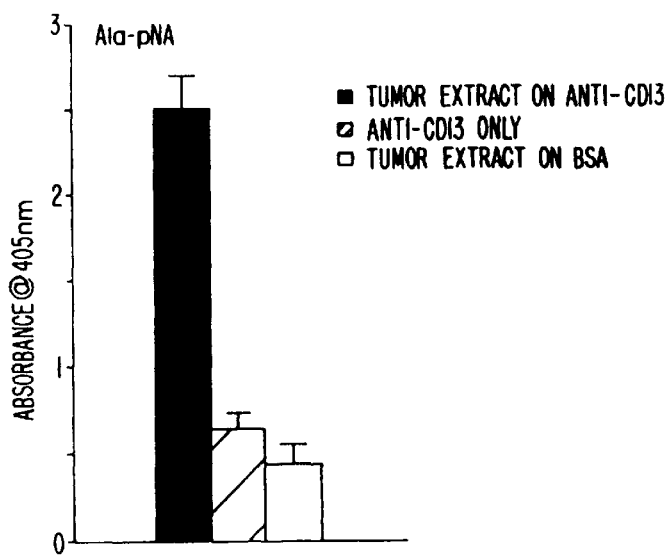
FIG. 4 shows isolation of CD13/aminopeptidase N (APN) and CNGRC-phage binding to CD13/APN. (A) Aminopeptidase enzymatic activity in immuno-isolated CD13 detected by using the CD13 substrates Ala-pNA or Leu-pNA. (B) Phage binding to immuno-isolated CD13 from a Kaposi's sarcoma tumor cell octylglucoside extract. Phage carrying the indicated peptides were tested for binding to CD13 that was immobilized using an anti-CD13 antibody WM15 coated on microtiter wells. (C) Inhibition of NGR-phage binding to CD13 by an NGR-containing cyclic peptide (CNGRC; SEQ ID NO:8) but not by an RGD-containing cyclic peptide or by an unrelated peptide.

FIG. 4A shows that aminopeptidase activity from the Kaposi's sarcoma cell extracts binds specifically to microtiter wells coated with the CD13 antibody, but not to wells coated with BSA. The CD13 antibody alone had no aminopeptidase activity. Moreover, the aminopeptidase N inhibitor, o-phenanthroline, inhibited the activity from the tumor extracts captured by the antibody.

Figure 4B:
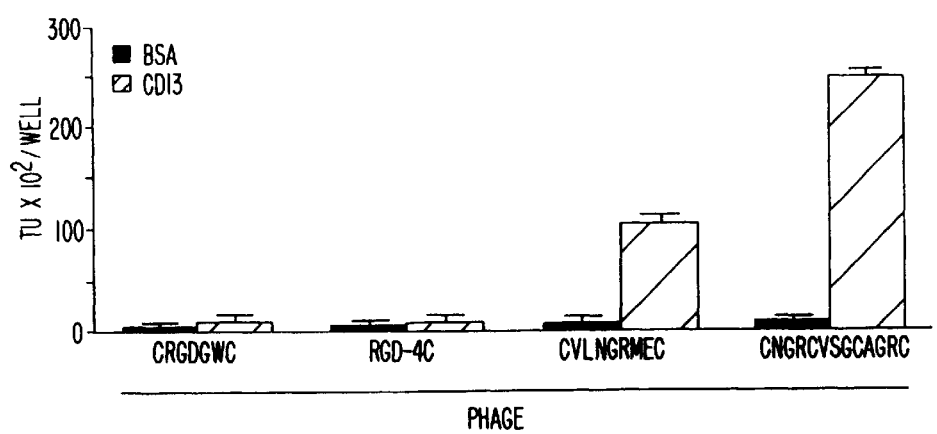

In FIG. 4B, NGR-containing phage were assayed for the ability to bind CD13. CD13 from Kaposi's sarcoma tumor cell octylglucoside extract was bound to microtiter wells precoated with the anti-CD13 antibody WM15 (Pharmingen; San Diego Calif.) (Favaloro et al., *Br. J. Heamatol.* 69:163–171 (1988), which is incorporated herein by reference). Various phage were added to the wells at $2 \times 10^9$ transducing units (TU) per well. The bound phage were quantitated by infection of bacteria as described (Koivunen et al., supra (1993); Pasqualini et al., supra, 1995). The data were expressed as means and standard errors from triplicate wells. As shown in FIG. 4B, three different phage, each of which displays the NGR motif in a different context, showed strong and selective binding to the immobilized CD13. Two RGD phage showed no significant binding (FIG. 4B), and various unrelated control phage also did not bind. These results indicate that CD13 recognizes the NGR motif better than RGD.

To confirm the specificity of NGR binding by CD13, the ability of NGR soluble peptides to inhibit the interaction was studied. Either CNGRC (SEQ ID NO:8), CRGDWC (SEQ ID NO:220), or GACVFSIAHECGA (SEQ ID NO:19) (unrelated control) peptides were added at 200 μg/well to the phage binding assay, and the bound phage quantitated by infection of bacteria. The data shown were expressed as means and standard errors from triplicate wells.

Figure 4C:
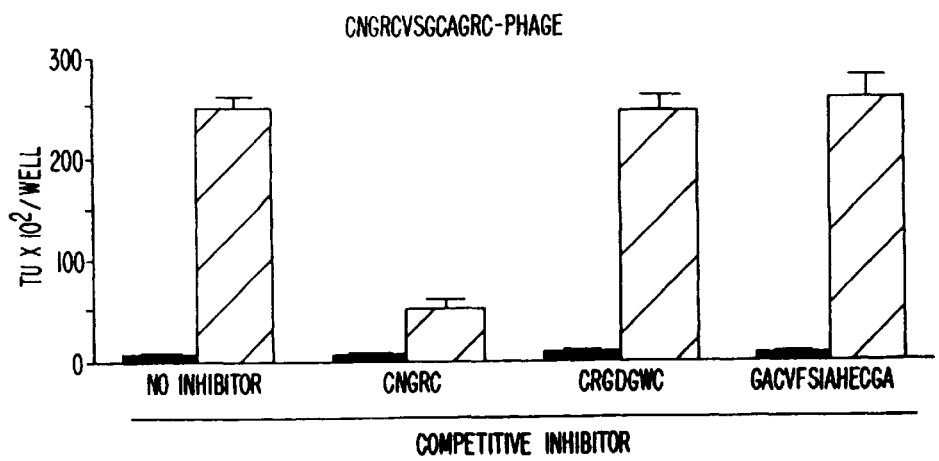

As shown in FIG. 4C, the NGR cyclic peptide, but not the RGD or the unrelated peptide, blocked the NGR phage binding. These results demonstrate that phage expressing the peptide sequence NGR and NGR peptides bind specifically to a CD13 related molecule.

Phage Binding Assays With CD13/APN-Transfected Cells

Figure 5:
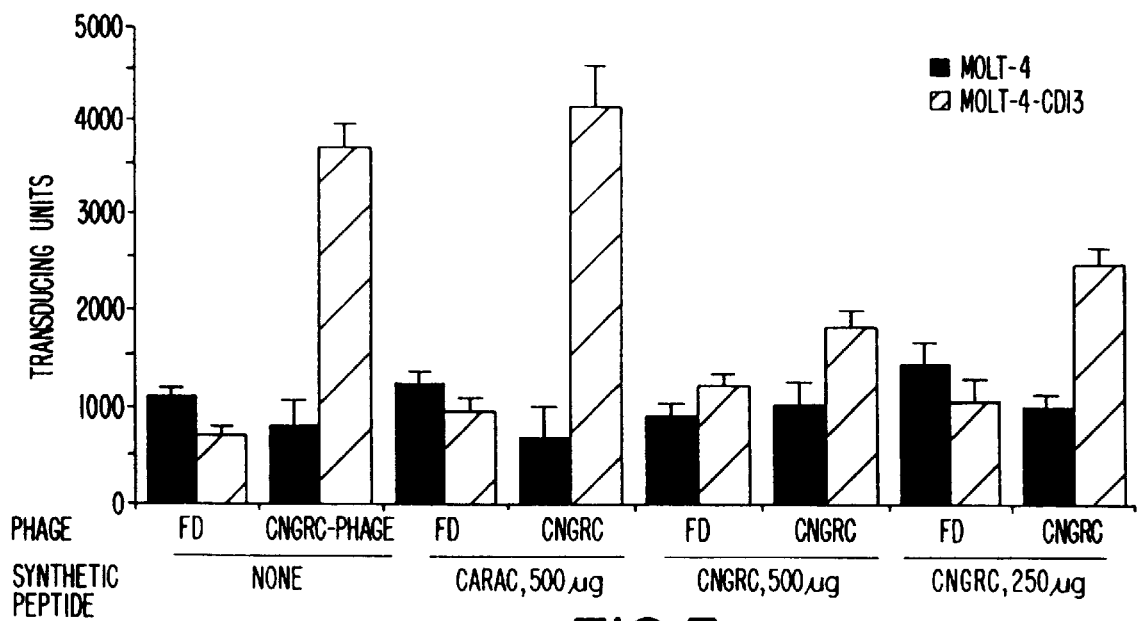
FIG. 5 shows binding of phage expressing an NGR containing peptide to cells transfected with CD13. CNGRC-phage binding to control Molt-4 cells and to Molt-4 cells transfected with CD13 and inhibition of the binding by the CNGRC cyclic peptide.

The CNGRC phage binds specifically to cells transfected with CD13. Two cell lines that do not express endogenous CD13, the Molt-4 human T cell leukemia and MDA-MB-435 breast carcinoma cell lines, were used to assay CNGRC (SEQ ID NO:8) phage binding to cells transfected with CD13. Briefly, mock transfected Molt-4 cells ("Molt-4/mock") and cells transfected with CD13 ("Molt-4/CD13") were incubated with CNGRC (SEQ ID NO:8) phage or with control Fd phage lacking an insert ($2 \times 10^9$ transducing units (TU) per sample). Synthetic peptides, CNGRC (SEQ ID NO:8) or the negative control CARAC (SEQ ID NO:221), were pre-incubated with the cells at 250 and 500 μg/ml. After extensive washing, bound phage were quantitated by infection of bacteria as described above. As shown in FIG. 5, CNGRC phage were found to bind to Molt-4/CD13 and to MDA-MB-435/CD13 transfected cells, but not to parental cell lines transfected with an empty control vector. Furthermore, the binding was blocked by the CNGRC (SEQ ID NO:8) peptide, but not by control peptides, demonstrating that the CNGRC (SEQ ID NO::8) binding was specific (FIG. 5). These results indicate that CD13 gene transfer confers to cells the ability to bind NGR phage.

EXAMPLE X

Affinity Purification of an NGR Receptor and Screening for High Affinity Ligands This example describes affinity purification of an NGR receptor and screening for high affinity ligands of an NGR receptor.

Affinity Chromatography of Extracts From CD13/APN Positive Cells on Immobilized CNGRC Peptide Yields CD13/APN To further characterize the interaction of CD13/APN with the NGR peptide, affinity chromatography on the CNGRC peptide was performed. The column was prepared by coupling the CNGRC peptide to SEPHAROSE (Pharmacia; Piscataway N.J.). Elution was effected with soluble CNGRC peptide. Experiments were performed using HL-60 cell extracts because they are known to express CD13/APN without other proteases that could interfere in the APN assay (Xu et al., supra (1997)). Thus, in HL-60 cell extracts, all detectable cell surface enzymatic activity is inhibitable by anti-CD13 blocking antibodies, assuring specificity. Extracts of Molt-4 and MDA-MB-435 cells transfected with CD13/APN were also characterized by using affinity chromatography, with extracts of the mock transfected counterparts used as negative controls.

Figure 6:
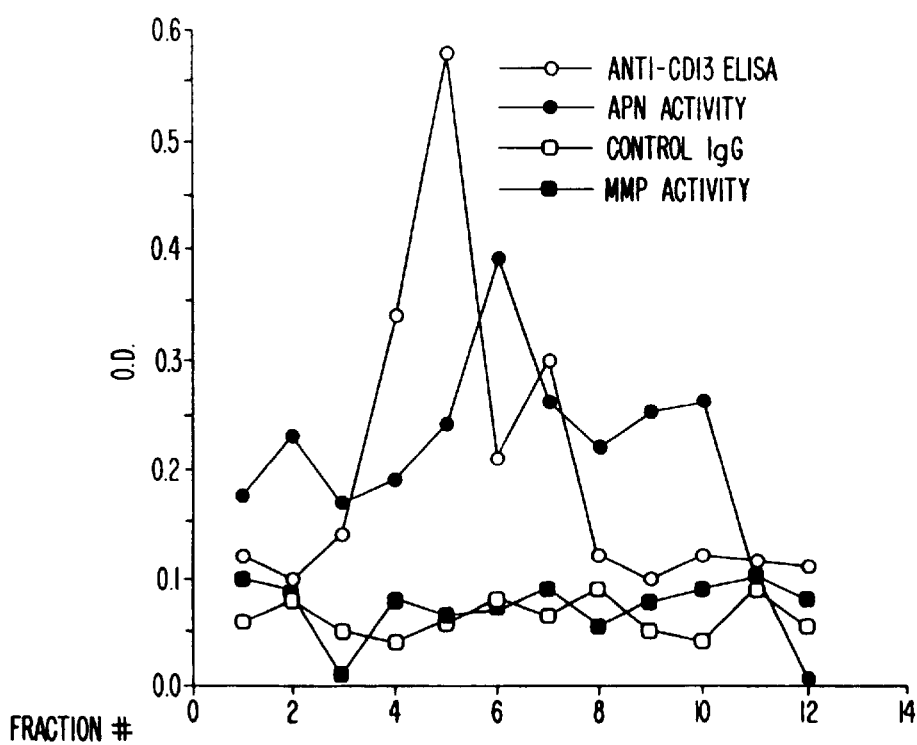
FIG. 6 shows affinity purification of CD13 from HL-60 cell extracts using an NGR peptide column and elution with CNGRC peptide. CD13 was detected in the fractions by using the WM15 monoclonal antibody, and normal mouse IgG was used as a negative control. Samples of each fraction were analyzed for aminopeptidase enzymatic activity by using Ala-PNA, and for matrix metalloprotease (MMP) activity by using an MMP substrate.

Briefly, CD13 was detected by testing aliquots of each fraction for the presence of CD13 immunoreactivity in ELISA with the anti-CD13 monoclonal antibody WM15, using normal mouse IgG as a negative control. The fractions were also analyzed for CD13 enzymatic activity using AlapNA as the substrate. In all cases, using Molt-4/CD13, MDA-MB-435/CD13 or HL-60 cell extracts, elution of the CNGRC-column with the CNGRC peptide yielded fractions containing functional CD13/APN (FIG. 6). No CD13 immunoreactivity was observed in the control samples using IgG, and no enzymatic activity was found employing a MMP-specific substrate. Moreover, affinity chromatography on a control peptide (CARAC; SEQ ID NO:221) yielded no CD13/APN, and the CARAC peptide did not elute any activity from the CNGRC column. Furthermore, no CD13 activity was recovered from the CNGRC column when the extract fractionated was derived from CD13-negative cells (see FIG. 6).

Isolation of Endothelial NGR Receptors by Affinity Chromatography

Protocols based on those developed for the isolation of certain integrins are used to isolate an NGR receptor using affinity chromatography. Tumor extracts and cultured endothelial cells treated with TNFα, a known angiogenic stimulator, prepared by extraction with octylglucoside are used as the source of the recepotor. The presence of the receptor is confirmed using a phage binding assay and inmunoblot analysis as described above. The specific phage show more binding to the activated endothelial cells than control phage. Cell binding assays with phage are performed as described previously (Barry et al., supra (1996), which is incorporated herein by reference).

The extract is run over a column of the peptide, coupled to SEPHAROSE, and bound material is eluted with the soluble peptide at 1 mg/ml. High affinity peptides isolated during the screening of secondary NGR libraries, described above, are used. Cells that do not bind the NCR-containing phage are used to make a control extract, and control elution from the peptide column is carried out with an unrelated cyclic peptide. The eluates are probed with anti-CD13 and the anti-NCR receptor phage antibodies. If desired, anti-NGR receptor antibodies are used for affinity chromatography alternatively or consecutively with the peptide affinity chromatography. The NGR receptor preparations obtained by NGR peptide affinity isolation contain an NGR reactive fragment and are reactive with CD13 antibodies.

Screening of Secondary NGR Libraries to Identify High Affinity Ligands for the NGR Receptor In order to identify additional high affinity ligands for the NCR receptor, secondary NCR libraries are constructed. Three such libraries, $X_2CNGRCX_2$ (SEQ ID NO:222), $CX_2(C/X)NGR$ $(C/X)X_2C$ (SEQ ID NO:223), and C NGRCX$_6$ (SEQ ID NO:224) (where "C" is cysteine and "X" is any amino acid), were prepared. In these secondary libraries, the NCR sequence is represented in different contexts which allows for multiple folding arrangements. Because higher affinities can be achieved with cyclic peptides, the libraries feature the NGR tripeptide in different cyclic configurations. The secondary libraries are screened against the target receptor in order to select the best-fit sequence/conformation for the ligand. This has been empirically demonstrated in a number of systems (Sparks et al., *Methods Enzymol.* 255:498–509 (1995); Martens et al., *J. Biol. Chem.* 270:21129–21136 (1995); Wrighton et al., *Science* 273:458–464 (1996), each of which is incorporated herein be reference).

The secondary NGR phage peptide libraries are constructed as follows. Phage display libraries are made as described in Smith and Scott, *Science* 228:1315–1317 (1985); Smith and Scott, *Methods Enzymol.* 21:228–257 (1993); and Koivunen et al., *Methods Enzymol.* 245:346–349 (1994), each of which is incorporated by reference). Briefly, FUSE 5 plasmid is isolated from transfected MC1061 cells using Qiagen Maxi-prep 500 columns (Qiagen; Chatsworth Calif.). The plasmid is cleaved to remove the 14 bp "stuffer" using SfiI restriction enzyme (New England Biolabs; Beverly Mass.) and purified with QIAquick PCR purification columns (Qiagen). The oligonucleotides encoding the peptides which are to be displayed by the phage are purchased commercially and converted into double stranded DNA utilizing a library primer (5'-TTCTGCCCCAGCGGCCCC-3'; SEQ ID NO:225). Two μg of the oligonucleotide and 4 μg of the primer are annealed in a volume of 10 μl at 65° C. for 2 min and cooled to room temperature. Primer extension is performed with SEQUENASE 2.0 DNA polymerase (United States Biochemical) for 60 min at 37° C. in a reaction volume of 50 μl containing 10 mM, and 5 mM dithiothreitol, and the double stranded oligonucleotides are purified using the QIAquick nucleotide removal kit (Qiagen). The oligonucleotide is subsequently digested with BglI (Boehringer Mannheim; Indianapolis Ind.) overnight at 37° C., purified as described above, and ligated to the FUSE 5 vector with T4 DNA Ligase (Gibco-BRL; Gaithersburg Md.). The plasmid is then transfected into MC1061 bacteria utilizing the Cell-Porator apparatus (Gibco-BRL). Approximately 25 μl of bacteria and ~100 mg of plasmid are shocked with 2.5 kV and immediately transferred to S.O.C. medium. A total of 100–200 electroporations are performed in order to achieve ~$10^9$ clones. For preparation of a $CX_2C\underline{NGR}CX_2$ (SEQ ID NO:222) secondary library, the primer 5'-CACTCGGCCGACGGGGCTTGTNN4 NN4TGT AATGGTAGGTGTNN4NN4GGGGCCGCTGGGGCAGA-A-3' (SEQ ID NO:202) is used, where N is any nucleotide and 4 is T or C). For preparation of a $CX_2(C/X)$ NGR(C/X)$X_2$C (SEQ ID NO:223) secondary library, the primer 5'-CACTCGGCCGACGGGGCTTGTNN4NN4NN4 AATGGGAGGNN4NN4NN4GGGGCCGCTGGGGCAGA-A-3' (SEQ ID NO:203) is used. For preparation of a C NGRCX$_6$ (SEQ ID NO: 224) secondary library, primer 5'-CACTCGGCCGACGGGGCTTGTAATGGGAGA TGTNN4NN4NN4NN4NN4NN4GGGGCCGCTGGGGC-A GAA-3' (SEQ ID NO:204) is used. The secondary NGR phage libraries are screened for the ability to bind immobilized CD13 or against CD13 transfected cells as described above, and binding ligands are identified. The secondary NGR libraries can also be screened for homing to tumor or other angiogenic vasculature.

Screening of Combinatorial scFv Libraries From Rabbits Immunized With Human Tumor Xenografts In order to identify additional high affinity ligands for the NGR receptor, combinatorial scFv libraries are prepared from rabbits immunized with human tumor xenografts. The tumor xenografts are established as described in Pasqualini et al., supra, 1997, and Arap, supra, 1998. The tumors are homogenized in PBS for immunization and injected subcutaneously into rabbits every two weeks. At least four injections are given; the immune response of the rabbits is evaluated by immunostaining of tumor tissue sections after the second and third immunization. Antibodies from sera of immunized rabbits are tested for binding to immobilized CD13, and to human integrins $α_Vβ_3$ and $α_Vβ_5$ as positive controls. Spleen and bone marrow from the immunized rabbits are harvested, and tissues from identically treated rabbits are pooled and used for total RNA preparation with TRI reagent (Molecular Research Center; Cincinnati Ohio). Reverse transcription of total RNA is performed with the 1st Strand cDNA Synthesis Kit for RT PCR (AMV; Boehringer Mannheim). Using the PCR primers listed below, $V_k$ (nine primer combinations), $V_l$ (one primer combination), and $V_q$ (four primer combinations) encoding sequences are amplified from the first strand cDNA. In pilot studies, all combinations gave rise to PCR products in the range of 350 bp. Using the overlap extension PCR primers listed below, scfv encoding sequences are assembled by fusing $V_k$ and $V_l$, respectively, with $V_g$ following SfiI cloning of the scFv encoding sequences into the phagemid vector pComb3H. Selection of the resulting scFv libraries against immobilized CD13 is performed.

The following primers are used for $V_k$ amplification (F=forward primer, B=backward primer; sequences in 5' to 3' direction; M=A/C, R=A/G, W=A/T, S=C/G, Y=C/T, K=G/T, V=A/C/G, H=A/C/T, D=A/G/T, B=C/G/T, N=A/C/G/T):

R S C V K 1 - F
  (GGGCCCAGGCGGCCGAGCTCGTGMTGACCCAG-ACTCCA; SEQ ID NO:205);
R S C V K 2 - F
  (GGGCCCAGGCGGCCGAGCTCGATMTGACCCAG-ACTCCA; SEQ ID NO:206);
R S C V K 3 - F
  (GGGCCCAGGCGGCCGAGCTCGTGATGACCCAG-ACTGAA; SEQ ID NO:207);
R K B 9 J 0 - B
  (GGAAGATCTAGAGGAACCACCTTTGATTTCCAC-ATTGGTGCC; SEQ ID NO:208);
R K B 9 J 1 0 - B
  (GGAAGATCTAGAGGAACCACCTTTGATTTCCAC-ATTGGTGCC; SEQ ID NO:209); and
R K B 4 2 J 0 - B
  (GGAAGATCTAGAGGAACCACCTTGACSACCAC-CTCGGTCCC; SEQ ID NO:210).

The following primers are used for $V_l$ amplification: RSCλ1 (GGGCCCAGGCGGCCGAGCTC GTGCTGACT-CAGTCGCCCTC; SEQ ID NO:211) and RJλ0-B (GGAAGATCTAGAGGAACCACCGCCTGTGACGGTC-AGCTGGGTCCC; SEQ ID NO:212).

The following primers are used for $V_g$ amplification:
R S C V H 0 1
  (GGTGGTTCCTCTAGATCTTCCCAGTCGGTGGAG-GAGTCCRGG; SEQ ID NO:213);
R S C V H 0 2
  (GGTGGTTCCTCTAGATCTTCCCAGTCGGTGAAG-GAGTCCGAG; SEQ ID NO:214);
R S C V H 0 3
  (GGTGGTTCCTCTAGATCTTCCCAGTCGYTGGAG-GAGTCCGGG; SEQ ID NO:215);
R S C V H 0 4
  (GGTGGTTCCTCTAGATCTTCCCAGSAGCAGCTG-RTGGAGTCCGG; SEQ ID NO:216); and
R S C G - B
  (CCTGGCCGGCCTGGCCACTAGTGACTGAYGGA-GCCTTAGGTTGCCC; SEQ ID NO:217).

The followings primers are used to prepare the scFv fusion:
R S C - F
  (GAGGAGGAGGAGGAGGAGGCGGGGCCCAGGC-GGCCGAGCTC; SEQ ID NO:218) and
R S C - B
  (GAGGAGGAGGAGGAGGAGCCTGGCCGGCCTG-GCCACTAGTG; SEQ ID NO:219).

EXAMPLE XI

Selective Cytotoxicity of Doxorubicin-CNGRC Conjugate Administered to CD13/APN-Positive Cells An in vitro bioassay was developed to measure receptor binding of CNGRC-doxorubicin (CNGRC-dox) (CNGRC; SEQ ID NO:8) conjugates to cells. Endothelial cells activated with TNFα were used. Alternatively, the test cells were transfected with CD13/APN. This assay is based on the fact that, after a brief incubation period, drug that has not bound to the cells can be removed by washing. There is a quantifiable difference in the cytotoxic effect of the doxorubicin conjugate compared to doxorubicin alone or doxorubicin coupled to a control peptide after washing, because the drug remains bound to the cells if the receptor for the conjugated peptide is present.

Figure 7:
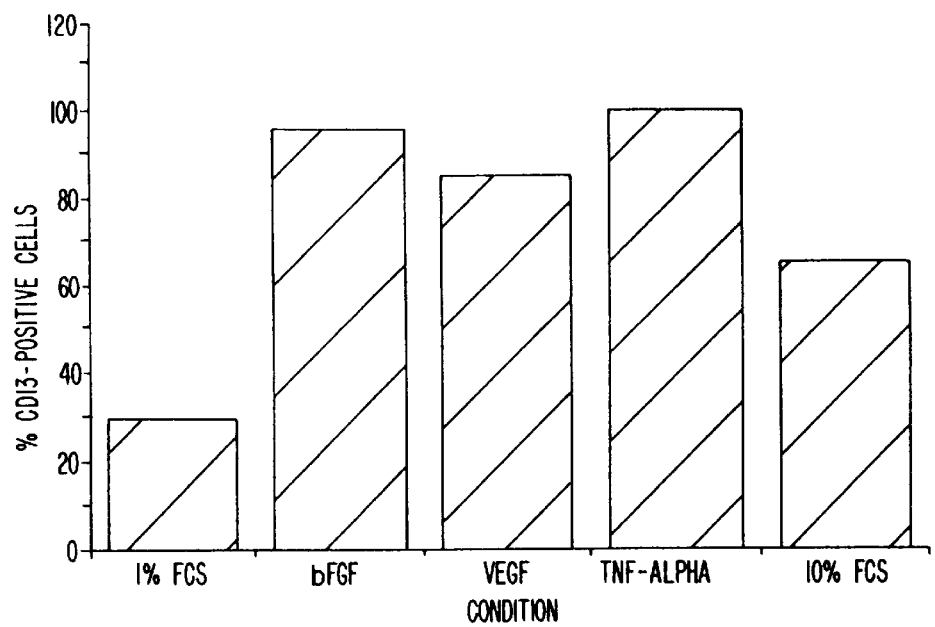
FIG. 7 shows upregulation of CD13 in cultured cells by angiogenic factors. Upregulation of CD13 by angiogenic factors in human umbilical cord endothelial cells (HUVEC).

This system was used with activated endothelial cells because CD13 expression has been shown to be upregulated when endothelial cells such as human umbilical vein endothelial cells (HUVEC) are stimulated (see FIG. 7). It was observed that CD13 was induced upon stimulation of endothelial cells with growth factors such as bFGF, VEGF and TNFα, known endothelial cell activator cytokines.

Briefly, to study the upregulation of CD13 by angiogenic factors, endothelial cells were cultured in different conditions, as indicated in FIG. 7, and the cell surface was stained for CD13 with the anti-CD13 monoclonal antibody, WM15. The percentage of CD13 expression was calculated based on the levels detected in cells growing in normal tissue culture medium with 10% FCS.

Figure 8A:
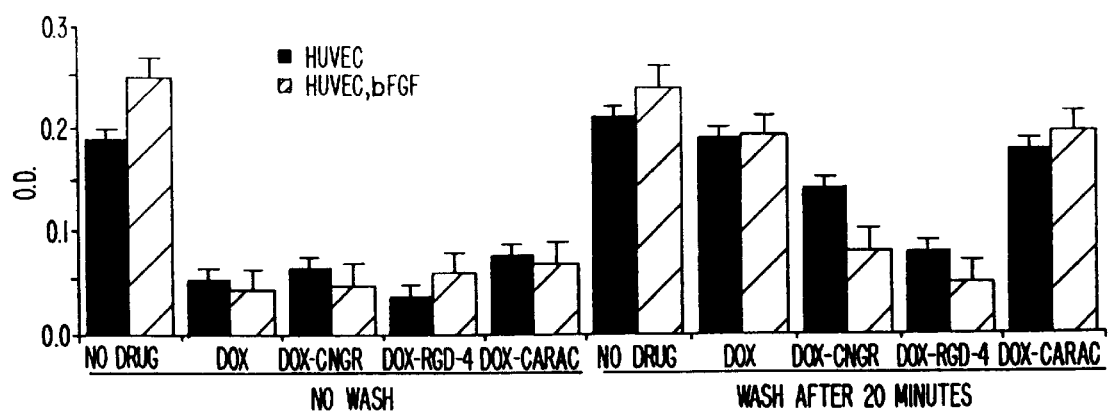
FIG. 8 shows CD13-dependent cytotoxic activity of doxorubicin/CNGRC (CNGRC-dox) in vitro. (A) CD13-dependent cytotoxic activity of CNGRC-doxorubicin in vitro in activated HUVECs. (B) CD13-dependent activity of CNGRC-doxorubicin in vitro in CD13 transfected MDA-MB-435 breast carcinoma cells.
Figure 8B:
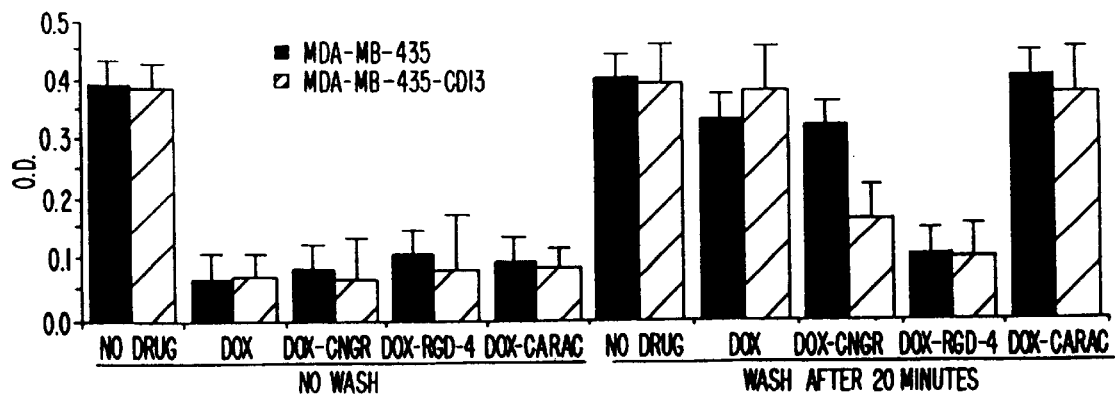

In vitro cytotoxicity of doxorubicin and targeted doxorubicin was evaluated using activated HUVECs (FIG. 8A) or CD-13 transfected 435-breast carcinoma cells (FIG. 8B). These cell lines are sensitive to doxorubicin. Cell monolayers were incubated with doxorubicin or a doxorubicin-peptide conjugate of RGD-4C (CDCRGDCFC; SEQ ID NO:1), CNGRC (SEQ ID NO:8), or CARAC (SEQ ID NO:221) at a concentration of 1 μg/well for 20 minutes in two sets of triplicates. One set of triplicates was washed three times with DMEM to remove unbound drug 20 min after drug addition (right). Untreated monolayers were used as controls. After 24 hours, attached cells were fixed and quantified by Crystal Violet.

The CNGRC-doxorubicin conjugate was more effective on the CD13-expressing cells than the control cells (see FIG. 8). These results demonstrate that CNGRC-doxorubicin has CD13-dependent cytotoxic activity in vitro and that the CNGRC (SEQ ID NO:8) peptide can guide a toxic moiety such as doxorubicin to CD13-positive cells.

EXAMPLE XII

CD13 Expression in Mouse and Human Angiogenic Vasculature

These experiments demonstrate that CD13 is expressed in angiogenic vasculature but is not detected in normal vasculature.

As described above, NGR-containing phage injected intravenously home to tumor vasculature, but not to normal vessels in other tissues. To determine binding of CNGRC (SEQ ID NO:8) phage to tissues using a different technique and to analyze human tissue, immunohistochemical staining of CNGRC (SEQ ID NO:8) phage and Fd control phage in tissue sections was performed. Phage displaying the peptide CNGRC (SEQ ID NO:8) or control phage with no insert were incubated with human breast carcinoma and normal breast tissue. An antibody against M-13 phage (Pharmacia) was used for the staining. The results indicated that the CNGRC-phage binds to human tumor vessels in tissue sections, but not to normal vessels. A phage with no insert (fd phage), used as a negative control, did not bind to normal or to tumor tissue sections.

As shown in Table 4, CD13 was expressed in a number of tumor cells and HUVECs. However, CD13 was not detected in the vasculature of normal organs (Table 5). Thus, based on the analysis of CD13 expression in the vasculature in murine and human tissues, CD13 is expressed in angiogenic vessels, but cannot be detected in normal vessels.

TABLE 4

Expression of CD13/APN on cell lines

| anti-CD13 monoclonals | WM15 | 1H4 |
|---|---|---|
| MDA-MB-435 (Breast carcinoma) | – | – |
| KS1767 (Kaposi's sarcoma) | ++++ | ++++ |
| C8161 (melanoma) | ++++ | ++++ |
| SKOV3-ip (ovarian carcinoma) | + | + |
| HUVECs (endothelial cells) | –/++/++++ | –/+++ |
| HDM-ZW (Hodgkin's lymphoma) | +++++ | +++++ |
| Molt-4 (T cell leukemia) | – | – |
| HL-60 (acute myeloid leukemia) | +++ | +++ |

Immunostainings were performed using two monoclonal antibodies against CD13, WM15 and 1H4.

TABLE 5

Expression of CD13/APN in normal and tumor vasculature

| Anti-CD13 monoclonals | WM15 | 1H4 ab |
|---|---|---|
| blood vessels in normal organs | | |
| brain | – | –/+ |
| kidney | – | – |
| skin | – | – |
| liver | – | – |
| lung | – | – |
| spleen | – | – |
| intestine | – | – |
| heart | – | – |
| retina | – | – |
| spinal cord | +/– | +/– |
| tumor vasculature* | | |
| endothelial cells | ++++ | ++++ |
| pericytes | ++++ | +++ |

*Human tumors tested: breast, colon, gastric, and esophageal carcinomas. Analysis of normal mouse tissues and tumors (MDA-MB-435 and Kaposi's sarcoma) with anti-mouse anti-CD13 antibodies (R3-63 and 2M7) showed similar results.

Confocal microscopy was performed to study the cellular localization of CD13 in tumor vasculature. Confocal microscopy was used to detect immunofluorescent staining of CD13 in tumor vessels. The images were obtained by superimposing the immunofluorescent and differential interference contrast (DIC) images, to reveal tissue morphology, or by direct immunofluorescence. Human breast carcinoma tissue sections were incubated with an anti-CD13 antibody (WM15) or control IgG. A FITC-conjugated secondary antibody against mouse IgG was used to reveal anti-CD13 localization. The negative control omitted the primary antibodies. Human breast carcinoma serial sections, gastric adenocarcinoma and colon carcinoma tissue sections were stained with anti-CD13 antibody. An antibody against APA, a known pericyte marker, was used for localization purposes.

Autofluorescence of fixed red blood cells (RBC) was visible. In tissue sections incubated with the anti-CD13 monoclonal antibody, only endothelial cells on small tumor vessels showed specific immunoreactivity. CD13 expression was confined to the endothelial cells and pericytes in multiple tumor types including breast, colorectal, and gastric carcinoma. Similar staining patterns were obtained with the NGR phage. In each case, reactivity could be detected in the vasculature of the tumors, but not in the vasculature of normal tissues (see Table 5). As expected, APA was not detected in endothelial cells but was present in pericytes located in tumor blood vessels. These results demonstrate that CD13 is expressed in angiogenic vasculature but is not detected in normal vasculature.

EXAMPLE XIII

NGR Phage Home Preferentially to Tumor Vasculature Over Retinal Neovasculature These results demonstrate that NGR phage preferentially home to tumor vasculature compared to retinal vasculature.

One experimental model of angiogenesis, oxygen-induced angiogenesis, was used to evaluate the role of CD13 in angiogenesis (Pierce et al., *Proc. Natl. Acad. Sci. USA* 92:905–909 (1995); Smith et al., *Invest. Ophthalmol. Vis. Sci.* 35:101–111 (1994), each of which is incorporated herein by reference). NGR phage bound to angiogenic retinal neovasculature induced by oxygen, giving results similar to those obtained with RGD-4C (CDCRGDCFC; SEQ ID NO:1) phage. CNGRC, RGD-4C (CDCRGDCFC; SEQ ID NO:1), and control fd phage lacking an insert were recovered from breast carcinoma xenografts, normal retina or angiogenic retina. Briefly, $10^6$ transducing units (TU) of phage were injected into the tail vein of mice bearing size-matched MDA-MB-435 derived tumors (~1000 mm$^3$) or p17 mice that had been exposed to oxygen (Pierce et al., supra, 1995; Smith et al., supra, 1994). The same number of transducing units of an ampicillin control phage was co-injected in order to assess specificity of the different tetracycline phage. In each case, phage were recovered after perfusion. The ratios were calculated using the mean number of phage recovered from the tissues after triplicate plating on ampicillin selective and tetracycline selective plates.

Figure 9A:
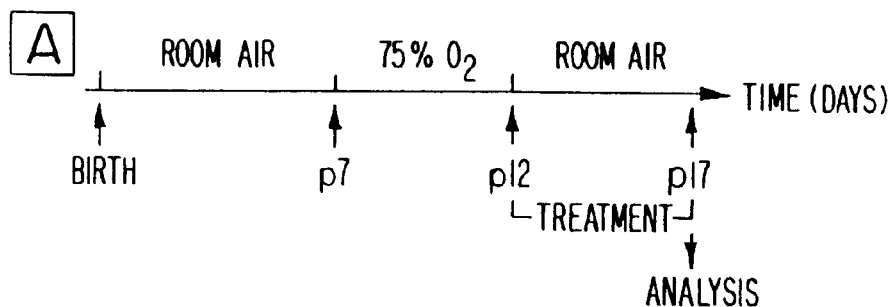
FIG. 9 shows recovery of CNGRC phage, RGD-4C phage, and control phage (insertless fd) from breast carcinoma xenografts, normal retina and angiogenic retina. (A) The experimental design is shown. (B) The ratio of recovered tetracycline-resistant to ampicillin-resistant phage is shown.

Mice that were not exposed to oxygen did not develop retinal angiogenic vessels (control) and were also injected to evaluate phage homing to normal retina. One-week-old C57BL/6J mice were exposed to a 75% oxygen atmosphere for five days, and then kept in room air for another five days (FIG. 9A). The proliferative neovascular response was quantified by counting the nuclei of new vessels extending from the retina into the vitreous in 6 µm cross-sections. This model was used to assess the binding of phage injected intravenously to the newly formed angiogenic vessels. To test phage homing in this system, phage displaying the RGD-4C (CDCRGDCFC; SEQ ID NO:1) peptide (which binds selectively to $\alpha_V$ integrins) or CNGRC-phage were injected intravenously prior to immunohistochemical analysis. The $\alpha_V$ integrins have been shown to be upregulated in these vessels. Phage staining was seen with the RGD-4C (CDCRGDCFC; SEQ ID NO:1) and CNGRC phage in the neovascular formations, whereas the normal vessels were negative.

Figure 9B:
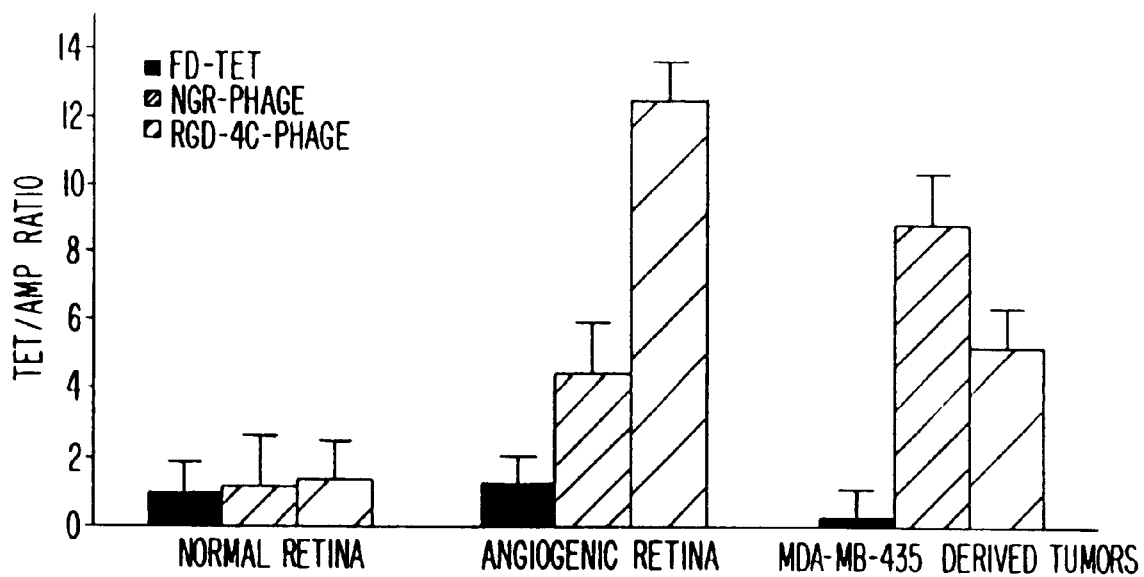

Side by side comparison of the RGD-4C (CDCRGDCFC; SEQ ID NO:1) and the CNGRC-phage homing in angiogenic vasculature of retina or tumors indicated that the two phage have opposite homing preferences: more RGD-4C (CDCRGDCFC; SEQ ID NO:1) phage were recovered from the retina than CNGRC-phage, whereas more CNGRC-phage were recovered from tumors (FIG. 9B). The homing of each phage also was inhibited by the appropriate cognate peptide, and this inhibition was not observed with control phage (FIG. 9B). These results indicate that expression of the NGR receptor can be higher during tumor angiogenesis than in other types of angiogenesis.

EXAMPLE XIV

Role of CD13 in Angiogenesis

These experiments demonstrate that CD13 is functionally important in angiogenesis.

Several experimental models involving cytokine-induced angiogenesis (Brooks et al., *Cell* 79:1157–1164 (1994) and tumor-induced angiogenesis (Folkman, supra (1995); Arap et al., supra (1998), each of which is incorporated herein by reference) were used to evaluate the role of CD13 in angiogenesis.

A functional role for CD13 in angiogenesis was demonstrated by using CD13 antagonists. Specifically, the CD13 inhibitor bestatin, as well as monoclonal antibodies that block CD13 enzymatic activity, were tested in several angiogenesis assays. These assays included cytokine-induced angiogenesis in the CAM, oxygen-induced retinal neovascularization, and tumor-induced angiogenesis.

Oxygen-induced angiogenesis in the retina was inhibited by treating the animals with antagonists of CD13. Briefly, inhibition of oxygen-induced retinal neovascularization was determined upon injection of CD13 antagonists. One-week-old C57BL/6J mice were exposed to a 75% oxygen atmosphere for five days, and then kept in room air for one week. In the control mice, which were treated with PBS or rat IgG, a proliferative neovascular response resulted and was quantified as described above. Anti-mouse CD13 inhibitory antibodies R3-63 and 2M7 (250 µg/mouse/day) or bestatin (200 µg/mouse/day) were injected intraperitoneally, and the inhibitory effect determined. Animals treated with the CD13 antagonist antibodies and bestatin showed only 20–30% of the angiogenic response observed in the mice treated with controls (IgG and vehicle).

The CD13 antagonists also suppressed bFGF-induced angiogenesis in the CAM. Briefly, angiogenesis was induced in CAMs from 10-day chicken embryos by bFGF filters implanted onto regions that were previously avascular. Various treatments were applied topically, and, after 3 days, the filters and surrounding CAMs were resected and fixed in formalin.

Figure 10A:
FIG. 10 shows the suppression of bFGF-induced angiogenesis in chicken chorioallantoic membrane and inhibition of tumor growth by CD13 antagonists. (A) CD13 antagonists, anti-CD13 antibody, bestatin and actinonin, suppress bFGF-induced angiogenesis. (B) Inhibition of the growth of 435 breast carcinoma tumors upon injection of a CD13 antagonist antibody.

FIG. 10A shows the number of blood vessels entering the disk within the focal plane of the CAM, counted under a stereomicroscope by two observers in a double-blind fashion. Each bar represents the mean number of vessels and standard errors from 8 CAMs on each group. There were significantly fewer vessels entering the disks treated with inhibitors of CD13 enzymatic activity (p<0.05). These results also demonstrate that the inhibitory antibody used in the anti-angiogenic treatments recognizes chicken CD13 and that CD13 is expressed in CAM angiogenic vasculature.

Figure 10B:
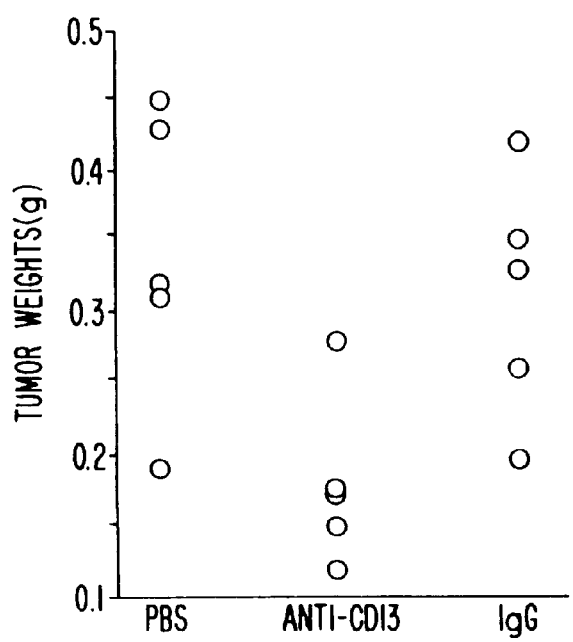

The effects of anti-mouse CD13 agonists were also studied in tumor-bearing mice. Mice bearing size-matched 435 breast carcinoma tumors were divided in three groups (five mice per group). Anti-mouse CD13 inhibitory antibodies R3-63 and 2M7 (500 µg/mouse/day) or bestatin (200 µg/mouse/day) were injected intraperitoneally. In the control groups, mice were treated with PBS or rat IgG. As shown in FIG. 10B, tumor growth was retarded in comparison with the tumor growth seen in mice that received control rat IgG or injections of vehicle only. Treatment with bestatin produced similar results to those observed with the anti-CD13 antibodies (p<0.05).

These results indicate that CD13 is a new marker of tumor vasculature that serves as a specific receptor for NGR ligands and plays a functional role in angiogenesis.

EXAMPLE XV

Tumor Therapy Using Doxorubicin/Tumor Homing NGR Peptide Conjugates

This example describes in vivo tumor therapy with NGR peptide conjugated to doxorubicin.

The drug conjugates made with RGD-4C (CDCRGDCFC; SEQ ID NO:1) and CNCRC were found to be more effective and less toxic than the free drug (Arap et al., supra (1998), which is incorporated herein by reference). Similar results were observed when mice bearing multiple tumor types were treated with the drug-conjugates. Specifically, mice bearing MDA-MB-435-derived breast carcinomas and Hodgkin's lymphoma were treated with doxorubicin-CNGRC peptide conjugate as follows.

Figure 11A:
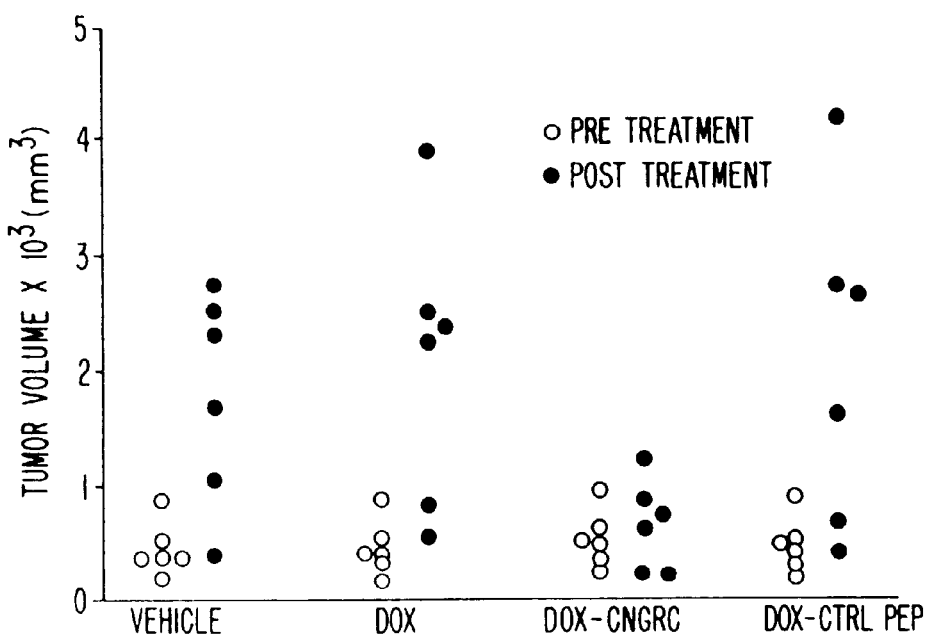
FIG. 11 shows treatment of mice bearing MDA-MB-435-derived breast carcinomas and Hodgkin's lymphoma with doxorubicin-CNGRC peptide conjugate. Mice with size-matched tumors (~1000 mm$^3$) were randomized into four treatment groups (six animals per group): vehicle only, free doxorubicin (dox), doxorubicin-control peptide (dox-ctrl pep), and doxorubicin-CNGRC (dox-CNGRC). (A) Mice were treated at 5 µg/mouse/week of doxorubicin-equivalent. Difference in tumor volumes between day 1 and day 28 are shown. (B) A Kaplan-Meier survival curve of the mice in Panel A is shown. (C) Mice bearing large (~5000 mm³) MDA-MB-435 breast carcinomas (four animals per group) were randomized to receive a single-dose of free doxorubicin or doxorubicin-CNGRC conjugate at 200 μg/mouse of doxorubicin equivalent. A Kaplan-Meier survival curve is shown. (D) Mice bearing large (~5000 mm³) Hodgkin's lymphoma (eight animals per group) were randomized to receive two doses of free doxorubicin plus unconjugated CNGRC peptide or doxorubicin-CNGRC conjugate at 40 μg/mouse of doxorubicin equivalent. A Kaplan-Meier survival curve is shown.
Figure 11B:
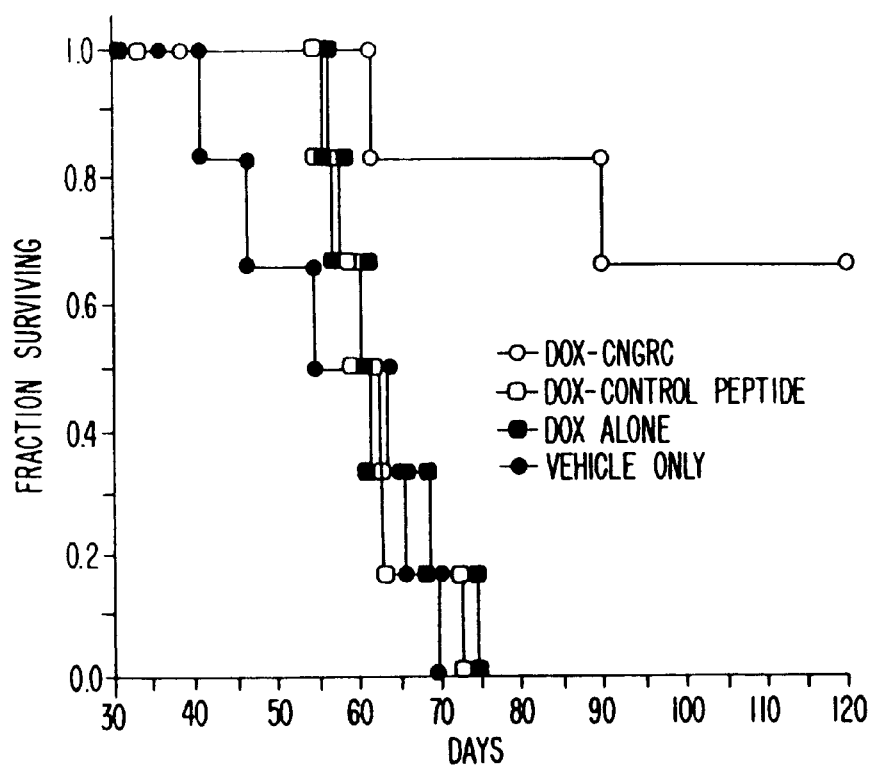

Briefly, mice with size-matched tumors (~1000 mm$^3$) were randomized into four treatment groups (six animals per group): vehicle only, free doxorubicin, doxorubicin-control peptide, and doxorubicin-CNGRC (SSEQ ID NO:8). Mice were treated at 5 µg/mouse/week of doxorubicin-equivalent, and the difference in tumor volumes between day 1 and day 28 determined (FIG. 11A). FIG. 11B shows a Kaplan-Meier survival curve of the mice in FIG. 11A.

Figure 11C:
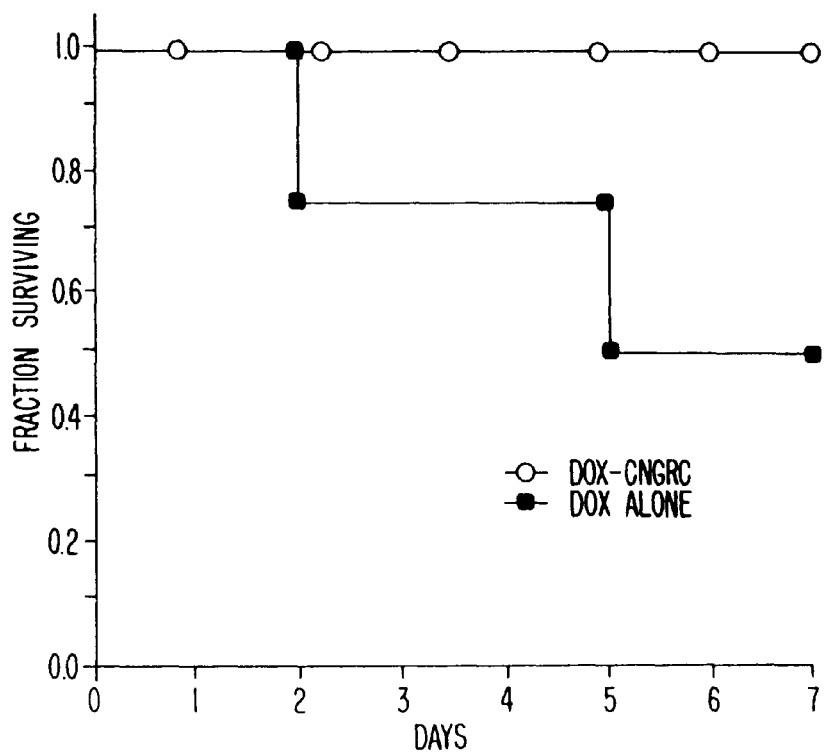

To test toxicity of the CNGRC conjugate, mice bearing large (~5000 mm$^3$) MDA-MB-435 breast carcinomas (four animals per group) were randomized to receive a single-dose of free doxorubicin or doxorubicin-CNGRC conjugate at 200 µg/mouse of doxorubicin equivalent. The data are shown as a Kaplan-Meier survival curve in FIG. 11C.

Mice bearing large (~5000 mm$^3$) Hodgkin's lymphoma (eight animals per group) were randomized to receive two doses of free doxorubicin plus unconjugated CNGRC peptide or doxorubicin-CNGRC (SEQ ID NO:8) conjugate at 40 µg/mouse of doxorubicin equivalent. The data are shown as a Kaplan-Meier survival curve in FIG. 11D.

Figure 11D:
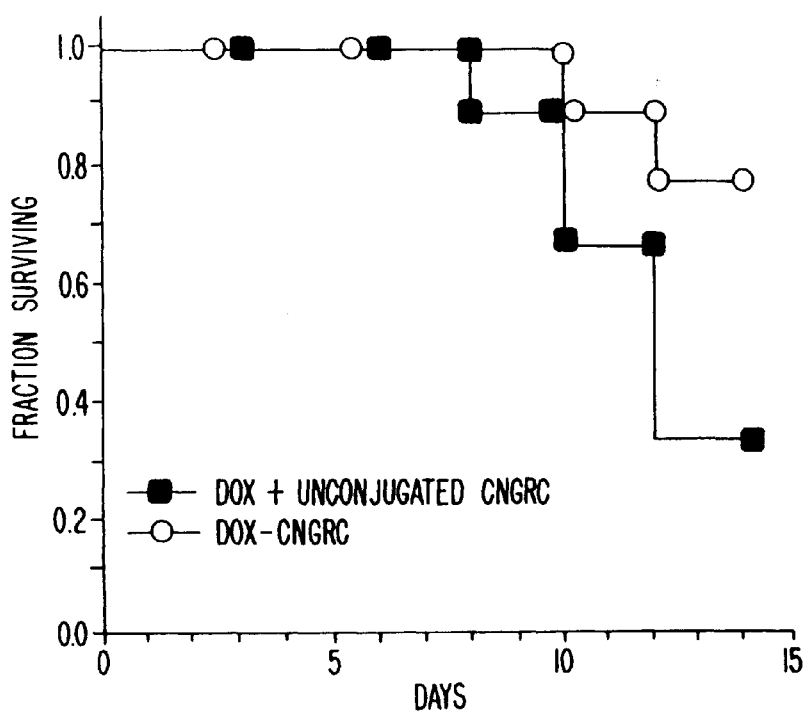

The experiments show the effect of doxorubicin-CNGRC conjugate on mice bearing breast carcinomas (FIG. 11A, 11B and 11C) (Arap et al., supra, 1998), and Hodgkin's lymphomas (FIG. 11D). Tumor-bearing mice treated with doxorubicin-CNGRC (SEQ ID NO:8) lived longer than those treated with the unconjugated peptide doxorubicin mixture or doxorubicin alone (FIG. 11B, 11C and 11D) (Arap et al., supra, 1998). Cures were also observed, which was not seen with the control treatments. Similar results were obtained when the doxorubicin-CNGRC (SEQ ID NO:8) conjugate was tested in melanoma and Kaposi's sarcoma xenografts. Furthermore, the targeting of the CNGRC-phage and the anti-tumor effect of the doxorubicin-CNGRC (SEQ ID NO:8) conjugate in vivo was equally efficient, whether or not the tumor cells expressed CD13/NGR receptor as in the case of Hodgkin's lymphoma, C8161 melanoma, and Kaposi's sarcoma or did not express CD13 as in MDA-MD-435 breast carcinoma.

These results demonstrate that it is possible to target a chemotherapeutic drug to angiogenic vasculature, a common feature in all solid tumors, using an NGR tumor homing peptide that homes to an NGR receptor.

Although the invention has been described with reference to the disclosed examples, it should be understood that various modifications can be made without departing from the spirit of the invention. Accordingly, the invention is limited only by the following claims.

We claim:

1. A method of identifying a tumor homing molecule that homes to angiogenic vasculature of a tumor, comprising:
   (a) contacting substantially purified CD13/aminopeptidase N NGR receptor with one or more molecules; and
   (b) determining specific binding of a molecule to said NGR receptor,
wherein the presence of specific binding identifies said molecule as a tumor homing molecule that homes to angiogenic vasculature of a tumor.

2. The method of claim 1, further comprising the steps of:
   (c) administering an NGR binding molecule in vivo; and
   (d) determining binding of said NGR binding molecule to angiogenic vasculature of a tumor.

3. The method of claim 1, wherein said substantially purified NGR receptor is immobilized to a support.

* * * * *

UNITED STATES PATENT AND TRADEMARK OFFICE
CERTIFICATE OF CORRECTION

PATENT NO. : 6,180,084 B1
DATED : January 30, 2001
INVENTOR(S) : Ruoslahti et al.

It is certified that error appears in the above-identified patent and that said Letters Patent is hereby corrected as shown below:

Column 16,
Line 43, please delete ""tumorr"" and replace with -- "tumor" --.

Column 41,
Line 33, please delete "dentifying" and replace with -- identifying --.

Column 50,
Line 10, please delete "immunostairing" and replace with -- immunostaining --.
Line 41, please delete "immunohistochemica" and replace with -- immunohistochemical --.

Column 55,
Line 5, please delete "metastascis" and replace with -- metastasis --.

Column 56,
Line 8, please delete "RCD-containing" and replace with -- RGD-containing --.

Column 58,
Line 17, please delete "octylgiucoside" and replace with -- octylglucoside --.
Line 18, please delete "recepotor" and replace with -- receptor --.
Lines 29, 42 and 47, please delete "NCR" and replace with -- NGR --.

Signed and Sealed this

Twenty-fifth Day of May, 2004

JON W. DUDAS
*Acting Director of the United States Patent and Trademark Office*

SEQUENCE LISTING

<160> NUMBER OF SEQ ID NOS: 226

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Cys Asp Cys Arg Gly Asp Cys Phe Cys
 1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Cys Gly Arg Glu Cys Pro Arg Leu Cys Gln Ser Ser Cys
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

```
Cys Asn Gly Arg Cys Val Ser Gly Cys Ala Gly Arg Cys
 1               5                  10
```

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

```
Cys Leu Ser Gly Ser Leu Ser Cys
 1               5
```

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

```
Cys Gly Ser Leu Val Arg Cys
 1               5
```

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

```
Asn Gly Arg Ala His Ala
 1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

```
Cys Val Leu Asn Gly Arg Met Glu Cys
 1               5
```

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

```
Cys Asn Gly Arg Cys
 1               5
```

<210> SEQ ID NO 9
<211> LENGTH: 7
<212> TYPE: PRT
<213> ORGANISM: Artificial Sequence

```
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(6)
<223> OTHER INFORMATION: any

<400> SEQUENCE: 9

Cys Xaa Xaa Xaa Xaa Xaa Cys
 1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(7)
<223> OTHER INFORMATION: any

<400> SEQUENCE: 10

Cys Xaa Xaa Xaa Xaa Xaa Xaa Cys
 1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(8)
<223> OTHER INFORMATION: any

<400> SEQUENCE: 11

Cys Xaa Xaa Xaa Xaa Xaa Xaa Xaa Cys
 1               5

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(4)
<223> OTHER INFORMATION: any
<220> FEATURE:
<221> NAME/KEY: UNSURE
<222> LOCATION: (6)..(8)
<223> OTHER INFORMATION: any
<220> FEATURE:
<221> NAME/KEY: UNSURE
<222> LOCATION: (10)..(12)
<223> OTHER INFORMATION: any

<400> SEQUENCE: 12

Cys Xaa Xaa Xaa Cys Xaa Xaa Xaa Cys Xaa Xaa Xaa Cys
 1               5                  10

<210> SEQ ID NO 13
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(4)
<223> OTHER INFORMATION: any
<220> FEATURE:
<221> NAME/KEY: UNSURE
<222> LOCATION: (8)..(9)
<223> OTHER INFORMATION: any

<400> SEQUENCE: 13

Cys Xaa Xaa Xaa Asn Gly Arg Xaa Xaa
 1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: UNSURE
<222> LOCATION: (2)..(3)
<223> OTHER INFORMATION: any
<220> FEATURE:
<221> NAME/KEY: UNSURE
<222> LOCATION: (9)
<223> OTHER INFORMATION: any

<400> SEQUENCE: 14

Cys Xaa Xaa Cys Asn Gly Arg Cys Xaa
 1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Cys Asn Lys Thr Asp Gly Asp Glu Gly Val Thr Cys
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

Ala Cys Asp Cys Arg Gly Asp Cys Phe Cys Gly
 1               5                  10

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 17
```

```
Gly Arg Gly Glu Ser Pro
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 18

Trp Gly Thr Gly Leu Cys
  1               5

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 19

Gly Ala Cys Val Phe Ser Ile Ala His Glu Cys Gly Ala
  1               5                  10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 20

Cys Gly Glu Ala Cys Gly Gly Gln Cys Ala Leu Pro Cys
  1               5                  10

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 21

Ile Trp Ser Gly Tyr Gly Val Tyr Trp
  1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Pro Ser Cys Ala Tyr Met Cys Ile Thr
  1               5

<210> SEQ ID NO 23
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      Peptide

<400> SEQUENCE: 23

Trp Glu Ser Leu Tyr Phe Pro Arg Glu
  1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Ser Lys Val Leu Tyr Tyr Asn Trp Glu
  1               5

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 25

Cys Gly Leu Met Cys Gln Gly Ala Cys Phe Asp Val Cys
  1               5                  10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 26

Cys Glu Arg Ala Cys Arg Asn Leu Cys Arg Glu Gly Cys
  1               5                  10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 27

Cys Pro Arg Gly Cys Leu Ala Val Cys Val Ser Gln Cys
  1               5                  10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 28

Cys Lys Val Cys Asn Gly Arg Cys Cys Gly
  1               5                  10
```

```
<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 29

Cys Glu Met Cys Asn Gly Arg Cys Met Gly
 1               5                  10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 30

Cys Pro Leu Cys Asn Gly Arg Cys Ala Leu
 1               5                  10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 31

Cys Pro Thr Cys Asn Gly Arg Cys Val Arg
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 32

Cys Gly Val Cys Asn Gly Arg Cys Gly Leu
 1               5                  10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 33

Cys Glu Gln Cys Asn Gly Arg Cys Gly Gln
 1               5                  10

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 34
```

```
Cys Arg Asn Cys Asn Gly Arg Cys Glu Gly
  1               5                  10
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 35

```
Cys Val Leu Cys Asn Gly Arg Cys Trp Ser
  1               5                  10
```

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 36

```
Cys Val Thr Cys Asn Gly Arg Cys Arg Val
  1               5                  10
```

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 37

```
Cys Thr Glu Cys Asn Gly Arg Cys Gln Leu
  1               5                  10
```

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 38

```
Cys Arg Thr Cys Asn Gly Arg Cys Leu Glu
  1               5                  10
```

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 39

```
Cys Glu Thr Cys Asn Gly Arg Cys Val Gly
  1               5                  10
```

<210> SEQ ID NO 40
<211> LENGTH: 10
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 40

Cys Ala Val Cys Asn Gly Arg Cys Gly Phe
  1               5                  10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 41

Cys Arg Asp Leu Asn Gly Arg Lys Val Met
  1               5                  10

<210> SEQ ID NO 42
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 42

Cys Ser Cys Cys Asn Gly Arg Cys Gly Asp
  1               5                  10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 43

Cys Trp Gly Cys Asn Gly Arg Cys Arg Met
  1               5                  10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 44

Cys Pro Leu Cys Asn Gly Arg Cys Ala Arg
  1               5                  10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 45

Cys Lys Ser Cys Asn Gly Arg Cys Leu Ala
  1               5                  10
```

```
<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 46

Cys Val Pro Cys Asn Gly Arg Cys His Glu
 1               5                  10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 47

Cys Gln Ser Cys Asn Gly Arg Cys Val Arg
 1               5                  10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 48

Cys Arg Thr Cys Asn Gly Arg Cys Gln Val
 1               5                  10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 49

Cys Val Gln Cys Asn Gly Arg Cys Ala Leu
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 50

Cys Arg Cys Cys Asn Gly Arg Cys Ser Pro
 1               5                  10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
```

-continued

```
<400> SEQUENCE: 51

Cys Ala Ser Asn Asn Gly Arg Val Val Leu
  1               5                  10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 52

Cys Gly Arg Cys Asn Gly Arg Cys Leu Leu
  1               5                  10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 53

Cys Trp Leu Cys Asn Gly Arg Cys Gly Arg
  1               5                  10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 54

Cys Ser Lys Cys Asn Gly Arg Cys Gly His
  1               5                  10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 55

Cys Val Trp Cys Asn Gly Arg Cys Gly Leu
  1               5                  10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 56

Cys Ile Arg Cys Asn Gly Arg Cys Ser Val
  1               5                  10

<210> SEQ ID NO 57
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 57

Cys Gly Glu Cys Asn Gly Arg Cys Val Glu
 1               5                  10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 58

Cys Glu Gly Val Asn Gly Arg Arg Leu Arg
 1               5                  10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 59

Cys Leu Ser Cys Asn Gly Arg Cys Pro Ser
 1               5                  10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 60

Cys Glu Val Cys Asn Gly Arg Cys Ala Leu
 1               5                  10

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 61

Gly Arg Ser Gln Met Gln Ile
 1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 62

His His Thr Arg Phe Val Ser
 1               5
```

```
<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 63

Ser Lys Gly Leu Arg His Arg
 1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 64

Val Ala Ser Val Ser Val Ala
 1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 65

Trp Arg Val Leu Ala Ala Phe
 1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Lys Met Gly Pro Lys Val Trp
 1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 67

Ile Phe Ser Gly Ser Arg Glu
 1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 68

Ser Pro Gly Ser Trp Thr Trp
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 69

Asn Pro Arg Trp Phe Trp Asp
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 70

Gly Arg Trp Tyr Lys Trp Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 71

Ile Lys Ala Arg Ala Ser Pro
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 72

Ser Gly Trp Cys Tyr Arg Cys
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 73

Ala Leu Val Gly Leu Met Arg
1               5

<210> SEQ ID NO 74
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 74

Leu Trp Ala Glu Met Thr Gly
  1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 75

Cys Trp Ser Gly Val Asp Cys
  1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 76

Asp Thr Leu Arg Leu Arg Ile
  1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 77

Ser Lys Ser Ser Gly Val Ser
  1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 78

Ile Val Ala Asp Tyr Gln Arg
  1               5

<210> SEQ ID NO 79
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 79

Val Trp Arg Thr Gly His Leu
```

```
<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 80

Val Val Asp Arg Phe Pro Asp
 1               5

<210> SEQ ID NO 81
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 81

Leu Ser Met Phe Thr Arg Pro
 1               5

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 82

Gly Leu Pro Val Lys Trp Ser
 1               5

<210> SEQ ID NO 83
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 83

Ile Met Tyr Pro Gly Trp Leu
 1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 84

Cys Val Met Val Arg Asp Gly Asp Cys
 1               5

<210> SEQ ID NO 85
<211> LENGTH: 7
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 85

Cys Val Arg Ile Arg Pro Cys
  1               5

<210> SEQ ID NO 86
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 86

Cys Gln Leu Ala Ala Val Cys
  1               5

<210> SEQ ID NO 87
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 87

Cys Gly Val Gly Ser Ser Cys
  1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 88

Cys Val Ser Gly Pro Arg Cys
  1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 89

Cys Gly Leu Ser Asp Ser Cys
  1               5

<210> SEQ ID NO 90
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 90

Cys Gly Glu Gly His Pro Cys
  1               5

<210> SEQ ID NO 91

```
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 91

Cys Tyr Thr Ala Asp Pro Cys
 1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 92

Cys Glu Leu Ser Leu Ile Ser Lys Cys
 1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 93

Cys Pro Glu His Arg Ser Leu Val Cys
 1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 94

Cys Leu Val Val His Glu Ala Ala Cys
 1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 95

Cys Tyr Val Glu Leu His Cys
 1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 96
```

-continued

```
Cys Trp Arg Lys Phe Tyr Cys
  1               5

<210> SEQ ID NO 97
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 97

Cys Phe Trp Pro Asn Arg Cys
  1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 98

Cys Tyr Ser Tyr Phe Leu Ala Cys
  1               5

<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 99

Cys Pro Arg Gly Ser Arg Cys
  1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 100

Cys Arg Leu Gly Ile Ala Cys
  1               5

<210> SEQ ID NO 101
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 101

Cys Asp Asp Ser Trp Lys Cys
  1               5

<210> SEQ ID NO 102
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      Peptide

<400> SEQUENCE: 102

Cys Ala Gln Leu Leu Gln Val Ser Cys
 1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 103

Cys Tyr Pro Ala Asp Pro Cys
 1               5

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 104

Cys Lys Ala Leu Ser Gln Ala Cys
 1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 105

Cys Thr Asp Tyr Val Arg Cys
 1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 106

Cys Gly Glu Thr Met Arg Cys
 1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 107

Gly Ile Cys Lys Asp Asp Trp Cys Gln
 1               5
```

```
<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 108

Thr Ser Cys Asp Pro Ser Leu Cys Glu
  1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 109

Lys Gly Cys Gly Thr Arg Gln Cys Trp
  1               5

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 110

Tyr Arg Cys Arg Glu Val Leu Cys Gln
  1               5

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 111

Cys Trp Gly Thr Gly Leu Cys
  1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 112

Trp Ser Cys Ala Asp Arg Thr Cys Met
  1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 113
```

```
Ala Gly Cys Arg Leu Lys Ser Cys Ala
  1               5
```

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 114

```
Ser Arg Cys Lys Thr Gly Leu Cys Gln
  1               5
```

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 115

```
Pro Ile Cys Glu Val Ser Arg Cys Trp
  1               5
```

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 116

```
Trp Thr Cys Arg Ala Ser Trp Cys Ser
  1               5
```

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 117

```
Gly Arg Cys Leu Leu Met Gln Cys Arg
  1               5
```

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 118

```
Thr Glu Cys Asp Met Ser Arg Cys Met
  1               5
```

<210> SEQ ID NO 119
<211> LENGTH: 9
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 119

Ala Arg Cys Arg Val Asp Pro Cys Val
  1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 120

Cys Ile Glu Gly Val Leu Gly Gly Cys
  1               5

<210> SEQ ID NO 121
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 121

Cys Ser Val Ala Asn Ser Cys
  1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 122

Cys Ser Ser Thr Met Arg Cys
  1               5

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 123

Ser Ile Asp Ser Thr Thr Phe
  1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 124

Gly Pro Ser Arg Val Gly Gly
  1               5
```

```
<210> SEQ ID NO 125
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 125

Trp Trp Ser Gly Leu Glu Ala
 1               5

<210> SEQ ID NO 126
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 126

Leu Gly Thr Asp Val Arg Gln
 1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 127

Leu Val Gly Val Arg Leu Leu
 1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 128

Gly Arg Pro Gly Asp Ile Trp
 1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 129

Thr Val Trp Asn Pro Val Gly
 1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 130

Gly Leu Leu Leu Val Val Pro
  1               5

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 131

Phe Ala Ala Thr Ser Ala Glu
  1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 132

Trp Cys Cys Arg Gln Phe Asn
  1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 133

Val Gly Phe Gly Lys Ala Leu
  1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 134

Asp Ser Ser Leu Arg Leu Pro
  1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 135

Lys Leu Trp Cys Ala Met Ser
  1               5

<210> SEQ ID NO 136
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      Peptide

<400> SEQUENCE: 136

Ser Leu Val Ser Phe Leu Gly
 1               5

<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 137

Gly Ser Phe Ala Phe Leu Val
 1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 138

Ile Ala Ser Val Arg Trp Ala
 1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 139

Thr Trp Gly His Leu Arg Ala
 1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 140

Gln Tyr Arg Glu Gly Leu Val
 1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 141

Gln Ser Ala Asp Arg Ser Val
 1               5
```

```
<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 142

Tyr Met Phe Trp Thr Ser Arg
 1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 143

Leu Val Arg Arg Trp Tyr Leu
 1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 144

Thr Ala Arg Gly Ser Ser Arg
 1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 145

Thr Thr Arg Glu Lys Asn Leu
 1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 146

Pro Lys Trp Leu Leu Phe Ser
 1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide
```

```
<400> SEQUENCE: 147

Leu Arg Thr Asn Val Val His
  1               5

<210> SEQ ID NO 148
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 148

Ala Val Met Gly Leu Ala Ala
  1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 149

Val Arg Asn Ser Leu Arg Asn
  1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 150

Thr Asp Cys Thr Pro Ser Arg Cys Thr
  1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 151

Ser Trp Cys Gln Phe Glu Lys Cys Leu
  1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 152

Val Pro Cys Arg Phe Lys Gln Cys Trp
  1               5

<210> SEQ ID NO 153
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 153

Cys Thr Ala Met Arg Asn Thr Asp Cys
  1               5

<210> SEQ ID NO 154
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 154

Cys Arg Glu Ser Leu Lys Asn Cys
  1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 155

Cys Met Glu Met Gly Val Lys Cys
  1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 156

Val Thr Cys Arg Ser Leu Met Cys Gln
  1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 157

Cys Asn Asn Val Gly Ser Tyr Cys
  1               5

<210> SEQ ID NO 158
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 158

Cys Gly Thr Arg Val Asp His Cys
```

```
                 1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 159

Cys Ile Ser Leu Asp Arg Ser Cys
 1               5

<210> SEQ ID NO 160
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 160

Cys Ala Met Val Ser Met Glu Asp
 1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 161

Cys Tyr Leu Gly Val Ser Asn Cys
 1               5

<210> SEQ ID NO 162
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 162

Cys Tyr Leu Val Asn Val Asp Cys
 1               5

<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 163

Cys Ile Arg Ser Ala Val Ser Cys
 1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
```

Peptide

<400> SEQUENCE: 164

Leu Val Cys Leu Pro Pro Ser Cys Glu
 1               5

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 165

Arg His Cys Phe Ser Gln Trp Cys Ser
 1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 166

Phe Tyr Cys Pro Gly Val Gly Cys Arg
 1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 167

Ile Ser Cys Ala Val Asp Ala Cys Leu
 1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 168

Glu Ala Cys Glu Met Ala Gly Cys Leu
 1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 169

Pro Arg Cys Glu Ser Gln Leu Cys Pro
 1               5

<210> SEQ ID NO 170

```
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 170

Arg Ser Cys Ile Lys His Gln Cys Pro
  1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 171

Gln Trp Cys Ser Arg Arg Trp Cys Thr
  1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 172

Met Phe Cys Arg Met Arg Ser Cys Asp
  1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 173

Gly Ile Cys Lys Asp Leu Trp Cys Gln
  1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 174

Asn Ala Cys Glu Ser Ala Ile Cys Gly
  1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 175
```

```
Ala Pro Cys Gly Leu Leu Ala Cys Ile
  1               5
```

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 176

```
Asn Arg Cys Arg Gly Val Ser Cys Thr
  1               5
```

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 177

```
Phe Pro Cys Glu Gly Lys Lys Cys Leu
  1               5
```

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 178

```
Ala Asp Cys Arg Gln Lys Pro Cys Leu
  1               5
```

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 179

```
Phe Gly Cys Val Met Ala Ser Cys Arg
  1               5
```

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 180

```
Ala Gly Cys Ile Asn Gly Leu Cys Gly
  1               5
```

<210> SEQ ID NO 181
<211> LENGTH: 9
<212> TYPE: PRT
<213> ORGANISM: Artificial Sequence
<220> FEATURE:

```
<223> OTHER INFORMATION: Description of Artificial Sequence: Synthetic
      Peptide

<400> SEQUENCE: 181

Arg Ser Cys Ala Glu Pro Trp Cys Tyr
  1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 182

Asp Thr Cys Arg Ala Leu Arg Cys Asn
  1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 183

Gly Arg Cys Val Asp Gly Gly Cys Thr
  1               5

<210> SEQ ID NO 184
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 184

Tyr Arg Cys Ile Ala Arg Glu Cys Glu
  1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 185

Lys Arg Cys Ser Ser Ser Leu Cys Ala
  1               5

<210> SEQ ID NO 186
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 186

Ile Cys Leu Leu Ala His Cys Ala
  1               5
```

```
<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 187

Gln Ala Cys Pro Met Leu Leu Cys Met
  1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 188

Leu Asp Cys Leu Ser Glu Leu Cys Ser
  1               5

<210> SEQ ID NO 189
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 189

Ala Gly Cys Arg Val Glu Ser Cys
  1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 190

His Thr Cys Leu Val Ala Leu Cys Ala
  1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 191

Ile Tyr Cys Pro Gly Gln Glu Cys Glu
  1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 192
```

```
Arg Leu Cys Ser Leu Tyr Gly Cys Val
 1               5

<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 193

Arg Lys Cys Glu Val Pro Gly Cys Gln
 1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 194

Glu Asp Cys Thr Ser Arg Phe Cys Ser
 1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 195

Leu Glu Cys Val Val Asp Ser Cys Arg
 1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 196

Glu Ile Cys Val Asp Gly Leu Cys Val
 1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 197

Arg Trp Cys Arg Glu Lys Ser Cys Trp
 1               5

<210> SEQ ID NO 198
<211> LENGTH: 9
<212> TYPE: PRT
<213> ORGANISM: Artificial Sequence
```

-continued

```
<220> FEATURE:
<223> OTHER INFORMATION: Description of Artificial Sequence: Synthetic
      Peptide

<400> SEQUENCE: 198

Phe Arg Cys Leu Glu Arg Val Cys Thr
  1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 199

Arg Pro Cys Gly Asp Gln Ala Cys Glu
  1               5

<210> SEQ ID NO 200
<211> LENGTH: 3494
<212> TYPE: DNA
<213> ORGANISM: Homo sapiens
<220> FEATURE:
<221> NAME/KEY: CDS
<222> LOCATION: (121)..(3024)

<400> SEQUENCE: 200 taattttgc ccagtctgcc tgttgtgggg ctcctcccct ttggggatat aagcccggcc      60
tggggctgct ccgttctctg cctggcctga ggctccctga gccgcctccc caccatcacc    120 atg gcc aag ggc ttc tat att tcc aag tcc ctg ggc atc ctg ggg atc     168
Met Ala Lys Gly Phe Tyr Ile Ser Lys Ser Leu Gly Ile Leu Gly Ile
  1               5                  10                  15 ctc ctg ggc gtg gca gcc gtg tgc aca atc atc gca ctg tca gtg gtg    216
Leu Leu Gly Val Ala Ala Val Cys Thr Ile Ile Ala Leu Ser Val Val
                 20                  25                  30 tac tcc cag gag aag aac aag aac gcc aac agc tcc ccc gtg gcc tcc    264
Tyr Ser Gln Glu Lys Asn Lys Asn Ala Asn Ser Ser Pro Val Ala Ser
         35                  40                  45 acc acc ccg tcc gcc tca gcc acc acc aac ccc gcc tcg gcc acc acc    312
Thr Thr Pro Ser Ala Ser Ala Thr Thr Asn Pro Ala Ser Ala Thr Thr
     50                  55                  60 ttg gac caa agt aaa gcg tgg aat cgt tac cgc ctc ccc aac acg ctg    360
Leu Asp Gln Ser Lys Ala Trp Asn Arg Tyr Arg Leu Pro Asn Thr Leu
 65                  70                  75                  80 aaa ccc gat tcc tac cag gtg acg ctg aga ccg tac ctc acc ccc aat    408
Lys Pro Asp Ser Tyr Gln Val Thr Leu Arg Pro Tyr Leu Thr Pro Asn
                 85                  90                  95 gac agg ggc ctg tac gtt ttt aag ggc tcc agc acc gtc cgt ttc acc    456
Asp Arg Gly Leu Tyr Val Phe Lys Gly Ser Ser Thr Val Arg Phe Thr
            100                 105                 110 tgc aag gag gcc act gac gtc atc atc atc cac agc aag aag ctc aac    504
Cys Lys Glu Ala Thr Asp Val Ile Ile Ile His Ser Lys Lys Leu Asn
        115                 120                 125 tac acc ctc agc cag ggg cac agg gtg gtc ctg cgt ggt gtg gga ggc    552
Tyr Thr Leu Ser Gln Gly His Arg Val Val Leu Arg Gly Val Gly Gly
    130                 135                 140 tcc cag ccc ccc gac att gac aag act gag ctg gtg gag ccc acc gag    600
Ser Gln Pro Pro Asp Ile Asp Lys Thr Glu Leu Val Glu Pro Thr Glu
145                 150                 155                 160 tac ctg gtg gtg cac ctc aag ggc tcc ctg gtg aag gac agc cag tat    648
```

```
Tyr Leu Val Val His Leu Lys Gly Ser Leu Val Lys Asp Ser Gln Tyr
                165                 170                 175 gag atg gac agc gag ttc gag ggg gag ttg gca gat gac ctg gcg ggc      696
Glu Met Asp Ser Glu Phe Glu Gly Glu Leu Ala Asp Asp Leu Ala Gly
            180                 185                 190 ttc tac cgc agc gag tac atg gag ggc aat gtc aga aag gtg gtg gcc      744
Phe Tyr Arg Ser Glu Tyr Met Glu Gly Asn Val Arg Lys Val Val Ala
        195                 200                 205 act aca cag atg cag gct gca gat gcc cgg aag tcc ttc cca tgc ttc      792
Thr Thr Gln Met Gln Ala Ala Asp Ala Arg Lys Ser Phe Pro Cys Phe
    210                 215                 220 gat gag ccg gcc atg aag gcc gag ttc aac atc acg ctt atc cac ccc      840
Asp Glu Pro Ala Met Lys Ala Glu Phe Asn Ile Thr Leu Ile His Pro
225                 230                 235                 240 aag gac ctg aca gcc ctg tcc aac atg ctt ccc aaa ggt ccc agc acc      888
Lys Asp Leu Thr Ala Leu Ser Asn Met Leu Pro Lys Gly Pro Ser Thr
                245                 250                 255 cca ctt cca gaa gac ccc aac tgg aat gtc act gag ttc cac acc acg      936
Pro Leu Pro Glu Asp Pro Asn Trp Asn Val Thr Glu Phe His Thr Thr
            260                 265                 270 ccc aag atg tcc acg tac ttg ctg gcc ttc att gtc agt gag ttc gac      984
Pro Lys Met Ser Thr Tyr Leu Leu Ala Phe Ile Val Ser Glu Phe Asp
        275                 280                 285 tac gtg gag aag cag gca tcc aat ggt gtc ttg atc cgg atc tgg gcc     1032
Tyr Val Glu Lys Gln Ala Ser Asn Gly Val Leu Ile Arg Ile Trp Ala
    290                 295                 300 cgg ccc agt gcc att gcg gcg ggc cac ggc gat tat gcc ctg aac gtg     1080
Arg Pro Ser Ala Ile Ala Ala Gly His Gly Asp Tyr Ala Leu Asn Val
305                 310                 315                 320 acg ggc ccc atc ctt aac ttc ttt gct ggt cat tat gac aca ccc tac     1128
Thr Gly Pro Ile Leu Asn Phe Phe Ala Gly His Tyr Asp Thr Pro Tyr
                325                 330                 335 cca ctc cca aaa tca gac cag att ggc ctg cca gac ttc aac gcc ggc     1176
Pro Leu Pro Lys Ser Asp Gln Ile Gly Leu Pro Asp Phe Asn Ala Gly
            340                 345                 350 gcc atg gag aac tgg gga ctg gtg acc tac cgg gag aac tcc ctg ctg     1224
Ala Met Glu Asn Trp Gly Leu Val Thr Tyr Arg Glu Asn Ser Leu Leu
        355                 360                 365 ttc gac ccc ctg tcc tcc tcc agc agc aac aag gag cgg gtg gtc act     1272
Phe Asp Pro Leu Ser Ser Ser Ser Ser Asn Lys Glu Arg Val Val Thr
    370                 375                 380 gtg att gct cat gag ctg gcc cac cag tgg ttc ggg aac ctg gtg acc     1320
Val Ile Ala His Glu Leu Ala His Gln Trp Phe Gly Asn Leu Val Thr
385                 390                 395                 400 ata gag tgg tgg aat gac ctg tgg ctg aac gag ggc ttc gcc tcc tac     1368
Ile Glu Trp Trp Asn Asp Leu Trp Leu Asn Glu Gly Phe Ala Ser Tyr
                405                 410                 415 gtg gag tac ctg ggt gct gac tat gcg gag ccc acc tgg aac ttg aaa     1416
Val Glu Tyr Leu Gly Ala Asp Tyr Ala Glu Pro Thr Trp Asn Leu Lys
            420                 425                 430 gac ctc atg gtg ctg aat gat gtg tac cgc gtg atg gca gtg gat gca     1464
Asp Leu Met Val Leu Asn Asp Val Tyr Arg Val Met Ala Val Asp Ala
        435                 440                 445 ctg gcc tcc tcc cac ccg ctg tcc aca ccc gcc tcg gag atc aac acg     1512
Leu Ala Ser Ser His Pro Leu Ser Thr Pro Ala Ser Glu Ile Asn Thr
    450                 455                 460 ccg gcc cag atc agt gag ctg ttt gac gcc atc tcc tac agc aag ggc     1560
Pro Ala Gln Ile Ser Glu Leu Phe Asp Ala Ile Ser Tyr Ser Lys Gly
465                 470                 475                 480
```

```
gcc tca gtc ctc agg atg ctc tcc agc ttc ctg tcc gag gac gta ttc      1608
Ala Ser Val Leu Arg Met Leu Ser Ser Phe Leu Ser Glu Asp Val Phe
                485                 490                 495 aag cag ggc ctg gcg tcc tac ctc cac acc ttt gcc tac cag aac acc      1656
Lys Gln Gly Leu Ala Ser Tyr Leu His Thr Phe Ala Tyr Gln Asn Thr
        500                 505                 510 atc tac ctg aac ctg tgg gac cac ctg cag gag gct gtg aac aac cgg      1704
Ile Tyr Leu Asn Leu Trp Asp His Leu Gln Glu Ala Val Asn Asn Arg
    515                 520                 525 tcc atc caa ctc ccc acc acc gtg cgg gac atc atg aac cgc tgg acc      1752
Ser Ile Gln Leu Pro Thr Thr Val Arg Asp Ile Met Asn Arg Trp Thr
530                 535                 540 ctg cag atg ggc ttc ccg gtc atc acg gtg gat acc agc acg ggg acc      1800
Leu Gln Met Gly Phe Pro Val Ile Thr Val Asp Thr Ser Thr Gly Thr
545                 550                 555                 560 ctt tcc cag gag cac ttc ctc ctt gac ccc gat tcc aat gtt acc cgc      1848
Leu Ser Gln Glu His Phe Leu Leu Asp Pro Asp Ser Asn Val Thr Arg
                565                 570                 575 ccc tca gaa ttc aac tac gtg tgg att gtg ccc atc aca tcc atc aga      1896
Pro Ser Glu Phe Asn Tyr Val Trp Ile Val Pro Ile Thr Ser Ile Arg
                580                 585                 590 gat ggc aga cag cag cag gac tac tgg ctg ata gat gta aga gcc cag      1944
Asp Gly Arg Gln Gln Gln Asp Tyr Trp Leu Ile Asp Val Arg Ala Gln
            595                 600                 605 aac gat ctc ttc agc aca tca ggc aat gag tgg gtc ctg ctg aac ctc      1992
Asn Asp Leu Phe Ser Thr Ser Gly Asn Glu Trp Val Leu Leu Asn Leu
610                 615                 620 aat gtg acg ggc tat tac cgg gtg aac tac gac gaa gag aac tgg agg      2040
Asn Val Thr Gly Tyr Tyr Arg Val Asn Tyr Asp Glu Glu Asn Trp Arg
625                 630                 635                 640 aag att cag act cag ctg cag aga gac cac tcg gcc atc cct gtc atc      2088
Lys Ile Gln Thr Gln Leu Gln Arg Asp His Ser Ala Ile Pro Val Ile
                645                 650                 655 aat cgg gca cag atc att aat gac gcc ttc aac ctg gcc agt gcc cat      2136
Asn Arg Ala Gln Ile Ile Asn Asp Ala Phe Asn Leu Ala Ser Ala His
                660                 665                 670 aag gtc cct gtc act ctg gcg ctg aac aac acc ctc ttc ctg att gaa      2184
Lys Val Pro Val Thr Leu Ala Leu Asn Asn Thr Leu Phe Leu Ile Glu
            675                 680                 685 gag aga cag tac atg ccc tgg gag gcc gcc ctg agc agc ctg agc tac      2232
Glu Arg Gln Tyr Met Pro Trp Glu Ala Ala Leu Ser Ser Leu Ser Tyr
690                 695                 700 ttc aag ctc atg ttt gac cgc tcc gag gtc tat ggc ccc atg aag aac      2280
Phe Lys Leu Met Phe Asp Arg Ser Glu Val Tyr Gly Pro Met Lys Asn
705                 710                 715                 720 tac ctg aag aag cag gtc aca ccc ctc ttc att cac ttc aga aat aat      2328
Tyr Leu Lys Lys Gln Val Thr Pro Leu Phe Ile His Phe Arg Asn Asn
                725                 730                 735 acc aac aac tgg agg gag atc cca gaa aac ctg atg gac cag tac agc      2376
Thr Asn Asn Trp Arg Glu Ile Pro Glu Asn Leu Met Asp Gln Tyr Ser
            740                 745                 750 gag gtt aat gcc atc agc acc gcc tgc tcc aac gga gtt cca gag tgt      2424
Glu Val Asn Ala Ile Ser Thr Ala Cys Ser Asn Gly Val Pro Glu Cys
            755                 760                 765 gag gag atg gtc tct ggc ctt ttc aag cag tgg atg gag aac ccc aat      2472
Glu Glu Met Val Ser Gly Leu Phe Lys Gln Trp Met Glu Asn Pro Asn
770                 775                 780 aat aac ccg atc cac ccc aac ctg cgg tcc acc gtc tac tgc aac gct      2520
Asn Asn Pro Ile His Pro Asn Leu Arg Ser Thr Val Tyr Cys Asn Ala
785                 790                 795                 800
```

```
atc gcc cag ggc ggg gag gag gag tgg gac ttc gcc tgg gag cag ttc         2568
Ile Ala Gln Gly Gly Glu Glu Glu Trp Asp Phe Ala Trp Glu Gln Phe
                805                 810                 815
cga aat gcc aca ctg gtc aat gag gct gac aag ctc cgg gca gcc ctg         2616
Arg Asn Ala Thr Leu Val Asn Glu Ala Asp Lys Leu Arg Ala Ala Leu
            820                 825                 830
gcc tgc agc aaa gag ttg tgg atc ctg aac agg tac ctg agc tac acc         2664
Ala Cys Ser Lys Glu Leu Trp Ile Leu Asn Arg Tyr Leu Ser Tyr Thr
        835                 840                 845
ctg aac ccg gac tta atc cgg aag cag gac gcc acc tct acc atc atc         2712
Leu Asn Pro Asp Leu Ile Arg Lys Gln Asp Ala Thr Ser Thr Ile Ile
    850                 855                 860
agc att acc aac aac gtc att ggg caa ggt ctg gtc tgg gac ttt gtc         2760
Ser Ile Thr Asn Asn Val Ile Gly Gln Gly Leu Val Trp Asp Phe Val
865                 870                 875                 880
cag agc aac tgg aag aag ctt ttt aac gat tat ggt ggt ggc tcg ttc         2808
Gln Ser Asn Trp Lys Lys Leu Phe Asn Asp Tyr Gly Gly Gly Ser Phe
                885                 890                 895
tcc ttc tcc aac ctc atc cag gca gtg aca cga cga ttc tcc acc gag         2856
Ser Phe Ser Asn Leu Ile Gln Ala Val Thr Arg Arg Phe Ser Thr Glu
            900                 905                 910
tat gag ctg cag cag ctg gag cag ttc aag aag gac aac gag gaa aca         2904
Tyr Glu Leu Gln Gln Leu Glu Gln Phe Lys Lys Asp Asn Glu Glu Thr
        915                 920                 925
ggc ttc ggc tca ggc acc cgg gcc ctg gag caa gcc ctg gag aag acg         2952
Gly Phe Gly Ser Gly Thr Arg Ala Leu Glu Gln Ala Leu Glu Lys Thr
    930                 935                 940
aaa gcc aac atc aag tgg gtg aag gag aac aag gag gtg gtc ctc cag         3000
Lys Ala Asn Ile Lys Trp Val Lys Glu Asn Lys Glu Val Val Leu Gln
945                 950                 955                 960
tgg ttc aca gaa aac agc aaa tag tccccagccc ttgaagtcac ccggccccga       3054
Trp Phe Thr Glu Asn Ser Lys
                965
tgcaaggtgc ccacatgtgt ccatcccagc ggctggtgca gggcctccat tcctggagcc      3114
cgaggcacca gtgtcctccc ctcaaggaca aagtctccag cccacgttct ctctgcctgt      3174
gagccagtct agttcctgat gacccaggct gcctgagcac ctcccagccc ctgcccctca      3234
tgccaacccc gccctaggcc tggcatggca cctgtcgccc agtgcctggg ggctgatctc      3294
agggaagccc agctccaggg ccagatgagc agaagctctc gatggacaat gaacggcctt      3354
gctgggggcc gccctgtacc ctctttcacc tttccctaaa gacccaaat  ctgaggaatc      3414
aacagggcag cagatctgta tattttttc  taagagaaaa tgtaaataaa ggatttctag      3474
atgaaaaaaa aaaaaaaaa                                                   3494
```

<210> SEQ ID NO 201
<211> LENGTH: 967
<212> TYPE: PRT
<213> ORGANISM: Homo sapiens

<400> SEQUENCE: 201

```
Met Ala Lys Gly Phe Tyr Ile Ser Lys Ser Leu Gly Ile Leu Gly Ile
1               5                   10                  15
Leu Leu Gly Val Ala Ala Val Cys Thr Ile Ile Ala Leu Ser Val Val
                20                  25                  30
Tyr Ser Gln Glu Lys Asn Lys Asn Ala Asn Ser Ser Pro Val Ala Ser
            35                  40                  45
Thr Thr Pro Ser Ala Ser Ala Thr Asn Pro Ala Ser Ala Thr Thr
        50                  55                  60
Leu Asp Gln Ser Lys Ala Trp Asn Arg Tyr Arg Leu Pro Asn Thr Leu
65                  70                  75                  80
Lys Pro Asp Ser Tyr Gln Val Thr Leu Arg Pro Tyr Leu Thr Pro Asn
```

```
                        85                      90                      95
Asp Arg Gly Leu Tyr Val Phe Lys Gly Ser Ser Thr Val Arg Phe Thr
                100                     105                     110
Cys Lys Glu Ala Thr Asp Val Ile Ile Ile His Ser Lys Lys Leu Asn
                115                     120                     125
Tyr Thr Leu Ser Gln Gly His Arg Val Leu Arg Gly Val Gly Gly
                130                     135                     140
Ser Gln Pro Pro Asp Ile Asp Lys Thr Glu Leu Val Glu Pro Thr Glu
145                     150                     155                     160
Tyr Leu Val Val His Leu Lys Gly Ser Leu Val Lys Asp Ser Gln Tyr
                165                     170                     175
Glu Met Asp Ser Glu Phe Glu Gly Leu Ala Asp Asp Leu Ala Gly
                180                     185                     190
Phe Tyr Arg Ser Glu Tyr Met Glu Gly Asn Val Arg Lys Val Val Ala
                195                     200                     205
Thr Thr Gln Met Gln Ala Ala Asp Ala Arg Lys Ser Phe Pro Cys Phe
                210                     215                     220
Asp Glu Pro Ala Met Lys Ala Glu Phe Asn Ile Thr Leu Ile His Pro
225                     230                     235                     240
Lys Asp Leu Thr Ala Leu Ser Asn Met Leu Pro Lys Gly Pro Ser Thr
                245                     250                     255
Pro Leu Pro Glu Asp Pro Asn Trp Asn Val Thr Glu Phe His Thr Thr
                260                     265                     270
Pro Lys Met Ser Thr Tyr Leu Leu Ala Phe Ile Val Ser Glu Phe Asp
                275                     280                     285
Tyr Val Glu Lys Gln Ala Ser Asn Gly Val Leu Ile Arg Ile Trp Ala
                290                     295                     300
Arg Pro Ser Ala Ile Ala Ala Gly His Gly Asp Tyr Ala Leu Asn Val
305                     310                     315                     320
Thr Gly Pro Ile Leu Asn Phe Phe Ala Gly His Tyr Asp Thr Pro Tyr
                325                     330                     335
Pro Leu Pro Lys Ser Asp Gln Ile Gly Leu Pro Asp Phe Asn Ala Gly
                340                     345                     350
Ala Met Glu Asn Trp Gly Leu Val Thr Tyr Arg Glu Asn Ser Leu Leu
                355                     360                     365
Phe Asp Pro Leu Ser Ser Ser Ser Asn Lys Glu Arg Val Val Thr
                370                     375                     380
Val Ile Ala His Glu Leu Ala His Gln Trp Phe Gly Asn Leu Val Thr
385                     390                     395                     400
Ile Glu Trp Trp Asn Asp Leu Trp Leu Asn Glu Gly Phe Ala Ser Tyr
                405                     410                     415
Val Glu Tyr Leu Gly Ala Asp Tyr Ala Glu Pro Thr Trp Asn Leu Lys
                420                     425                     430
Asp Leu Met Val Leu Asn Asp Val Tyr Arg Val Met Ala Val Asp Ala
                435                     440                     445
Leu Ala Ser Ser His Pro Leu Ser Thr Pro Ala Ser Glu Ile Asn Thr
                450                     455                     460
Pro Ala Gln Ile Ser Glu Leu Phe Asp Ala Ile Ser Tyr Ser Lys Gly
465                     470                     475                     480
Ala Ser Val Leu Arg Met Leu Ser Ser Phe Leu Ser Glu Asp Val Phe
                485                     490                     495
Lys Gln Gly Leu Ala Ser Tyr Leu His Thr Phe Ala Tyr Gln Asn Thr
                500                     505                     510
Ile Tyr Leu Asn Leu Trp Asp His Leu Gln Glu Ala Val Asn Asn Arg
                515                     520                     525
Ser Ile Gln Leu Pro Thr Thr Val Arg Asp Ile Met Asn Arg Trp Thr
                530                     535                     540
Leu Gln Met Gly Phe Pro Val Ile Thr Val Asp Thr Ser Thr Gly Thr
545                     550                     555                     560
Leu Ser Gln Glu His Phe Leu Leu Asp Pro Asp Ser Asn Val Thr Arg
                565                     570                     575
Pro Ser Glu Phe Asn Tyr Val Trp Ile Val Pro Ile Thr Ser Ile Arg
                580                     585                     590
Asp Gly Arg Gln Gln Asp Tyr Trp Leu Ile Asp Val Arg Ala Gln
                595                     600                     605
Asn Asp Leu Phe Ser Thr Ser Gly Asn Glu Trp Val Leu Leu Asn Leu
                610                     615                     620
Asn Val Thr Gly Tyr Tyr Arg Val Asn Tyr Asp Glu Glu Asn Trp Arg
625                     630                     635                     640
Lys Ile Gln Thr Gln Leu Gln Arg Asp His Ser Ala Ile Pro Val Ile
                645                     650                     655
Asn Arg Ala Gln Ile Ile Asn Asp Ala Phe Asn Leu Ala Ser Ala His
                660                     665                     670
Lys Val Pro Val Thr Leu Ala Leu Asn Asn Thr Leu Phe Leu Ile Glu
                675                     680                     685
Glu Arg Gln Tyr Met Pro Trp Glu Ala Ala Leu Ser Ser Leu Ser Tyr
                690                     695                     700
Phe Lys Leu Met Phe Asp Arg Ser Glu Val Tyr Gly Pro Met Lys Asn
705                     710                     715                     720
```

```
Tyr Leu Lys Lys Gln Val Thr Pro Leu Phe Ile His Phe Arg Asn Asn
                725                 730                 735
Thr Asn Asn Trp Arg Glu Ile Pro Glu Asn Leu Met Asp Gln Tyr Ser
            740                 745                 750
Glu Val Asn Ala Ile Ser Thr Ala Cys Ser Asn Gly Val Pro Glu Cys
        755                 760                 765
Glu Glu Met Val Ser Gly Leu Phe Lys Gln Trp Met Glu Asn Pro Asn
    770                 775                 780
Asn Asn Pro Ile His Pro Asn Leu Arg Ser Thr Val Tyr Cys Asn Ala
785                 790                 795                 800
Ile Ala Gln Gly Gly Glu Glu Trp Asp Phe Ala Trp Glu Gln Phe
                805                 810                 815
Arg Asn Ala Thr Leu Val Asn Glu Ala Asp Lys Leu Arg Ala Ala Leu
                820                 825                 830
Ala Cys Ser Lys Glu Leu Trp Ile Leu Asn Arg Tyr Leu Ser Tyr Thr
                835                 840                 845
Leu Asn Pro Asp Leu Ile Arg Lys Gln Asp Ala Thr Ser Thr Ile Ile
850                 855                 860
Ser Ile Thr Asn Asn Val Ile Gly Gln Gly Leu Val Trp Asp Phe Val
865                 870                 875                 880
Gln Ser Asn Trp Lys Lys Leu Phe Asn Asp Tyr Gly Gly Gly Ser Phe
                885                 890                 895
Ser Phe Ser Asn Leu Ile Gln Ala Val Thr Arg Arg Phe Ser Thr Glu
            900                 905                 910
Tyr Glu Leu Gln Gln Leu Glu Gln Phe Lys Lys Asp Asn Glu Glu Thr
                915                 920                 925
Gly Phe Gly Ser Gly Thr Arg Ala Leu Glu Gln Ala Leu Glu Lys Thr
        930                 935                 940
Lys Ala Asn Ile Lys Trp Val Lys Glu Asn Lys Glu Val Val Leu Gln
945                 950                 955                 960
Trp Phe Thr Glu Asn Ser Lys
                965
```

<210> SEQ ID NO 202
<211> LENGTH: 66
<212> TYPE: DNA
<213> ORGANISM: Artificial Sequence
<220> FEATURE:
<221> NAME/KEY: unsure
<222> LOCATION: (22)..(23)
<223> OTHER INFORMATION: any
<220> FEATURE:
<221> NAME/KEY: unsure
<222> LOCATION: (25)..(26)
<223> OTHER INFORMATION: any
<220> FEATURE:
<221> NAME/KEY: unsure
<222> LOCATION: (43)..(44)
<223> OTHER INFORMATION: any
<220> FEATURE:
<221> NAME/KEY: unsure
<222> LOCATION: (46)..(47)
<220> FEATURE:
<223> OTHER INFORMATION: Description of Artificial Sequence:synthetic

<400> SEQUENCE: 202
cactcggccg acggggcttg tnnynnytgt aatggtaggt gtnnynnygg ggccgctggg    60
gcagaa                                                              66

<210> SEQ ID NO 203
<211> LENGTH: 66
<212> TYPE: DNA
<213> ORGANISM: Artificial Sequence
<220> FEATURE:
<221> NAME/KEY: unsure
<222> LOCATION: (22)..(23)
<223> OTHER INFORMATION: any
<220> FEATURE:
<221> NAME/KEY: unsure
<222> LOCATION: (25)..(26)
<223> OTHER INFORMATION: any
<220> FEATURE:
<221> NAME/KEY: unsure
<222> LOCATION: (43)..(44)
<223> OTHER INFORMATION: any

```
<220> FEATURE:
<221> NAME/KEY: unsure
<222> LOCATION: (46)..(47)
<223> OTHER INFORMATION: any
<220> FEATURE:
<223> OTHER INFORMATION: Description of Artificial Sequence:synthetic
<220> FEATURE:
<221> NAME/KEY: unsure
<222> LOCATION: (28)..(29)
<223> OTHER INFORMATION: any

<400> SEQUENCE: 203
cactcggccg acggggcttg tnnynnynny aatgggaggn nynnynnygg ggccgctggg      60
gcagaa                                                                66

<210> SEQ ID NO 204
<211> LENGTH: 69
<212> TYPE: DNA
<213> ORGANISM: Artificial Sequence
<220> FEATURE:
<221> NAME/KEY: unsure
<222> LOCATION: (40)..(41)
<223> OTHER INFORMATION: any
<220> FEATURE:
<221> NAME/KEY: unsure
<222> LOCATION: (46)..(47)
<223> OTHER INFORMATION: any
<220> FEATURE:
<221> NAME/KEY: unsure
<222> LOCATION: (43)..(44)
<223> OTHER INFORMATION: any
<220> FEATURE:
<223> OTHER INFORMATION: Description of Artificial Sequence:synthetic
<220> FEATURE:
<221> NAME/KEY: unsure
<222> LOCATION: (34)..(35)
<223> OTHER INFORMATION: any
<220> FEATURE:
<221> NAME/KEY: unsure
<222> LOCATION: (37)..(38)
<223> OTHER INFORMATION: any
<220> FEATURE:
<221> NAME/KEY: unsure
<222> LOCATION: (49)..(50)
<223> OTHER INFORMATION: any

<400> SEQUENCE: 204
cactcggccg acggggcttg taatgggaga tgtnnynnyn nynnynnynn ygggccgct       60 ggggcagaa                                                             69

<210> SEQ ID NO 205
<211> LENGTH: 38
<212> TYPE: DNA
<213> ORGANISM: Oryctanthus occidentalis
<220> FEATURE:
<221> NAME/KEY: unsure
<222> LOCATION: (34)..(35)
<223> OTHER INFORMATION: any
<220> FEATURE:
<221> NAME/KEY: unsure
<222> LOCATION: (37)..(38)
<223> OTHER INFORMATION: any
<220> FEATURE:
<221> NAME/KEY: unsure
<222> LOCATION: (40)..(41)
<223> OTHER INFORMATION: any
<220> FEATURE:
<221> NAME/KEY: unsure
<222> LOCATION: (43)..(44)
<223> OTHER INFORMATION: any
<220> FEATURE:
<221> NAME/KEY: unsure
<222> LOCATION: (46)..(47)
```

<223> OTHER INFORMATION: any
<220> FEATURE:
<221> NAME/KEY: unsure
<222> LOCATION: (49)..(50)
<223> OTHER INFORMATION: any
<220> FEATURE:
<223> OTHER INFORMATION: Description of Artificial Sequence:synthetic

<400> SEQUENCE: 205
gggcccaggc ggccgagctc gtgmtgaccc agactcca                              38

<210> SEQ ID NO 206
<211> LENGTH: 38
<212> TYPE: DNA
<213> ORGANISM: Oryctanthus occidentalis
<220> FEATURE:
<223> OTHER INFORMATION: Description of Artificial Sequence:synthetic

<400> SEQUENCE: 206
gggcccaggc ggccgagctc gatmtgaccc agactcca                              38

<210> SEQ ID NO 207
<211> LENGTH: 38
<212> TYPE: DNA
<213> ORGANISM: Oryctanthus occidentalis

<400> SEQUENCE: 207
gggcccaggc ggccgagctc gtgatgaccc agactgaa                              38

<210> SEQ ID NO 208
<211> LENGTH: 42
<212> TYPE: DNA
<213> ORGANISM: Oryctanthus occidentalis

<400> SEQUENCE: 208
ggaagatcta gaggaaccac ctttgatttc cacattggtg cc                         42

<210> SEQ ID NO 209
<211> LENGTH: 42
<212> TYPE: DNA
<213> ORGANISM: Oryctanthus occidentalis

<400> SEQUENCE: 209
ggaagatcta gaggaaccac ctttgatttc cacattggtg cc                         42

<210> SEQ ID NO 210
<211> LENGTH: 41
<212> TYPE: DNA
<213> ORGANISM: Oryctanthus occidentalis

<400> SEQUENCE: 210
ggaagatcta gaggaaccac cttgacsacc acctcggtcc c                          41

<210> SEQ ID NO 211
<211> LENGTH: 40
<212> TYPE: DNA
<213> ORGANISM: Oryctanthus occidentalis

<400> SEQUENCE: 211
gggcccaggc ggccgagctc gtgctgactc agtcgccctc                            40

<210> SEQ ID NO 212
<211> LENGTH: 45
<212> TYPE: DNA
<213> ORGANISM: Oryctanthus occidentalis -continued

<400> SEQUENCE: 212
ggaagatcta gaggaaccac cgcctgtgac ggtcagctgg gtccc          45

<210> SEQ ID NO 213
<211> LENGTH: 42
<212> TYPE: DNA
<213> ORGANISM: Oryctanthus occidentalis

<400> SEQUENCE: 213
ggtggttcct ctagatcttc ccagtcggtg gaggagtccr gg             42

<210> SEQ ID NO 214
<211> LENGTH: 42
<212> TYPE: DNA
<213> ORGANISM: Oryctanthus occidentalis

<400> SEQUENCE: 214
ggtggttcct ctagatcttc ccagtcggtg aaggagtccg ag             42

<210> SEQ ID NO 215
<211> LENGTH: 42
<212> TYPE: DNA
<213> ORGANISM: Oryctanthus occidentalis

<400> SEQUENCE: 215
ggtggttcct ctagatcttc ccagtcgytg gaggagtccg gg             42

<210> SEQ ID NO 216
<211> LENGTH: 44
<212> TYPE: DNA
<213> ORGANISM: Oryctanthus occidentalis

<400> SEQUENCE: 216
ggtggttcct ctagatcttc ccagsagcag ctgrtggagt ccgg           44

<210> SEQ ID NO 217
<211> LENGTH: 46
<212> TYPE: DNA
<213> ORGANISM: Oryctanthus occidentalis

<400> SEQUENCE: 217
cctggccggc ctggccacta gtgactgayg gagccttagg ttgccc         46

<210> SEQ ID NO 218
<211> LENGTH: 41
<212> TYPE: DNA
<213> ORGANISM: Oryctanthus occidentalis

<400> SEQUENCE: 218
gaggaggagg aggaggaggc ggggcccagg cggccgagct c              41

<210> SEQ ID NO 219
<211> LENGTH: 41
<212> TYPE: DNA
<213> ORGANISM: Oryctanthus occidentalis

<400> SEQUENCE: 219
gaggaggagg aggaggagcc tggccggcct ggccactagt g              41

<210> SEQ ID NO 220
<211> LENGTH: 7
<212> TYPE: PRT

```
<213> ORGANISM: Artificial Sequence
<220> FEATURE:
<223> OTHER INFORMATION: Description of Artificial Sequence: Synthetic

<400> SEQUENCE: 220

Cys Arg Gly Asp Gly Trp Cys
 1               5

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic

<400> SEQUENCE: 221

Cys Ala Arg Ala Cys
 1               5

<210> SEQ ID NO 222
<211> LENGTH: 9
<212> TYPE: PRT
<213> ORGANISM: Artificial Sequence
<220> FEATURE:
<221> NAME/KEY: UNSURE
<222> LOCATION: (1)..(2)
<223> OTHER INFORMATION: any amino acid encoded by nny
<220> FEATURE:
<221> NAME/KEY: UNSURE
<222> LOCATION: (8)..(9)
<223> OTHER INFORMATION: any amino acid encoded by nny
<220> FEATURE:
<223> OTHER INFORMATION: Description of Artificial Sequence:synthetic

<400> SEQUENCE: 222

Xaa Xaa Cys Asn Gly Arg Cys Xaa Xaa
 1               5

<210> SEQ ID NO 223
<211> LENGTH: 11
<212> TYPE: PRT
<213> ORGANISM: Artificial Sequence
<220> FEATURE:
<221> NAME/KEY: UNSURE
<222> LOCATION: (2)..(3)
<223> OTHER INFORMATION: any amino acid encoded by nny
<220> FEATURE:
<221> NAME/KEY: SITE
<222> LOCATION: (4)
<223> OTHER INFORMATION: Cysteine or any amino acid (c/x)
<220> FEATURE:
<221> NAME/KEY: SITE
<222> LOCATION: (8)
<223> OTHER INFORMATION: Cysteine or any amino acid (c/x)
<220> FEATURE:
<221> NAME/KEY: UNSURE
<222> LOCATION: (9)..(10)
<223> OTHER INFORMATION: any amino acid encoded by nny
<220> FEATURE:
<223> OTHER INFORMATION: Description of Artificial Sequence:synthetic

<400> SEQUENCE: 223

Cys Xaa Xaa Xaa Asn Gly Arg Xaa Xaa Xaa Cys
 1               5                  10

<210> SEQ ID NO 224
<211> LENGTH: 11
<212> TYPE: PRT
<213> ORGANISM: Artificial Sequence
<220> FEATURE:
<221> NAME/KEY: UNSURE
```

```
<222> LOCATION: (6)..(11)
<223> OTHER INFORMATION: any amino acid by nny
<220> FEATURE:
<223> OTHER INFORMATION: Description of Artificial Sequence:synthetic

<400> SEQUENCE: 224

Cys Asn Gly Arg Cys Xaa Xaa Xaa Xaa Xaa Xaa
  1               5                  10

<210> SEQ ID NO 225
<211> LENGTH: 18
<212> TYPE: DNA
<213> ORGANISM: Artificial Sequence
<220> FEATURE:
<221> NAME/KEY: UNSURE
<222> LOCATION: (6)..(11)
<223> OTHER INFORMATION: any amino acid encoded by nny
<220> FEATURE:
<223> OTHER INFORMATION: Description of Artificial Sequence:synthetic

<400> SEQUENCE: 225
ttctgcccca gcggcccc                                                 18

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence:synthetic
<220> FEATURE:
<221> NAME/KEY: unsure
<222> LOCATION: (4)..(5)
<223> OTHER INFORMATION: any
<220> FEATURE:
<221> NAME/KEY: unsure
<222> LOCATION: (7)..(8)
<223> OTHER INFORMATION: any
<220> FEATURE:
<221> NAME/KEY: unsure
<222> LOCATION: (10)..(11)
<223> OTHER INFORMATION: any
<220> FEATURE:
<221> NAME/KEY: unsure
<222> LOCATION: (13)..(14)
<223> OTHER INFORMATION: any
<220> FEATURE:
<221> NAME/KEY: unsure
<222> LOCATION: (16)..(17)
<223> OTHER INFORMATION: any

<400> SEQUENCE: 226
tgtnnknnkn nknnknnktg t                                             21
```